US007247431B2

(12) United States Patent
Xia

(10) Patent No.: US 7,247,431 B2
(45) Date of Patent: Jul. 24, 2007

(54) HUMAN SOURCE LEADING SEQUENCE, GENE VECTOR AND GENE EXPRESSION STRATEGY

(76) Inventor: Jiahui Xia, c/o National Lab of Medical Genetics of China, Central South University, 88 Xiangya Road, Changsha, Hunan 410078 (CN)

( * ) Notice: Subject to any disclaimer, the term of this patent is extended or adjusted under 35 U.S.C. 154(b) by 43 days.

(21) Appl. No.: 10/333,069

(22) PCT Filed: Feb. 16, 2001

(86) PCT No.: PCT/CN01/00126

§ 371 (c)(1),
(2), (4) Date: Mar. 17, 2003

(87) PCT Pub. No.: WO02/20803

PCT Pub. Date: Mar. 14, 2002

(65) Prior Publication Data

US 2004/0137437 A1 Jul. 15, 2004

(30) Foreign Application Priority Data

Jul. 27, 2000 (CN) .................... PCT/CN00/00203

(51) Int. Cl.
*C12Q 1/68* (2006.01)

(52) U.S. Cl. ......................... 435/6; 435/91.1; 435/91.2

(58) Field of Classification Search ..................... None
See application file for complete search history.

(56) References Cited

U.S. PATENT DOCUMENTS 5,670,314 A 9/1997 Christman et al.
5,843,757 A 12/1998 Vogelstein et al.

OTHER PUBLICATIONS

The Sanger Centre et al. Toward a complete human genome sequence. 1998. Genome Research. 8:1097-1108.*
NCBI genebank accession data, Mar. 5, 1999.*
Frengen et al. Abstract DOE Human Genome Program Contractor-Grantee Workshop IV. Nov. 1994.*
Rodrguez et al. J. Virology vol. 63:997-1001. 1989.*

* cited by examiner

*Primary Examiner*—Teresa E. Strzelecka
*Assistant Examiner*—Heather Calamita
(74) *Attorney, Agent, or Firm*—Birch, Stewart, Kolasch & Birch, LLP

(57) ABSTRACT

The present invention provides a human source gene targeting sequence a gene vector and gene expression strategies. The invention includes the following: (1) Using a DNA sequence without important physiological function-related genes in the short arms of human group D, G chromosomes, or a DNA sequence sharing 50% or over 50% identity to the sequence selected from human D, G group chromosomes, as a targeting sequence for gene targeting and (2) Construction of a gene vector containing the targeting sequence. the nucleolus organizing region in D, G group chromosomes that is described above is used as the target site, the gene of interest is integrated into the short arms where the gene expresses actively in D,G group chromosomes of human cells. The present invention provides a novel gene targeting sequence by which the gene vector construction and gene expression strategies are realized. The gene expression strategies can be used for human gene therapy and for manufacturing protein.

2 Claims, 2 Drawing Sheets

SEQUENCE LISTING

<160> NUMBER OF SEQ ID NOS: 4

<210> SEQ ID NO 1
<211> LENGTH: 107613
<212> TYPE: DNA
<213> ORGANISM: Homo sapiens
<220> FEATURE:
<221> NAME/KEY: misc_feature
<222> LOCATION: (35922)..(35922)
<223> OTHER INFORMATION: n is a, c, g, or t
<220> FEATURE:
<221> NAME/KEY: misc_feature
<222> LOCATION: (37737)..(37737)
<223> OTHER INFORMATION: n is a, c, g, or t
<220> FEATURE:
<221> NAME/KEY: misc_feature
<222> LOCATION: (40306)..(40306)
<223> OTHER INFORMATION: n is a, c, g, or t
<220> FEATURE:
<221> NAME/KEY: misc_feature
<222> LOCATION: (55167)..(55167)
<223> OTHER INFORMATION: n is a, c, g, or t
<220> FEATURE:
<221> NAME/KEY: misc_feature
<222> LOCATION: (59042)..(59042)
<223> OTHER INFORMATION: n is a, c, g, or t
<220> FEATURE:
<221> NAME/KEY: misc_feature
<222> LOCATION: (59045)..(59045)
<223> OTHER INFORMATION: n is a, c, g, or t
<220> FEATURE:
<221> NAME/KEY: misc_feature
<222> LOCATION: (59047)..(59047)
<223> OTHER INFORMATION: n is a, c, g, or t
<220> FEATURE:
<221> NAME/KEY: misc_feature
<222> LOCATION: (61716)..(61716)
<223> OTHER INFORMATION: n is a, c, g, or t
<220> FEATURE:
<221> NAME/KEY: misc_feature
<222> LOCATION: (65477)..(65477)
<223> OTHER INFORMATION: n is a, c, g, or t
<220> FEATURE:
<221> NAME/KEY: misc_feature
<222> LOCATION: (74663)..(74663)
<223> OTHER INFORMATION: n is a, c, g, or t
<220> FEATURE:
<221> NAME/KEY: misc_feature
<222> LOCATION: (88991)..(88991)
<223> OTHER INFORMATION: n is a, c, g, or t
<220> FEATURE:
<221> NAME/KEY: misc_feature
<222> LOCATION: (92751)..(92751)
<223> OTHER INFORMATION: n is a, c, g, or t
<220> FEATURE:
<221> NAME/KEY: misc_feature
<222> LOCATION: (92783)..(92783)
<223> OTHER INFORMATION: n is a, c, g, or t
<220> FEATURE:
<221> NAME/KEY: misc_feature
<222> LOCATION: (92831)..(92831)
<223> OTHER INFORMATION: n is a, c, g, or t
<220> FEATURE:
<221> NAME/KEY: misc_feature
<222> LOCATION: (98068)..(98068)
<223> OTHER INFORMATION: n is a, c, g, or t
<220> FEATURE:
<221> NAME/KEY: misc_feature
<222> LOCATION: (102164)..(102164)
<223> OTHER INFORMATION: n is a, c, g, or t
<220> FEATURE:
<221> NAME/KEY: misc_feature
<222> LOCATION: (102863)..(102864)
<223> OTHER INFORMATION: n is a, c, g, or t
<220> FEATURE:
<221> NAME/KEY: misc_feature -continued

```
<222> LOCATION: (102895)..(102895)
<223> OTHER INFORMATION: n is a, c, g, or t
<220> FEATURE:
<221> NAME/KEY: misc_feature
<222> LOCATION: (102920)..(102920)
<223> OTHER INFORMATION: n is a, c, g, or t
<220> FEATURE:
<221> NAME/KEY: misc_feature
<222> LOCATION: (105440)..(105448)
<223> OTHER INFORMATION: n is a, c, g, or t

<400> SEQUENCE: 1

tatttgtatg tatcctggaa tacacagaat aagatcttgc atgtaagaaa cattttaata     60
gtttttaatg tgaatcaaca aacaggtaaa tgggcttttt tataatagaa tgttacaggt    120
aacataatat gcatgacata tctaataatt aaatctatta aatttcttga gtgttgaatt    180
tatcttttct tctaatgttg agaatgtata agttgaggtg acatgttgag aaaatatgtc    240
atatagaaga aaataaaatt tagaaaagat gaaaaggaaa taggaaaggt ggatacagcc    300
tgttttctaa tatcttccaa ctggaagctt agattaggat tttagattaa attttcttaa    360
atttttaaag acccaatcat tttctattaa atacctgttt ttcaggacat acattactct    420
ttcaaattct gaataaaaat tctttctcca gctgttaagt tgctggaatt ttttttccct    480
ctctctgtag taagaatgtt tcaactttca gatcaatcat catggttaac tcttgggatg    540
tgttatttta tagtaaacaa atgaaactct ttcttacata agtatttaca caaaacaaat    600
tgtcgagtaa atgctaacca gtattattaa gcatatatta tgaacacaag gttttctttt    660
aagctcatat ttgattgact ggtcatgtct cttttttgt ttgtttctcc ctccttcccc    720
tttgtttaaa aatgatttac ctcagtctaa ctttctcctt gcagcccaca tgtccttagt    780
gtctattctt tcatttcact tctgtttcta ttgtcagcat acttagttac agctttctat    840
ttagtagcta tgtgtggcct tcattcatga atcattgctc cgtaaggtgg atggttgctt    900
tgttctgtct tttttggaag gagcttaagt tatactataa tttgttttta gcttttgaca    960
cactgaatag aagcaacttg tactgtttct gatgccaacc catttaaata tagtactact   1020
aaaaactaca ttctcacatt ttttcccaca aaatgcaatt tgtacaaata tacatcatgc   1080
atagctattt tgaaaaataa tgtgattaat ttactttttt attattagtt ttattcggta   1140
atactctaaa ctacataggg tacatttttg ttctagtttg ttgtggttaa taaaagaaac   1200
taatggatat catagtattt gtataataat caactggggt tgaaaggagt aacattttga   1260
aaatatctgt ctcaccaatc ataaccatca tgccatgtga atctgtagat aagtaaatgg   1320
cagacttgag gtttgaatct acatatgagt gacttcaacg tccatacttt tcctgttaga   1380
tcatgttgta atggtgggta ttatcattat tttaacttgc cccatgttat tcttaaacct   1440
attgtgtttt tcttctagac tatttcaaaa ctatacatcc cagagagaag gattatttct   1500
ctatgatcga tagaagatgg taagctattt gaagcctgcc tattgcagta tttactgatt   1560
cttcatttgt tttttgtttt ttttttcttt tttaaacaca gtcttactag tctgcagccc   1620
aggctggagt gcagtggtgc gatcttgggt cactgcagct tccacctctt gggttcaagt   1680
gattctcctg cctcagcctc ccaactagct gagattacag gtgcgcacca ccacacctgg   1740
ctaattttttg tatttttagt agagatggag tttcacaatg ttgtccaggc tggtctcaaa   1800
cttttgacct caagtgattc ccccgcctag gcctcccaaa ctgctaggat tacaggcgtg   1860
acccaccaca ccaggccttg tggattatta ttattatttt tataaggata gagtcttgct   1920
attttgccca ggctggtctc aaactcctgg gcttctcaag ttatacttct gcctcagcct   1980
```

-continued

```
tctgagtagc tggaattata ggaacaagac actgtgttct tttatgtttt tagtactctg   2040
tagttttcta ttgttgattt aaaatgcatt ttactttttc tttcatagtg cttcctcctg   2100
ttgaagagtg ttttgacagg tatgatttca cagatttttt aaagtgatat gttaactaag   2160
tgaatagaga gaatagaaac tagtatctgt ttagtgttct actctgtgct agacaccata   2220
ttacatgctt aacatttatc atgtcatgtc atcttcacac gctttacaaa ctatttgtgc   2280
tattattgct tttttactaa taataggcaa ctctgcttta aagaggttga aatattggct   2340
catgattcca cagttaacag gtagccaacc caagattaga ccatcatcct gcctggctct   2400
caaatcactt catttgcccc taagcataga tggatagagg cctatgcagc aatgggatca   2460
cggtactgat ttacatcgga tcaattcaga aagtcacatt ttgttatata ttaactgtct   2520
ttagagtgtt atttagaagc ctggctactc caaaagtttg tccaaatatt ttgaaatggc   2580
agtggtaacc atattacttt tttttttaat catcaaagtt ttaaaggcag ttatcagtta   2640
tctgtggcca caggacccta agtttttcat aagcaagacc aggccagtcc tagaaaaata   2700
ttatcttact gtgcttggag aatatctaaa tatagtccat gttatgttaa ctatatttag   2760
catatattaa aaggatattt ctaattcatt tctctactta ctacctaccc agttaggttt   2820
tctctttcag taagtaccct gcctggttct ctgaagcttt ttcttatttt ctggattctt   2880
tttttccttt ctgtgacatt ttaataatat tttcttgatt tctttttact ttctcctctg   2940
cttttcttag ggtttatgat cttctattat agttttcatt taaggcagct aaatattccc   3000
cattttccta tagacaaaat cagaggtgca tagaatttca gaatattaag aaatcctaga   3060
gactaaacaa aatatcttct agtacttgaa tccttgctta acatcctgat caagtggttg   3120
ttcaggtgga gaacctgaaa ctcaaagaga gaaaattatt tggatacagt aaatcagaga   3180
aatgagaatt gcactcaggt ttcttagttc aaaacccagt cttcttttac atcattctgt   3240
cattgagtga ttttagtttt agaaagaggg agtggctctg gtgaacacag tggaaaagga   3300
tgagaatgga atgagctgtt gaacccaatg aaagtggata agaatggaat ttgcagggga   3360
cagacaaatt tgaagatgta gattggagat tgtcattgat ccctgcagaa gagggatcca   3420
gaagggggag cccataggaa ggtatttaga tagtgatgaa tgaaatgaag ctgtaagtac   3480
tcaggaggga gacttttcca gcagtctctc tcttgagtat ctgagtgttt atgaaggttc   3540
ttaagcttgc tggtttttgt ggacctgaat aaggcaggat ctatatagtg acaataattg   3600
gattttataa tttttaatgt tttaatcttc tgtgaggaat attcccagag tacatttgta   3660
ctttgacttt tttacactca gctttcaaac acttgcagtg tttcaggggg ctccctgtag   3720
agttctagag taaagagaat caatgggcaa tctaagtagc ttacatgctg aagatccaag   3780
actcccattt tccagtgaca cagattagtc tttgaatcag aaatagataa tgcagaagac   3840
acagtgcctt ttctaccttg ttttaggtta tcgggtttac tgcagttgag taacaaaagt   3900
tgtttcagat atcaattgga ttttcagttt agtctttagg gtagataatt tataaagaca   3960
tattattgtc tggccgtgcc attgtaatgc ctgtcactat ctgttacggg tttaagggtg   4020
agtctgcatt ggatatttca taggttggga gaggtggagg cagaaatagg taactgaaat   4080
gttttctaaa acggaagcca tatcttaatt ataccaagaa atattattta atataaggat   4140
aactgacctt cctcagactt tgttttacca tttttttgtg gaggggacat gcatgtatag   4200
actgatggtt tttgttttct tttaagaaac gaacgtgctc atttttgtca tatctttttg   4260
ctctgtaggt gtcgctacct actggatagt gttgcacagc ctgtgacaaa ggataagttt   4320
gctttggaat ctgaagtaga gtactgtctc gtgaaattaa ttttctcatt ctgaatctca   4380
```

-continued

```
tttttgtat tattttcttc taaaacttag cgattgtcta cctatcattg ttttatgtta   4440
gtattaaaac ttttattaga gataaccatt ttaaagaaat aggagggctt aattttaatt   4500
tttttttca ctttgcaaat aagaaatagt tgataaatac gttgagaggt gtgatctgaa   4560
aaaaaaaaaa tacatagtga cagaaaaatg ttgtttggga acgctttccc acaagagagg   4620
agatacaaat tttgatctag gcttatctca gtaagtgttt ttactttgag ttgtatatca   4680
tatgagtatg actaataata cctctgttta actgaatgtt tgttacatca gatgacttat   4740
tatgggaatc atgaaatcac cctgttacac acagcatata gtttcttttt atttcttgta   4800
cacctatttt aacatcatac catatttttg cagagagcta tttctttatt tttattcttg   4860
gttctatata attagactaa aataatatta gaaattgtgg aaatttaact agacatggta   4920
tcatgtgcct gtagtcccac ctattcaaga gatcaagcca ggagaatttc ttgatcccag   4980
gagtttaaga ccaagcttgg caatatagca agagcttatc tctaatttta aaaagttgtg   5040
gaatattaga aatttaaatt ctgttctcac acctgtatta gagagggttt accctgtgtt   5100
ttccaagtct tttttattaa gagtatactg taaactcttt atctaatcga agaatatgca   5160
ttttgtttaa aataacaacc tgtttgataa gcagagactc ttcatatttc tgtggtcaga   5220
ctttaacttc acaagatttt tgcattgtaa ttaaaaaaaa atccggtcgg ggtctttgta   5280
tctcattcta aatttcaaat ttcagaggct tttgtgctta gttattgaaa aaataattgt   5340
aaagctcctg cattcgtatg agccacttga agctagaaaa actatttgta tgtatcttga   5400
gtacccagaa taaggtcttg catgtaagaa acattttatt agtttttaat gtgaatcagc   5460
aaacagggaa atgggctttt tttaatggaa tgttacaggt aacataatat gcataagata   5520
tctaataatt aaatctatta aatgtcttga atgttctgaa tttatctttt cttctaatgt   5580
tgagaatcta taagttgagg tgagttatgc tgagaaaata tgtctgaatt tatcttttct   5640
tctaatgttg agaatctata agttgaggtg agttatgctg agaaaatatg tcatagaata   5700
aaatgaaaat tggaagagat ggaaaggaaa taggaaaggt ggatacagcg tgttttctaa   5760
tatcttccaa ctggaagctt agattgggaa tttagattaa attttcaaag ccccaaccat   5820
gttctattaa atacatattt ttcaggacat acattactct tttgaattct gaataaaaat   5880
tctttctcca ggtgttaagt tcctggaatt ctattgtttt tttttttcct ctctctgtca   5940
ctctctctct ctctctctct ctttgtagta agaatgtttc agctttcagg tgaatgatca   6000
tggttaactc ttgggatgtg ttattttata gtaaacaatc taaacttttt attacataag   6060
tatttacaca aaacaaattg tcgagtaaat gctaaccagc attattaggc atatattatg   6120
aacacaagct tttcttttaa gctcatattt gattgactgg tcatgtctct ttttttgttt   6180
gtttctccct ccttcccctt tgtttaaaaa tgatttacct cagtctaact ttttccttgc   6240
agaccacatg tctttagtgt ctattctttc atttcacctc tgtttctgtt gtcaggatac   6300
ttagttacac ctttctattc agtagctatg tgtggctttc attcgtgaat cattgctcca   6360
taaagtggat ggttgctttg ttctgtcttt tttggaagga gctgaagtta tacaataatt   6420
tgtttttagc ttttgacaca cagaatagaa gcaacttata ctgattctga tgctagccca   6480
tttaaatata ttactactaa aaactacatt ctcacatttt tttcccacag gaagtaattc   6540
acacaaatat atatcatgca taaatatttt gaaaactaaa gtgattaatt gacttttgat   6600
tagttttgtt cagtaatact ctaaattacg tatgagtaaa tttttgtccc agtttgttgt   6660
ggttaataaa agaaactaat ggatatcata gtatttgtat aataatcaac cggggttgaa   6720
```

-continued

```
aggagtaaca ttttgagaat atctgtatca ccaatcataa tcatcatctc atgtgaatct   6780
gtagataagt aaatggcaga cttgaggttt gaatctacat atgagtgact tcaaagtcta   6840
tcctttttgt gttagatcat gtagtaatgg tggcaattat cattatttta acttgctgaa   6900
tgttgttctt aaacctattg tgtctttctt ctagactatt tcagaaccat actttacgaa   6960
cagaaggact atttctcaac aatctgcaga aaagtgtaag ctatttgaaa cctgactatt   7020
gtattatcta ctgattcttt ttttttttc tttcttattt ttttgtagac agagtgttac   7080
tcactgttgc cctggctgga gtgcagtggc atgatcttgg ctcactgcaa cttccacctc   7140
ctgggttcaa gtgattctcc tgcctcagcc tcctgagtag ctgggattac aggtgtgcac   7200
caccacacct ggctattttt gtatttttgg tagagatgga atttcaccat gttggccagg   7260
ctggtcttga acacctgacc tcttgtatga tctgcctgca tgggcccaca aaagtgctgg   7320
gattaaagtt gtgagccccc acacccggtt cttatttatt gattcttaat tacacgcatt   7380
tcatctactc ttgacttttt ttttactgta gtagatgctg catgtggcat tgaaaaaaca   7440
aaatatggaa cctttttttg aagaccaaaa tgttgataag gtaaatgaag atgtggttaa   7500
aagccaacat agaataatca gagtcgagtc ctgttcacca actcactctt atctgttaat   7560
gatctctagt tttacaatgg taaattgttt tatttggaaa atatttttcc catgctttat   7620
tcacttgcca tctccctgtc tttataacga tgacaaggat cctataaggg aatggaagtt   7680
ctccaggtaa taatagaaaa gaagtgtaac aacaagggaa atatatgcat gggaccagga   7740
ttcctaaaag gtcatgggag taaatgattg ttaggtttgc cattagggaa ggaaagaagt   7800
agaaagcaac ctgaaagaac agctccacaa atacaaaggt gaagaggggga aagaagtaag   7860
aatacagagt tgaataagag tgtcaagatg acaaagatta gtataaaaca cctcaaaaac   7920
ggtgaattta aatgacagta gaatgtctcc atatcatatt atagaattat tttaaatata   7980
gattaggaaa agaaagccaa gtaattaaaa taatgctcag attcttctga gtgacttacg   8040
ggtgatttta ataaaggatt ggaagaaaat ttatgggtga ctatatttaa cattctgttt   8100
aacatttaaa aatagccagg agagaataac ttgaatattt ctagtttaaa taaaacatac   8160
atatttaagg taatgtgtat ctctgttacc ctcattagat tatatagatg gaacaaatca   8220
tcacacgtac actgaaaata tatgcatcta tttattaatt taaaaattct aaatggaaag   8280
aaaatttaat cctaactttt taaaatttca gtaaagtgat gtctcatatt ttatctagtg   8340
aatattgtgt tcatagatca tgcaaagtaa aatgtgtttt aggctatatc agattttgaa   8400
tgaatcatta atttttgact cctgttaaaa gttttttaaa gtaatatttg gtatattccc   8460
aagttgctta actaatttat ttcactttta catcatcttg gcagctgttt tagccttttt   8520
ttgataatag agaaaataaa taagtaatta aataatagaa aataaaaaat aataaaaatt   8580
aataaaaaaa ttaataaaaa ttaaaatttc tggttaattt ttttttttg agagggagta   8640
tcgctctgtc gcccaggctg gagggtggtg ggtgatctcg gctcactgta aggtccacct   8700
cccgggttca tgccattctc ctgcctcaac ctcatgagta gctgggacta taggtgtccg   8760
ccatcacgcc cggctaattt ttaaatattt ttagcggaga cggggtttca ctgtgttagc   8820
caggatggtc tcgatctcct aacctcatga tctgcctgcc tcggcctccc aaagtgctgg   8880
gattacaggc gtgagccacc acacctagcc atttctggtt aatattaaag gaggtttcta   8940
atttatgttc attgaatgag aaaaaatatc tttttaacct ggaaccctct taaagaaata   9000
aattattact tatttctgga gctagtctga ctgaccttgt gctgataacc tctgtactta   9060
agaacataca tgtgatgaat gcagtcaaca ctcatgattg ttttctaaac aaagtaccta   9120
```

-continued

```
ttttgataga atcgtaagga aagaaatatt gccaacagta cacagaatta tctctggaat   9180
attacttttt acttttaaaa ctatctcctg cagttgggac gtttttttatt attctctgga   9240
agcattatta actttagtat ttatagttat accttgcaca taaatttatt cagctctaaa   9300
actcaggaat ccttttgact tgatgtttaa aataaatttc ttctctcttc atgtgagtat   9360
tgagtcatga gtgacaggca tagtgtattt gaagacaagt aagtcttcag cttgcatagt   9420
catatgatta ttttacttga tcctttctct gatttttaac tattatcttt atggcataag   9480
taggcaatta gagctattag tatatcattt caggagaatc agaaaaccat atgaacttta   9540
aaatagattt tgcatttctc tcttatatgt tagaagtact taaaatgcct tataattcta   9600
taatagaata aacatttgtg caagttaaaa acttttaaga tgattttttg aaaatgagct   9660
ttcttaggac accttgactt actggtttag ataactgttt tcattaagtt caaaaatgca   9720
gatgaccata atattccaga aataaatatc tgcatacatt tagaaaatat attttatatc   9780
ttttaatcca gtatagaaat atataattga aattttgaat cacatgtttt gttttctttt   9840
tattttcaaa acttcagggt tctacatagg tttaaattat tgaatcctac cagtttagta   9900
tactttacaa atgttgacct tctcaacaac atatggtttt tttgagtaag gtcatctatt   9960
tctactccaa atgtatttac ccagatcagt cttctaagtc ccctttgtgc ctcaaattta  10020
ataggtctca aactgccttc cagattcttt cctgactctt tgtaatccat gctgtcatct  10080
cacttcccaa ttttagtaaa taacaccaag gaggtagtaa tgaaacattg aagcagaaaa  10140
actgcactcc aggtttccct cacatagcca atccagtgac tcaccaattt ttgtattttc  10200
tacctttaac cacttctcat atcttattac tgtaatacac tgtcggccct atacttttgg  10260
aatgttcgtt tttgtttctt tcttctcccc atgtttatct atctatatat gtctttcagg  10320
gtgacctttc ttaaacatgt ttactttgat ctaagtcatc tgtttatggc tggaccctca  10380
ttacatgaaa caaacattta cattctagca taacacttat tttgtggttt ggcctgtttc  10440
tcccatttta tctctccact ccactttctc tgtctgtgtc caagttttac cacgttattg  10500
tggtatttct tattggctat gctgtttcat gctttatttt tttgcacatg ctgccctcac  10560
tagaaacact tcacactctt actcttccct tgtctatttt aaaaatagaa ccctaaattt  10620
gcagtttctc agaagcttcc caagtagaat tgttattgcc tttgtgctat cactgtattt  10680
tattgacttg aattgtagaa ataatgaatt gtgtctttct gcttttgttt gtttttataa  10740
atttcttttt tcacttgata aataaataaa attggtattt tattcatatt atcagatttt  10800
ccagtataga tcttatgaat ttatagacac ggaaaatgtt tcttgaatta ctgactgatt  10860
aagtagtaaa tatgacattt tctgaagatt tctttttttt ttttttaata ggaaagaaaa  10920
gcactaccag caactggaca aaaagcaaat ggtattggta ttataaaaag tgctccatga  10980
gagcaatcaa ataatgataa tgttgtattt tgtgtacaat aaaagatggt gaggtagtga  11040
atatagctga ataattttct atgctttaat aatataattt ttgaaaataa atataactaa  11100
tttaaatata atttaaaata aatttaaaat taaattaatt gttaaattac attaaattat  11160
aagcctaatt ttaattaaat tatagttata atttattaat tttaatagta aatataattt  11220
aatttaaaca tactttttct taaaactttg gtgaacactt aaacttgtag atcaaaatat  11280
aatattcatt gttgagaaat ggacattagt atatttacaa aaaaatgtga ggtgggattg  11340
tgtaaattaa gaaagcagct ggctaggtat ttggaggttt ctgatgagga aacttgaggg  11400
aactcacttt atgtagactc agtatattcc cactcaaaga gaagattaaa tgattgctgc  11460
```

-continued

```
tttggagctt actggaggca gagggtagaa gaacgacagg aaaccacaga aactcatttc  11520
ttctctctat aggggttaca catcaatgat atgtgcttca ttcatgtttg ttagtgaact  11580
gggatgcact tggatatcaa aacattggca gttttcttta aaacaatgct gtttttgatg  11640
aaatagccat tgtataaaag tacctcagag gctgctatgc tatagcatat caaactgact  11700
agaaaaaaaa caaacgagaa atttatttct ttagtactaa aagtgtaact gtcaataatc  11760
atggcaaata ttttgatatg taaaagttga ttaatccagg cgcagtgact cacggctgta  11820
atcccagcac attgggaggc tgaggcggga ggatcacgag gtcaggagat ggagaccatc  11880
ctggctaaca tggtgaaacc ccatctctac taaaaataca aaaaattagc caggcgtggt  11940
ggcatgtgcc tgtagtccca gctactaggg agcctgaggc aggagaatca cttgaacccg  12000
ggcggcggag gttgctgtga gccgagattg tgccactgca ctccagccta ggtaacagag  12060
caagactcca tgtcaaaaaa gaaagttgat tagtatgaaa aaaaagtcaa tggtgattca  12120
gagatttttg gttacatttt gtaaatgaaa atctgagtac tcattagtta tttgatgtgt  12180
aacatatact ttttttgcat aagggaatga aaagatggca agagaactaa agttgagaat  12240
ccagaagttg aaaatatcag aagtcttcat gactgtggat aacatgagta tttttagaaa  12300
cgatttttct ccaagtagat atctaaacta atgattgaga gcatttcctg ccagcagaag  12360
cgaatgatac attttctttt cttttctttt tttttgagac cgagtctcgc tctgtcaccc  12420
aggcttgaat gcagttgcgg gatctcagct cactgccaac tccgcctccc ggggttcacg  12480
ccattctcct gcctcagcct cctgagtagc tgggactaca ggcgcctgcc accaagccca  12540
gctactttta tgcattttta gtagagatgg ggtttcacgg tgttagccag gatggtatcg  12600
atctgctgac ttcgtgatct gcccgcctcg gcctcccaaa gtgctgggat tacaggcgtg  12660
agccaccgcg cccggccgcg aataatacat tttcatgctc tctcattgca acttcatagt  12720
ttctaacatt tattcttctg gggtccgctt tggttctctc atttgacgtc actttttttg  12780
gcttcatcca gcagattcgc attcgtagaa atacttttct atgttacttg tagtcatgtg  12840
aaacctaatc tcacccttgc aatctggact gcatgtttta tagaatctat attgtgattt  12900
ttcatgtgta tattcctgtc atgtttgtgt gttaaccaaa acaagagcaa agcaacccaa  12960
agcctaatgg gtaacaattt caagggcaag gacgaagatt tcagctggat acaaacactg  13020
catgattgat ggtaggctat gtcatatttc cctgtagtca attttgtgtt ccttttgttt  13080
tttagtgtct cctgagcaac cgcctttatt cacggtaagc atattttctt taattattaa  13140
caaaatgctc tgtgatatat acatgatata ttaatcatta tgttgtcaaa cccattcagc  13200
atacggtgaa agacagagat cacatttcaa ctagattctt aggaagtatg gattcaccaa  13260
cttccagtga aggtaaattt gccactacaa atttcattct agaaaatgta gatgaaaata  13320
ttgaaaatgc tcatagtttt ttgattccca ctttttatcc aaatgagatg gaaggatttg  13380
atgtaaatat gctgatgttc ttgttaatat ctttgtttat aaaatgatat ttaaggcata  13440
aggcggacat tttacaccat gagctctagc ccaaatgctt ttcctttaaa gttgtcatca  13500
tctgaagatc ccagttttga attcctgtgc atgttaggga tttgaggagg tgtattttga  13560
cactaagtat tttcagtgct tcaaaattga ttggaatact cttctctctt cttcatctag  13620
agaaaagcta tacctgctga cgttacaatt gttttagaac ttcaactcct ttatgtcagt  13680
gttgttacat tgagaatctt tacttaatca catcttctga ttaccagatt gagtttctgc  13740
atgtgtatgt gtgtgtgcat ctcagattaa gaatgaataa aatgattaat cattcttttg  13800
taactctttg gtagatacag tgttttaaaa caatgattct gagctgtttt ggccttagaa  13860
```

-continued

```
tattttcttc tactacaatt tattgcctac aggtagccaa cagcctgaat taacgttttt  13920
tacttttaag tcactgcaat gcacattaaa aatactttac aagatacttg cactttcata  13980
ggtaatatgt agaatctgtt tccaagtatc aagtcttcta tacgatttca cacagcgtac  14040
ataatagctg caactcggct tttctaatca gtggtatata ttttggatct atccaggttg  14100
acacaatttg ttcatctttg atttgttgta tggtcttgtg gtatgccatt ttatgactgc  14160
accacaatta attaaagtct cttcatgctg atacaaaatg aacataaata tgatgacatg  14220
ccaacataga tttgcttatg tggttgtctt tattgatttg tactatataa gaaattaaat  14280
agaagtattt cagataccct gagtatagct gtatacactg ccatagctgt attgactaca  14340
ttcattaccc cttagagcca tgtttttcca tcatattatg actctgaaaa gccctagtgt  14400
atgcttttca gagaatgaca ttggaaagaa gaaacggcca aagtatcatt tggtaccttg  14460
gcttccttac atagatgttg aactccaaga atgatcaaat cacagtttag aacccctttg  14520
ttggccctat aaagggtttc tggatatcaa atgataaata gtctccagat gaagaaatgc  14580
tctataacgc cccaccgctg tgttttccta tattttgtcc ttttctgaaa actttaaata  14640
cacgaatttt tggtagaaat gaaaatcttt ctgttttata tatttgtttc tgtccatggc  14700
actctgatat ctttgaatct agtaaggata tagccttgtc ttatttatac cagcaagcag  14760
tgttgtcact taatgctctc atttttcacg taaatgactg acattttccc aagtcttcgc  14820
aagtgatttt tgaagacgtt gctgcattaa gcagagacta tgtcattgta attgcagaag  14880
tttttaaatt aaatatgttt aataaaattt tagagcctgt ttctgtggaa cacgtaacac  14940
ataatggtgg tgtaatgtgt atttaaccat aaattagctt cacaaaaatt tgtgtactta  15000
aaagtgttta tatccaaaga aattcttatt tactgctcag taatctcttg tgtagaagaa  15060
aatatgtaac atagtttgct gagtctttga taataacccc cagtgtaaaa taaagctgta  15120
aagatgaaat gagagttgat actcaatgaa actgatgtga gtgaatacaa actatgaaac  15180
tgtgtctagg ggagagagga ggacatgggg ctgctattgt gaagaaggaa tttgtacaag  15240
ttagtccatt ttctgtaact tttatattct aataaaggaa aaccatatct tcatatttat  15300
aaaaatggga ttttactggt ttgatcacag gggttgtgag aataatgaag aacaaaatgt  15360
ggaaggcaaa gaatgaagac cagatagtga gattagattt atcaacaaaa aagagtgcaa  15420
gtggggtggg atggtgtaaa taaagacagc agctggctag gtatttgggg gtttctgatg  15480
aggaaacctg agaaaactca ctttatgtgg acctggtata ttcgcagtcg aacagaatat  15540
tcgattattg ttgcttcaga gcttaatgga agcagaggtg gaagaatgag taaaccacag  15600
ggactcaatt cttctctctg taggggtaac acatcgacac taggataggt gcttcatgtt  15660
agcaaaatgc gatgcagtgc atgtcaaact gtggaagcaa aacaatcaag aaataaattt  15720
cttaagtatt atttatttat ttatcgttat tatactttaa gttttagggt acatgtgcac  15780
aacgtgcagg tttgttaaaa tgtaactgtc aatgatcatg gcaaatattt tgatatataa  15840
aaggtgatta acatgaaaaa agcctctgat atttcaaata ttttggttag atttgtttta  15900
tgggaatcta attacatatt aggtatttgg agtgtaatgt atacatttct tgcataagtg  15960
aatgaagaga tggcaggagg gctaaagttg agaatccagg aaatggaaaa acaccagaag  16020
tctgcatgac tgtggacaac atgagtattt ttgttaacta tgcttctgta tgtagatatc  16080
tgaactaatg aactgagaat acatcctgca agcagaaggg aatgatacat tttaatgaaa  16140
ctgatagttt ttaagttaga ggacaaaatg aagaacacga aaactattgt agtattgtag  16200
```

-continued

```
tataaatggt tcttgggtga tttcttcagg gtacaccata gcgttctacc atgggctttg  16260
acatttatcc tcctggggtc ctttcatttg acatcacatt ttttggcttc agttaagaga  16320
atcacattgg tagaagtact tccttgtgtt agttgtagtc atgtgaaacc taatctctct  16380
cttgaaatct ggactacatg ttttatgaaa acttaattat gtgtcccttt tgctttgtag  16440
aatcttctga gcgacctcct ttatccacag taaacaaata tattttcgtt tttaattaac  16500
aaaatgcttt gtgatatata tatgatatat taatcaatta atcattatgt tgtaaaaccc  16560
attcagctta ctctgaaaga ggcagatccc agttcaaaag tagccatgag aaggaaggat  16620
tcaccacctc caggaaaagg taaatttgcc aatacaaatt tcatctggaa agaaggacat  16680
gaatatattg gaaatgttca tggtcttctg attcttattt cttttacccc aataagatag  16740
aaggatttga tctaaatgat gctgatgctg ttgttagtgt ctatgattat aaaatgatat  16800
ttagaagaac aaggaaaaga aatgtttaaa atgtgagctc tagctcagat gcttttcctt  16860
ttaggttgtg ataaatatcc aatgtggaat ttgtatgcat gttaggggtt caaggaggtg  16920
aattttgaaa ctataaatat ttttcagtgt ttcaatttct ggttgcaata ctgtccttta  16980
cctagagaaa agctatacca gctgacatta caattgtgtt agaacttcaa cttctttatg  17040
tcggtgttgc cacactgaga accttcaaat cctcacccag tcacatgctc tgattaccag  17100
cttttgaatt tctgcatgtg tatgtgcgtg tgtgcttttg tttgtgagtt tgggtgtgtg  17160
tgatacctct gattctggaa aatgaataaa gtcattaatc attttttggt gactctttgg  17220
tagatacagg gttttaaagc aatgattctg agctgtttta gccttagaat cttttctact  17280
actacaattc attgcctaca ggtaaccaac aacctgaatt aatgttggtt cgtttgtttt  17340
gtattatacc ataagttcag ggatacatgt gaagaacatg caggtttttt acataggcat  17400
acatgtgcca tggtggttta ctgtacccat caacccatca gctacattag gtatttctac  17460
taatactatc cctcccctag gaccccaacc ccctgacagg ccccggtgtg tgatgttcgc  17520
ctccctgtgt ccatgtgttc tcattgttca actcccactt acgagtgaga aaatgtggtg  17580
tttggttttc ttttcctgtg ttagtttgct gagaatgatg gtttcaggct tcatccatgt  17640
ctttgcaaag gacgtgaact catccttttt tatggctgca tagtattcca tgatgtgtat  17700
atgccacatt ttctttatcc agcctatcac tgatgggcat gcgggttggg tccaagtctt  17760
tgctattgtg aatagtgctg caatagacat acatgtgcat gtgtctttag agtagaatta  17820
tttttaatct ttggggtatg tattcagtaa tgggattgct gggtcaaata gtatttcttg  17880
ttctagatcc ttgaagaatc accacactgt cttccacagt ggttgaaata attgacactc  17940
ccaccaacaa tataaaagtg ttcctatttc tccacatcct ctccagcatc tgttgtttcc  18000
tgacttttta atgatcaccg ttctaactgg cgtgagatgg tatctcattg tggttttgat  18060
ttgcatttct ctaatgttca gtgatgatga gccttttttt catatgttta ctggctgaat  18120
agatgtcttc ctttgagcat atccttcacc cacttttga tgaggttgtc tgttcttttc  18180
tcataaattt gtttaagttc cttttagatt ctggatatta gccttttgtc agatggagag  18240
attgcaaaca ttttctcctg ttctgtgggt tgcctgttca ctctgataat ggtattggaa  18300
gttctggcca gggcaatcag acaagaggaa aaaataaagg gtattcaaat aggaaaaaag  18360
gaagtcaaat tgtctctgca gatgatatga ttgtatattt aggaaaccaa aacgtctcag  18420
ccccaaatct ccttcagctg ataagcaaca tcagcaaagt ctcaggatac aaaatcagtg  18480
tgcaaaaatc gcaatcattc ctatacaacg ataaaagaca aacagccaaa tcatgagtga  18540
atgtccattc acagttgcta caaagagaat aaaataccta ggaatacaac tcacaaggga  18600
```

-continued

```
tgggaaagac ctcttcaaga actacaaacc actgctcaag gatataagag aggacacaaa  18660
caaatggaaa aacattccat gctcatggat aggaagaagc aatatcatga aaatgtctat  18720
actgcccaaa gtaatttata ggttcagtgc tatagactac cattgacttt cttcacagaa  18780
ttagaaaaaa actactggaa atttcatatg gaaccaaaaa agagctcata tagccgagac  18840
aattgtaacc aaaaagaaca gagctggagg catcacgctg tctgacttca aactatacta  18900
caaggctata gtaatgaaaa caacatggta caggtaccaa aacagggata tagaccaatg  18960
gaacagaaca gaggcctcag aagtaacacc atacatctac aaccatatga tctttgacag  19020
acctgacaaa aaataatcaa tggggaaaag attacctatt taataaatgg tgttgggaaa  19080
actggctagc cttatgcagg aaactgaaac tggaccactt ccttacacct tatacaaaaa  19140
ttaactcaag ataaattaaa gacttaaatg tttaagtaag acctaaaacc ataataaccc  19200
tagaagacaa cctaggcaat accattcagg acattggcat gggcaaagac ttcatgacta  19260
aaacaccaaa agcagtggca acaaaagcca aaattgacaa acgggatcta attcaactaa  19320
ggaacttgtg cagctttatt tggaagtgtg caatgaggta cgtctgagtt tcaaaaatga  19380
agaaagtaag tagtcatgct ttcctgactc tttggtagac agccttttaa gacggtgatt  19440
ctgagctgtt actgttttgg gttttctata atactaaagc ttactgccaa aatgtaacca  19500
agagcttgaa ttaagtaaaa agaaatcacc caaatgcaca ttaaaaacct cttacaacat  19560
atgtgcacat tcatagataa catgtagaac ttgattttgt gtattaaaaa cttgtagaaa  19620
agttcaggca gtgcacttat tgaatgcaac ttggtctttg taaaatcagt gatatatatt  19680
tcagatctat ccaccttgac ccagtgaggt atttcttgat ttattgtatg atctcatgat  19740
atgccatgtg atgactacag catattatgc tctcttcatg ctgataccat atggacttaa  19800
atatgatgac ataccagcat ggatatgctt acgtggttgg ttttattgat ttgtactata  19860
ttagaaatga aacagaagta ttggaaatcc tagcaagcat agctgtatct ctcccatggc  19920
tgtgttaatt gcaactgttt ccccccttaaa gcatgtctgt ttgacatgtc ctaactctga  19980
gaaaatccag tgtgtgcttt tcagagaata gcagtaagga gtggaaatgg ccaatggtca  20040
aagtgttact tgtcctcttg gctccccttc atgaatgtta aactctaaac tactcaggtc  20100
acaatttaga acccctttgt tgatccctat agagtgttcc cagatatcaa atgacaaata  20160
ggtctttgat gaagaaacac cctgtaaagc catattgctc tggtttttgt gtgtgagtgt  20220
gtgtgtgtgt atgtgtgtgt attttcttct cttttgaaaa ctgtaaatag aggaattttc  20280
attacaaatg aaaatgtttc tgttccatat ttatttcctg tctaatgtac tttgctcttc  20340
ctggatctag taaggatctc agcttgtctt ttttatacct gcaaaaaatt acatcaagct  20400
tcatttttca tgtcaattac tgacatattt tcaagccttc acaagttatt tctgaagatt  20460
tggtgcatca aggagagact gtcattgtag ttaaagaagt ttttaaatag gttatattca  20520
ataaaatttc agagcttgtt tctctggaaa gcatagacat agtggtgtta tgggtagtta  20580
aacataaaat agctccacaa agtgttgtgt acataaaagt gttcatatcc tggaaaattc  20640
tactttattg ctcaatactg tctgctggag aggaaaatag gtaagatagg ctgctgagcc  20700
tatgataata actcataata tgaggtgaaa gcatagagac aaaatgagag atgatagata  20760
ctcaaatgga tgtgagtgaa gaacagctgt gaacgtgtct atgggagata ggaggccatg  20820
gggctgcttt tgtgaagaag gaatttgtac acgttagtca agtgtcttga cacatttaac  20880
attttaataa agctaaacct tatcttcaga tgtgtcagaa tgggattgta cagatgtcac  20940
```

-continued

```
attacagtgg tggtgaaaat aatgaagaaa cgaatgtaag ggtcaaagaa tcaagtccac  21000
caatatggat attagattta tgaatgaaaa agagtgtatg tcaaattggg caggtgtaaa  21060
caaagaaagc agctagctag gtaatttgga ggtttctgat gaggagattt gtgggaagtc  21120
acttaatgga aagcagaggt tagaaggatg agggtgaccc acaggatctc atttcttctc  21180
cctagaagtt ttgcacatca atgatacatg cttcattcac atcagttttt cttttttgga  21240
aagctgtgtt tgctggtgta gttattttgt aaaagaacct gagagacccc tatggtatat  21300
catgtgaaac tagatttaga aaaaaggaat caaataatgc atttttagag tactaaacag  21360
ataactgcca ataatggtga caatcatgac atatgtatat atatgtatta tgtcgtattg  21420
gttggttatt tataagaaaa gaagtctcta gtgatttaga aactttagtt tattttcata  21480
ggaatctgat tacacattat ttcactgatg tgtatgtttt tgcaaaagtg gacgaagaga  21540
cggtgagaag gccgaactgc tgaatccagg aaatgtaaaa acatcaggag tcttcatgag  21600
cataaacaaa atgatttttt aaattataac tcttagatta agtgaactca cttcagatgc  21660
attcagaata tttgcataaa ggatgatttg atttttggct gttccaggaa ctactggaag  21720
caggaaacag tgatagaatt gggataaacc acagtgactc attattcctc tttgttacta  21780
ttgggcacca gaggtatatg ttttgttgat attggttatt caaatgagat aaacgtgaat  21840
atgcatacat tggctttgtt tttcaaggag gtattggata aaatagcaac ttaataaaaa  21900
ttctctagag aataacatga taatttaacc agactatttt agaagtgaaa ataatgttga  21960
attcattact tgactcccaa atggttattt tcaaggaata ttggcgtgat ttccagatgt  22020
aaaagcttat tcatatctaa tgcttgtagc aattttattt tgtataagta tgtcaaattt  22080
ggtaatttat tatacttttt gatgaagttt atacattata ccttgttgcc atgagtggat  22140
gaagatttcg gaaggctaaa ctagaagatg caagagatgt aggcacatta ttacaccata  22200
tgggtatgag aaataatgaa cattacatac tataattcac caaacatata tccaagctga  22260
ttaaattagg acacttccac tgaagtgatg tgaagtgtac attcaactaa agtgtcatta  22320
taattgtgta ccttctcact gattggtcaa gttaaagaac atgatgaatg tttgcagtaa  22380
aatgttccaa atcattctga tatcttgcat gaaagacacg cgggtgcatg tatcacctgc  22440
tttgacgttg attcccaggt gtatgagttg aactctgatt ttagatcaca tttgtcctca  22500
acactcagca tatccacatt gatattgaca tggctttatt ttagttctag acatatggag  22560
aaagttatat cacatttgaa attgtcagta tatatttctt gaagcctgta ttactatttt  22620
cttcagtgta tttccttcat gtttagtccc aagaaacaaa gtataaaata tcaaagccta  22680
cagtaataca ggcaggagta taaaacttga tgctaacatg ctatccatgc attaatgtat  22740
ggataacatt atcatattta catatgattg attatgtaac ccttttgctt ttcagtgtct  22800
tctcagaaac aaccagctga gaaggtaatt aaagtctcat ttatctgttg aattattaac  22860
tgtatagtct atgaaaccta ctttacgtat tattttgttt tcaaatccca ttcaggctac  22920
aagtaatgag aaatattctg tttcaaatac agccacagaa ataaaggggg gaccaatatc  22980
tgggacaggt aattttgcaa aacacatcta atgtcacgtt caatcaagat agaagagaac  23040
gtcccttctc caaataaatc agtggagagt tcatctaagc tgcacgttct gattcagtat  23100
gcctgagatt gttcatttgt agtgagttct caggtgaccc tgatgctgct ggtccttggc  23160
catgatctga gtagtaagat tatagacttc cctacattga aattgggaag aagaaccatt  23220
ggagagcagt tcaacacata ccaggctaag ggagcagcat aattttgctt taattctaca  23280
gcatgtttcc atcaagaggg gaaagagaac gagatgaagt aatagatatt ataggcatca  23340
```

-continued

```
tatcgtattg ttataaacag agggacaagt gatctgaata actccacaaa cactgtagaa  23400
tgagaactaa gaagaccact gatggagcaa ttattttcct caaggaagag ggattgtgag  23460
gcaggaagga ggaaaaagaa gaaagtattt atgtaatttt ggggtttctg ctgaggaaac  23520
ctgagtgaac tcatttcaga tgcatttgga atatttgcat taaagaagat ttgattttgg  23580
ctgctccaag aaatactgga agcaggaaac aatgctagaa tcgggataaa ccacagtgac  23640
tcattactcc tctttgttac tattaggcat cagagataca tgttttgttg actttaatta  23700
taaaaatgag ataaacttgc atatgaatac attggcttcc ttgttcaagg agctacctct  23760
tggataaaat agctatttca caaaacttct ttagagaata acatgataat cccaacaagg  23820
ctattttaga aacaaaaatg atgttgaatt ctaattaact cctaaagtgg tcattttcaa  23880
tgaatactgg ggtgatttct gaatgtaaaa cttatcaata tctaatgctt gtagcagttt  23940
tactttgtag aagtatgtta acatcggtaa ttgatgatat ttttattgag gctaatatat  24000
tatcctttgg tgccatgagt ggatgaagaa actttcagaa ggctaaacta gtggatacaa  24060
gaaacttagg caaattatta caccacatgg gtgtgagaaa taatgaatat tatctactag  24120
gtttcaggaa acatatgtcc aaggtgatca acttaggaca cttccactga agagacatga  24180
aatgtaaatt taactgaatt gtcattgtaa ttgtgtatgt tctacttatt gggcaagtta  24240
aagggcacga tgaacgtttg tagtataatg gtgtaaatcc ttctaatttc ttgcaagaaa  24300
gacatactgg gtcatgtacc acctgctttg acattgattc tcaggtgtgt gagttactcc  24360
tctgatttgt cctcatcact cagcatatcc acattgatat tgacacggtt ttattttagt  24420
tttagacata tcacgaatca taccatgttt gaaattgtaa gggtatattt tgtgaagcct  24480
gtattccttt tttttcagtg tatttctgtc ttgttccagt ctccagacaa aaagtaggaa  24540
acatcaaagc ctacactagt gcaggcagga agatacagct tgataataac actgcatgat  24600
atatggataa atttatcata tgtacatatg agtgattatg tatccctttt gcttttcagt  24660
gtcttctcag aaacaaccag ctgagaaggt aaactctcct ttatattttt tattagtaac  24720
tgtatggtct ttgaaacatt ctttatatat tgataatttg ctccaaatta ctttcaggct  24780
acaagtgaca agacagattc tgttttgaat atagctacag aaataaagga tgctttaaag  24840
ttcatatgga accaaaaaag agcctgcatc accaagtcaa tcctaagcca aaagaacaaa  24900
gctgcaggca tcacactacc tgacttcaaa ctatactaca aggctacagt aaccaaaaca  24960
gcatggtact ggtaccaaaa cagagatata gatcaatgga acagaacaga gccctcagaa  25020
ataacaccgc atatctacaa ctatctgatc tttgacaaac ctgagaaaaa caagcaatgg  25080
ggaaaggatt ccctatttaa taaatggtgc tgggaaaact ggctagccat atggagaaag  25140
ctgaaactgg atcctttcct tacaccttat acaaaaatca attcaagatg gattaaagac  25200
ttaaacatta gacctaaaag cataaaaacc ctagaagaaa acctaggcaa taccattcag  25260
gacataggca tgggcaagga cttcatgtct aaaacacaaa aagcaatggc aacaaaagac  25320
aaaattgaca aatgggatct aattaaacta aagagcttct gcacagcaag agaaactacc  25380
atcagagtga acaggcaacc tacaaaatgg gagaaaattt tcgcaaccta ctcattgaca  25440
aagggctaat atccagaatc tacaatgaac tgaaacaaat ttacaagaaa aaaacaaaca  25500
accccatcaa aaagtgggca aaggacatga acagacactt ctcaaaagaa gacatttatg  25560
cagccaaaaa acacatgaaa aaatgctcat catcactggc catcagagaa atgcaaatca  25620
aaaccacaga gataccatct caccccagtt agaatggcaa tcattaaaaa gtcaggaaac  25680
```

-continued

```
aacaggtgct ggagaggatg tggagaaata ggaacatttt tacactgttg ttgggactgt  25740
aaactagttc aaccattgtg gaagtcagtg tggcgattcc tcagggatct agaactagaa  25800
ataccatttg acccagcaat cccattactg ggtatatacc caaaggacta taaatcatgc  25860
tgctataaag acacatgcac gtgtatgttt attgcggcac tattcacaat agcaaagact  25920
tggaaccaac ccaaatgtcc aacaatgata gactggatta agaaaatgtg gcacatatac  25980
accatggaat actatgcagc cataaaaaat gatgagttca tgtcctttgt agggacatgg  26040
atgaaattgg aaatcatcat tctcagtaaa ctatcgcaag aacaaaaaac caaacaccgc  26100
atattctcac tcataggtgg gaattgaaca atgatatcac atggacacag gaaggggaac  26160
atcacactct ggggactgtg gtggggtggg aggagggggg agggatagct ttgggagata  26220
tacctattgc tagatgatga gttagtgtgc agcgcaccag catggcacat gtatacatat  26280
gtaactaacc tgcacaatgt gcacatgtac cctaaaactt taataataaa agaaagaaaa  26340
agaaaaaaaa ttaaatatgg tactgaagca aataaaccac taatagctga gaaaaataaa  26400
taaaaataaa ttgttgatgt aaaaaaaaaa ggatgcacta caatgtggga caggtaattt  26460
tgcaaaacac atttaatgtc attttcaatc atttagaaaa gaacttctct tccccgaata  26520
aatcagcggg gcggggctcg tcgaagctgc actttctgat tcagcagacc tgagattctt  26580
catttgtaat aaattctcgg gtgatgctga tgctgctgat ctggaacatg atcttcgcag  26640
taatattata cacttcccca cattgaaatt gggaagaaga aacattggag agcagatcaa  26700
gacataaggg gatcagggga cagcataatt ttgctttaat tctacagcat gttttcacca  26760
agggtggaag gagaatgagt tgaagtatag attttacaga cgtcacatcg tattgctaaa  26820
aacagacgga aaagttattg taataaccag taaaattgtg gaacgagaac caatgagacc  26880
actgatgtag caattatttt actctagcaa gagggattgt gaggcaggaa ggagggaaaa  26940
gaagaagtta tttatgtaat tttggggttt ctgctgagga aacctgagtc aactcacttc  27000
agatgcattt agcatgttta cacaaaaagg attttatttt ggcagctcca ggaactactg  27060
gatgaagcaa agaaagctag aattgggata aaccacattg actaattact tctcttcgtt  27120
actattaggc ataagacata tcttttgttg atttttgtta taaaaattag ataaacttga  27180
atatcaatac attggcttca ttcatccaag tgctatctca tggctaaaat agctatttaa  27240
tgaatatgat ttagaggata gcataatcct cctaatgaga caaaaacaac tataatgttg  27300
agttcatcaa ctgactctta aaatggttca caggcgtgaa ccaccgtgcc tggcctaaaa  27360
atataaggtt ttattcagat gtttctactt ttacattttg atactctgaa gtttccaatt  27420
tggaatttca atagttttta gagatttaaa gagatcaatt ttgacactgt aaaatatttg  27480
ttttgcttta aaagtcaatt caaattatgg ccactttggt ctcatatatt gtgaggctgg  27540
tttgttatta ggggcataaa gacttaggat tgttatgttt tgttgattaa ctgaaccttt  27600
tactattgtg acatgacatt tgttatttat tgatagaatt tttttttttt ttgctatgaa  27660
atctactttg ttattaatac agccactcct gctctgctgc ctttggcaac tgttagcatg  27720
tatctttttc catccttaca accaatttgt gtctttacat ttaaagtgca tttcttatag  27780
gcagcctgca gttgggtctt gctttcttgc tgagcctgac agtctgtatt atagttgagg  27840
ttcttagaca agtgtcgttt ataatgtgac tattgataca gttatgtttg tctagtagct  27900
gtttgattgc tattagtccc aactgttctt tgttcccctt cttttcctgc tttcttttag  27960
attagtcaac tgttttttac gattcaattt tatatatatt tttgggttta ttagcgataa  28020
ctgttttgct atcttagtgt ttaggatttt tagtatataa ttttaactta tcacagttca  28080
```

-continued

```
ccttcagtaa tattatacat catagatggt ataaaaatta caatgataca ttttcatttt  28140
tttctgtccc agacacttcc tacctgaatc tgtgagatta tggtttgtat taagcattag  28200
aatattttgg gccatttttt ctttaatttt ttttctgtct cttctttttt atttggggag  28260
ttatctgtga gctgcttgaa agtttcttgc agtttattgt gtcaaattta ggaatttttc  28320
ctttgttatc tctaatttgt gtttatttcc atccactata gtttttactt ctgacaatgt  28380
aatttgcatc tctgcaagta tggtttgttt tttttttttt aaaaaaaaaa accttccctg  28440
cttccactta ttgtcttgag ttttatttgg agtacagaga tttacttaaa atctttccat  28500
gcttgctttt agatttgggg taattcctca ctcctgagac aagacctttc tgaatattca  28560
ttgtcctgtg aagtatgtgg tattttggcc tggctcatgg gaatggacgc tcttccagtc  28620
attgtgtgaa ccccagacat agtttctgct aattttcttt aacttttttt aaattttatt  28680
ttccattgtt cttaggaagt ttcctagcac acaagcactt ttcattactc cactaaatac  28740
acaagaggga atctctgcac acctccagga tttgtttcct gtactgcttt tttctctcca  28800
gttttctgtc ctgtgatctc tatctgcttt ggttttccta gcctctcagc ttcatcaccc  28860
cagctctatg tcagattttc tcccttttc atggccttga acctctgtta aaactctgtc  28920
aaaagagctg ggacatttgt aatgcctgct atatttgttt tctgtctttc agtgatcacc  28980
taccatcttc attgcctgaa gtccactgtg ttgaaaatca ttgtttaatg tattttgtct  29040
gttttgtttt ttattcattt agataagatg aaaaatcagt atctgttact ccatcagagc  29100
tagtaacaga ttgcagcaga gcttcagcac agcacatgct gcaaaccggc cagagtgatt  29160
ttctttcctc tttgcttaac tgcttctttc tcatccttca tttctcagtg tagcatctct  29220
tcctcacgga aatcttccct ggatgaagta tagatcaaat tatcttatgc aatcatataa  29280
ctatggtttg tgtttttttt acaggaccca tctgagttta taactgtcat ctttttatct  29340
tggttcttcg ctatacttta agctaaaata atagcagaag tgttgtctta tcttcagagc  29400
ttattataat atcttccacc ttgtaggcac tcaatatgta catacttgtt cagtgtctga  29460
atgaatacat gttaaaaatg cacggtcctt tatatccaga aatctactca tgtattttat  29520
ctctactttg ctttttccca gttacagatt gtgttcacct attgaaaatt aaaaatacat  29580
tttgtttgtg taaaagatga atagaactta aagaaaatct ctgtgagcaa cttggagtaa  29640
aaattcaaaa aaatgaaaaa taaggctagt gtactacaaa agagactatc tgaaaaagaa  29700
gaaataaaat cacagttaga gcatgaaaca attgaattgg aaaaagaact ctgtagtttg  29760
aggtatgacc tagttttaaa taaatgtttg aactatttgt tttatattaa agacatataa  29820
ggagaggttt tgtaattatg aactttcctt ctaggattta acaaggaaga aagcttctta  29880
atcttataga gtgtgaaatt attggatata atatcactag ttcttaattg tgaatacttc  29940
tctaataatt aaatgcatat tcttttaaat catagtttta atggctgtat agaattttat  30000
gctttggaaa tctcattatt taattgatga attgaatttt aggttttaaa aagtttttgt  30060
aataatgcta caaggaacat cttttatata cacatagttt tctacatttc taattattta  30120
ccttggataa attcttctgg ttaaagtata gacacttttt tagatctgtt ttacatcttt  30180
gatcaatatt tctaaattgt tcttaagaat gtttatatta atttataatt caaccaacag  30240
agtataaaac agatattttt ctttacacag aataattatt ttaaaaacta tcagccaggt  30300
gcagtggctc atgcctgtaa tcccagcact tttgtaggcc gaggtgggca gatcacgagg  30360
tcaggagttt gagaccagtc tgcccaacat agtgaaatgc tatctctact aaaaatacaa  30420
```

-continued

```
aaaattagcc aggtgttgta gttgaacctg taatcccagc tactcaggag gctgaggcag  30480
gagaatcaca taaacctggg aggcagaggt tgcagtgagc caaaattgca ccattgcact  30540
gcagcccagt gatagtatga gactccctct caaaaaaaaa aaaaaaagga atccagtttt  30600
attgttaata tgcagggaat aaaaagtaaa atagaaagtg attactgatt agcttattca  30660
acatctctgt ctctgctatg tagataaaat taattcagtt ttatgctgaa gacatgtatt  30720
attctttatt gtttaattaa atattagatc ttgtgttgtt ccaaaacata ttttaaaatt  30780
ggttataaaa tacatactaa tcaataggat agactggaag tgttacccaa aaaacaatct  30840
taaaaagtgt agggtaacat attacattct taacctagtc ttggattaca ataatctgta  30900
gatatgtttc ataaagacat caaaaatgct atcttacaat ataaattatg tttagggata  30960
cttgcaatga atgtttcatg aagatgaaaa tgtatttcta gtgaatgtat caacttgttt  31020
ataaaaagta actttatgtt aattaactaa atgattcatc ctaactgagg agtaattact  31080
gtgtgaagaa aagataattt ttatcttgta actttactga ataattttca acatcctttt  31140
tcatactatt tgctggagtt actagtaaca gaaacttatg caggttgttc ttttatcaat  31200
acatttcaac ttacacatgt cctttggatg agattgaggt gagaaactaa aaacatgagg  31260
actagaaaga aaaataatat ttaagaacat agaaatttct ttaggataat aaaccaacat  31320
acgaatgttt tctaatatca acaaagagag tcaaactctg taagatattt gaagagattt  31380
attctgagcc aaatatgagt gactgtggcc cctgacacag ccctcaggag gtcctgagaa  31440
catgttccca aggtggtcgg ggcgcagctt ggttttattc attttaggga ggcatgagac  31500
atcaatcaaa tacatttaag aaatacattg gtttggttca gaaaggcagg ccaactcaaa  31560
gctggggctt ccaggctaca ggtaaattta aacattttat cgttgacaat tggttgagtt  31620
tatttgaaga gctgggatta atggaaagaa atgttcagat taagataaat gattgtggag  31680
accaagtttt attgtgcaga gaaatctctc agcagacttc agagagagca gttgtaaaat  31740
gtttcttatc ggacccaaaa gggtgcctgg ctgttagctg attatcccct ggatctgcat  31800
agaaaggaag gaaaacaaag gggaaagggg gtactctatg gaatgtggat ttttcccaca  31860
agagactttg cagggcaatt tcaaggcatg gcaaggaaat atattttgga ttaaatattt  31920
tcttccttgt ctcataatgt tatgccagag tcagattgaa aagcaagtca caatatacag  31980
ggtcaaataa aacccatctg atgagaatcc atggtttgta gagcatgact ccctggaccc  32040
cttaggtagg aatttgggca agataaaaaa ttagagctta gttctcactg ataagataaa  32100
ttctaagata agtatattta cagatttgcc atgcagcaag gaaaaaaaga aaagaagaaa  32160
tgttgaagag ttgcaccaaa aagttaggga aaagttaaga ataacaaaag agcaatggaa  32220
gatagaagct gatacgacaa aacaaattaa accggctctt gaatcagtgg aggtggaatt  32280
aaagacagga ggaaataatt caaatcaggt aaattaatgt ttggtaaaac ttcatatttc  32340
tactcattaa tattacttac aatatctctt tcatttaatg tatattattt agacctaaac  32400
agtccccaaa ttttatttca tcttaaaaat gaatcatggt gggccgggcg cggtggctca  32460
cgcctgtaat cccagcactt tgggaggccg aggcaggcgg atcacaaggt caggagatcg  32520
agaccatcct ggctaacacg gtgaaaccct gtctctacta aaaatgcaaa aaaaagtagc  32580
caggcatggt ggtgggtgcc cgtagtctca agctactagg gaggctgagg caggagaatg  32640
gcgtgaaccc aggaggtgga ggcttgcagt gagccgagat cccgccactg cactccagcc  32700
tgggcgacag agtgagactc tgtctcaaaa aaataaaaaa taaaaaataa aaaataaaaa  32760
aaagaatcat ggcatttata gctacaatta tttataataa atcttgaaat attttatttt  32820
```

-continued

```
agttcaaagg ccttatggaa agcaatgcta ttctataata tatacttaat gatattgtaa  32880
gtattttgtt ccttgtgaca tagttcagca tattttcccc tatttcatgt taattacgtt  32940
tcaaatgtta tggaaaagaa ataaaagtta tcccaatagt aaataatctc atgattctct  33000
aaaaagagct ttataaattt aattttcttg ccttttggtg tcttgaaata gaagattatt  33060
tttgtatgta tgtatctacc tcacagaagt tattgatttg gtggaagagc actaggagta  33120
gagtcagaaa agctgggaaa aattcctgcc agcttccctt aaatttttaa ccttttgcta  33180
tagaattata actaaatgag ttcattgatt tgtgtgtgta aaagtgctta gtacaatgcc  33240
tagacttatc atttatcaat aaatatcatt cttaaaactg acaataaaaa tattagaaaa  33300
gtagaatatc tagacaatat tttagaaaaa gggagcttaa agaatttgga aaatgtcatt  33360
catctgtcca aatgtctgcc aagctacggc tctcactaca gggagaggta tagtttagat  33420
gttagagtgt aaacccaatt ttttaatgtg gtcatagtta ttaattcttt atgccttgca  33480
aattgttgta attcagtaaa agcctttgtt catcctgaaa atttaaaaaa attatctagt  33540
ggtttttttt ttgctttcat ggattcactg tcttcaaata aacttttgaa ctttggggaa  33600
tttatgccat atgaagtttg aggttttgac tcaacttctt ttttcccatt tagatataca  33660
gttatggcaa cctctcattg tataaatgta cgggttatta tttaatttca gaaacaatca  33720
caatatgtta tcctattgga tactagttac aagttttctt tgttttattt agatttctga  33780
aactgatgaa aaagaagacc tgctgcatga aaaccgcttg atgcaagatg aaattgcctg  33840
gctcaggctg gaaaaagaca caataagaaa ccaaaacctg gaaaataaat acttaaaaga  33900
ctttgaaatt gtgaaaagaa agcgtaaaga ccttcaaaag gctctaaaac ggaatgggga  33960
aacaattagc aacaatgata gcctgttata gtggacagct tgcgtgctct gacagatgaa  34020
aacacaacgc tgcattccag actggagaag caaagagaga gcaggcaaag actggaaaca  34080
gaaatgcaat catgtggttg tagactgaat gctgcctcta tgtgatcatg atcaaagtca  34140
ttcatcacga aagagatcaa gagcttgctt tccagggcac agtagataaa tggtgtccat  34200
taacaggaaa atttgaattt ttgatcctga ttcttttctc tgcaactttt ccaaagctga  34260
gagtaagtcc aagagtcctc gaaacttgag ctccattaca caagagaggc tctgaaagaa  34320
aaggctttgg tttttgaaca cgtgcaaagt gagctaaagc aaaaacagag tcgagtgaag  34380
gacactgaaa aaatgtacaa aagtggatac agtacaatgg aaaaatgcat agaaaagcag  34440
gaaagatttt gtcaactaaa aaaacaaaat atgttgcttc aacagcaatt ggatgatgct  34500
cgcaacaaag ctgacaatca agaaaaagca atacttaata ttcaagccag atgtgatgct  34560
agagtagaaa gccttcaagc tgagtgcaga aagcaccgtc ttttactaga agacagtaaa  34620
aggttggtca atggattgaa tcatttgaaa gaaaaagaac gtcaatatga aaaagagaaa  34680
gcagaaagag aagtaagtat caagaaaaat aagtattttt caaacttcct gaagcacaat  34740
ttaaagtaat atttggttac agctgaatgg tggatctagt tgaatataaa aaaggataca  34800
tatgataaat atatctgctt agaaacattc cttgtttcca acaagtcaaa gttagatctg  34860
agagatgttt tcctctgatt aaagtcaatg tgtcacttat aaaattttaa gttataaaat  34920
gtcaatatag actaatagta ataatatagg tcatactact gaaataataa ttttaatgta  34980
tttatgttgc aacattttaa gaccatgata aatcagatat atggaaatgc tcatacctaa  35040
aatggtattt tgaagttgat tcaataaagt gcggtccttt gacagttaat ttcagatttc  35100
ctagatgaac tgaagtgtat tccctatttc ataattactt ttcttcagta gctttaaata  35160
```

-continued

```
tgtcttagtt ggtaaaattt tgtttttctt catgtcagtt tgacttaaat ctctaactat  35220
ttcaatctca agttatgtat agaaatgatc attctattct tcaaaggcat ctaattttac  35280
ttataatatg gggaaaatgc agtaaatttt agcccaaata atatttgatt taatcttccc  35340
actggcattt ataaattact ttcattttta aataaaaaat ttgctcataa tttttatttc  35400
aaggatcaat tactatcatt tggatataac tttgttcagg acaaaaagag gcatagctat  35460
ctgtgattta ttagtttgac actggatccc cattttcaga ctaaggagga tttcagacta  35520
acgaggagtg gcaggactca gagtaggaat ggagtgagta gggaagagag atatagcagc  35580
tgagtcaggt gtgggaggtg gagggcaggt taattagagc atctaaggcc actgtaattt  35640
tacttttctt ctgagataga catctattgg aaggatttaa gcagatgatt taatgtgagg  35700
aactctgagg ttgatttgag tttctaataa aaagaaagag ggaaatcatt ccacaatgta  35760
taatttacta ccatcggtct cacccacata ctcatttctt tttgagactt caggttttta  35820
agcattgcag attcatcagg ggaggaatga ctagtgggct gaatatgttg tgtgaataac  35880
aataccagtt tggcaggaag ataacacctt ctgtatcctt anctggattc agtaatacac  35940
aggaatgtgt acacatgagg aaaagaaggt gaatcgatct gtgtggtgat atttttcaaa  36000
gtgtatgctt tagagttaaa tattattaat ggtttaataa taaggtgatt tgtaaaatca  36060
gtaacaaaaa taacatcaag tagctgtgag acagcttcaa tgaaaacgag atgatgtctt  36120
aaacaaacaa tcagcaacaa aagctttgct ggatgcttca tcgcgtcatt gcatctattt  36180
agaaaatgag atgcaggatt caaggaagaa attagaccag atgagaagtc aagtatgtat  36240
gaaactttgc atgccaacaa ctgttaatct gtagctagtt aactaatata aagtgttttg  36300
gggtactaat tttggtggat ggctttcttt tgtattttta ttataattaa ttttattaaa  36360
attttatagt ggatggcttt cttttgtatt ttccttatta ttatttttat taaagtttta  36420
ttataatgaa cctatatctt aatctctttt attctgccat tttttataca tattttttc  36480
ttaaatattt aaccttagga aagttgagaa ttatgcatca tttctcacag aagttgagag  36540
agtttttttt tttttttttt tacctgttaa acagtctatt tttaatgatt tctctgttgg  36600
catggtgagg caagccagat taattcagag gacaatgtct aatggaatgt ttcagaaaat  36660
tatcttattt ttagtctcta cttttctgaa cgtataaaga acttgtgtgt acttatttca  36720
tagatttcag gttaacttgt tcagaaaggc cattttactg aataaatttt tattatgaag  36780
aaaatcctta ctctctttct attgggctca gagaacacat tttgtctcta tatgaatagg  36840
acagttagca tttgccaaca tgtatctatt ttctcttatt tatagaaaaa gctaaactaa  36900
aaagggggtt atagaaggtc agcaaaggat gagttgagat gttcagggtt ggttaagtgg  36960
gcatttagac aacaaggttt ctcctttggc atgtttaatg gacatctttg cagtttaaga  37020
tgacgctttt aaattacttc tctcctaatg atgacttgag tcctgctatt caatgggaga  37080
gtcaataaga tcctgtagga tcttatttgg aactgacttt gtcgatttta attttgttcc  37140
tgcttgtttt taaattttct tgttgtttcc ctagaaagga aagatgtcgc ttagttttaa  37200
atatttaaaa atgtgcaagt tgctttgcta taataaaact aaatgcatac atacaaaaaa  37260
taaaattata gttgatgtgg tagtgtttgg aattcaaaat ataaatgctt agcgtgaggt  37320
aatcctttat ctttccacat tttaccagtt tgcaagtttg agtatttaac tgataaaatg  37380
taattcaaaa gcaagaagaa tgtgttttag tcctagagca ggggtctgtg aacttttctg  37440
taaagggcca gatattattt aaggctttgt gagccataat atcactgttg caataactca  37500
gccctgcagt tatagcacaa aagtagccat gaacaatatg cagattgaag ggtgtggcaa  37560
```

-continued

```
gtgtcccact aaaattaatt acaaaaaaca ggtaatggga tgatttatcc tagattctga  37620
cctttttaa ataaaaaaga ttgtgatagt ctaaaatatt tatatatatt ttgttgattc  37680
attcatctac tgatggacat ttaggtcatt tccaaatgta attttttttt aattctntgt  37740
tttagtttca agaaatacag gatcaactta cagctactat aagaagtact aaggaggtgg  37800
aaggtgacgc acaaaagtaa aatttgaagc agcacacaaa ataacttgag tatttataaa  37860
gcaaaagagc actgtagtat gaaaattgta tcagttatga taataagtat gtctttgtga  37920
agccaaaaaa gtttcatctg taagctatat tgaaatacat catttttcta cattattcct  37980
aaattttgca tattatcaaa acacaggtag aaaaatgaca gtagcccagt catctacttt  38040
tgcaattgct aagaatttgt gtaattatac cttcagaagt ttgtttagaa tttacatgat  38100
ttaaaaacaa ttatgtgtga gagtaattat tttaaaatgc acattttagg cttgaagtag  38160
aaaatgccat gatgagaaaa atgattgyaa aaaacaggat gaccaaattg agtggcttga  38220
gaaaatcctg cagcgttcaa gtttggtaag ctgatctctt aatttctgtc atactgaaaa  38280
ggaattttat ttttccagta ggatgggtta aatatccctt gtccaaaatg cttgggacca  38340
aaagtagatt ttttctcaga ttttggaata tttgtatata gctaatgaaa tagcttgggg  38400
atggtacctg agtctaaaca tgaaattcat ttatgtttca tatataccta atgcacatag  38460
cctgaaggta attctctaca atgttttaca gtaatttttt gcaggtaaca aagtttttac  38520
tgttttcacc agagcctgtc acatgaggtc aggtgtggaa cattgcagtt gtggtgtcat  38580
gtccgtgctc aaaaagtttc agattgtaga gcattttgga tttcagattt ttagattagg  38640
gatgatcaat ctacagtaca gatgctcctt gacttacagt gggtttacat gataatgttt  38700
cttgtttgac tgaaacatta taagtaatat ttgatttatt tcagatgctg caggtgttca  38760
agagctagat gaaggtatgc tgccaaattt atgaattaat tcaatcattg atttcttgaa  38820
ataaactcta attaatgaac ggtattcctc tcaattgctt ggttaataca tgctacatta  38880
aatatttttt cttatacaca tctagtgaaa gatgtgaaaa cataaacatt catagtgaag  38940
ggtatactta tgctttgtta cttcgtcatg ttccatggct ttaaaaaaat cacaagaagt  39000
ctgtgtatct ctctttttct ggccctacac ttttcttctg ccacccccaat agaactgtca  39060
gcctgcacac tgaaactgtt ctcagaaaac aaaggcatca tcaacttctc aaggttaagg  39120
tagtgattta agctaacaga ccccacactc atgtgataat aattggttaa gcaattacag  39180
gtcacaagca gtcacttgac cagtgacatt ttaaatctct agtcattgac tttgtcattg  39240
gtttactttt gcacctggga aaagttgaaa attccttagc atggaatcaa aactctcaca  39300
tcagtgtggt tcttgtcagg ttattcagcc ttatctttcg ccacttacca tactctgcaa  39360
ctttgttcta gcatccagac aaactagact acacggagct ccacagtgat catcctcacc  39420
tccagctctt tgcattgact tcttccctct atcctacatg tgttttcctt ccccttcaga  39480
tatcaaccta tgaattgcct ctaccaaaaa gcctacaata ttgacacaaa cctgggctag  39540
tatcccttct atgtcttcca gtaagtggcg tcttatgcct gtcattgtac gtatgactct  39600
gcatgggaat tgcctgtttg ttttttcaga ttataacata cagttgttga ggggtggacc  39660
gtatcatctt tatcgtgtta ttccagtgct tgtcctagta ccttagcaca tggttgctga  39720
atacatgaat gaagagtgag aaaccagaag ctctgatact taactgccat gataatgaat  39780
tcagtgtgca actatgggcg aattatattt aatagtaatt gcatattgta catatttttc  39840
attctaatta acactgataa acttttcaac ttatactgac tttctcttag ttaactgtga  39900
```

-continued

```
aatcatttag ataaagaata taatcctttt tcactctaac ttctgaatta taatctgaat  39960
cctctatagc aggggtcccc aacccacagg ccacagtcag gtccatggag tatacagttt  40020
aagacctctg ctgaacagct atacctccat gcttgtttcc agtggccatg acactttatt  40080
taaatatgta agttttatta agactgagct cttaaaaaga aaaaaccaag aaccttagat  40140
acaactagtg aagaattgag acctgtccat atttaaaacc aagcacacga taccacttaa  40200
aaggttcccc agaaagcctc tatcctgaaa tgcttgaaag tgaggcagtg ctgactctcg  40260
attattacca attgcattaa atatgacact tgttttgttt cttttnggct ataaggagaa  40320
aatgtcattt tgtatatgag tgagcacaga ggagagagac tgggggaaag aacagaatga  40380
gctaataatt ttttactaaa tactccagtt ctcagctttt taaatcaaca gacaaaatga  40440
atcagctaaa cctaaaatct ttgtgaatag tataaattgt cttttaaatt aaatgcatat  40500
atttttatgt tttacttttt caagacaaaa gcaggatatt agtacaatat aagatttata  40560
gaggagcaaa tttcttgaga taggaaaccc ttaaaagcag tatttaaagt gcttaaatac  40620
tgtcacatat gtttaataat cataatactt aattgtgaga actgggagct catgttacta  40680
ctaaaaccaa ataaaaattc aatacatatt tgttaactca atttaaggat gtttacctta  40740
atactgacaa agtacggatg gtaacactgc cacactgaga acaggcaaag taatcttcct  40800
tctgctcctt ggccaaaact gccacaaact acacacatat cctgaagtta agaaagcaga  40860
acatatttta aatggagact aagctaaaaa cctacaaatt tactttaaaa ataccttctt  40920
aactaatata gctctatagc taaatattgg atcacttctg tgtagatgag ataaagcaga  40980
aatgtgcaag gaggaattca atgaggaaga cagtaaattg tcaagttcaa acctgattca  41040
aagtgaactt gtcactgcta gaaaacaaca caaccgtagt gtgcatagag ttttcttcat  41100
catccttatt tgatgaaata tctgcagtag acacctataa aaagcaaaat acacaaaata  41160
cgaagttata tttttcactt gttttacact taactgaaaa gcttcagaaa attcataatc  41220
aaaacatata tttttgctaa ggtctagaat aacgattcca aatattaatg ctaagatact  41280
acagtaaaat ggagtcatga cattttatta ttcaactcat tctctcttta gaggtagaat  41340
tctaatcaag aaattataaa tgataatatt ataggtatgt acacacacaa atctatcact  41400
attttaatga cacacacttg ggatctgcaa tgtagttagt ctgaactgag atgtcctgca  41460
aacataaaat acagcacata attacatatt acatgttgaa atggtaatat ttcagatata  41520
tcggtcgaaa tggaaggcat taaaattaat ttcgtctgtt cactataacc tttattttgt  41580
ttcgagagga gtttcactct tgttgaccag gcctgttctc cctgcctcag cctcccaagt  41640
agctgggatt acagttgtcc accaccatgc ccagctaatt tctgtatttt tagtagagac  41700
ggggtttcac catattggtc aggctggtct cttaactcct gacctcaaat gatccactgc  41760
acccagctca ttgtaactta ttaatgtggc tactaggaag ttttaaattg catatgtggt  41820
tctcattata tttctgttag caccgcttta gaatattatt ttgaataaca tccaaatttc  41880
agtattagcc aaatgattat caaccaatat tgttcagtct ggacttagtt ctatttgact  41940
aaatcaacta agtacccact ggtttgttaa taatttctag agtgattatg aaacaaaata  42000
aagctctgaa ctagaagttg tagaagaaga caaggagggc actgccaaaa tcataaaata  42060
cagtcctctt tctttaaaaa gcttacaacc gaggcctgga aagacagagt tgaaacacaa  42120
caggttatgt tcaaggtcaa aaacataaca cacctgaatt atttttcttg aggaacaatg  42180
gaaagaagat taaccagctg ggtgtagtgg ctcatgccta taatcttagc actttgggag  42240
gctaaagtgg gtggattgct tgagctcagg agtttgagac cagcctgggc aacttggtga  42300
```

-continued

```
aatcctgtct ctaccaaaaa tacaaaaaac agccgagcat ggtggaacac gcctgtagtc  42360
tcagctattc aggaggctga ggcaggagaa tcacttgaac ccaggaggca gaggttacaa  42420
gtgagccaag attgtgccat tgcactccag cctgggtgac agagcaagac tccatctcaa  42480
aaaacaaaaa caaaaacaaa acaaaaaaaa aacccagcaa ccttcaaaat cagaaacaaa  42540
tcaaactcga tgtcatcctt tttctctcca ctgagaaatg accactggtt atcaaaaagc  42600
actccaatat ttaaagtgat ctgactccca gtcacagcgt gactgaattc ttagaaacat  42660
acagcaggtg ttaagtattt ctcttggact gatttatgag agaggaaagc cctgaacata  42720
tagaaaatac atttaaaagc agattttttg ttttttttg gtttgtttgt ttttgagaca  42780
gagtctcgct atgttgccca ggctggagtg cagtggcgca atcttggctc actgcaagct  42840
ctgtctccca ggttcatggc attctcctgc ctcagcctcc tgagtagctg ggactacagg  42900
cacctgccac catgccaagc taattttttg tatttttagt agagacgggg tttcaccatg  42960
ttagccagga tgccaggatg gtctcgatct cctgacctca tgatccgccc acctcggcct  43020
cccaaagtgc tgggattaca ggcatgagcc accatgccca gcctaaaagc agttttaatg  43080
gatagtacta atgctttata agagcaattt atagtcatat gaaccctaat gactacaagt  43140
gttaataatg ccaatattca tcattaggga gtaaataaag ccatgacaaa tccaaacatt  43200
agaaaagtat gcaacatttt aaaagtaggg aggtagaaac ttgtatagac tgccatgaaa  43260
gaaattatca aagacactgt tgagtgaaaa aataaattgc agaacagtat ttgaggtata  43320
gcactataat ataaaaacat gcaaagccat tacatgtagt ctatgggcac atataatagg  43380
ctgactcata agaaattgct gcttttcatc agttcagaaa taatattggc aatttcatat  43440
ggatcaacct aatatataaa tataccaaac tggtaacagg gaaataagga ggactgagga  43500
gttagtaatg gtaaattctg atatacctat aacgctttaa ttttttaata gagaaaatgt  43560
attgatgtgt tatatgcata gcattaacaa aattagcttt ctaagatttt agagaatcat  43620
ccaagatgat tcacagaagt agaatcatca tcatcagtaa gaaattaagt gactactaaa  43680
agtaatcatt aattcagtca taggactaat gatgcattga caaggctatt gagatatata  43740
attatggaaa tggctaaaat agagataaag gtatctattt ctacctccca accactaaca  43800
gaaaattcaa cacattatac acactgagca gctcaaagaa attgtaaaga tccattatta  43860
tttttaaaag gaaatttaaa cagtgaatgc tttcactgaa aatgataaac aatatattcc  43920
caggataaac tggaaataaa gtctgcagta gaaaactaca aagtccctag attcaagtgg  43980
gggtggggag tcatatttga ataataagtg cagaaaaacc aaaatatttt aaaataattg  44040
tccatggaag aaagaaaaca gtatcatcta gcttgaagac ccattgttct tattttataa  44100
tttatttcag acctttagac tgttagaata ataaaaccta acttgagggc aaaggtaatc  44160
tttgagaaaa tatgtgctat ttttgcctgc atagataata gtgtgattta tccagaaggt  44220
gatagaaata tcattttcct agaccacaga tataagccaa ggagaacaga aagctctgac  44280
ctaaacttca caagtgtccc ttccaagcag ggacatgtaa gagtaaacaa aaaaagaaga  44340
tcaaattaaa ctcaaagtgg gaaaatagga aaaaataaag atgagaatat aaatcaataa  44400
aacagaaagg ggaaagaaaa tagagaaaag tccatgaaaa caaaggctga ctcaagaaga  44460
tcaataagat tgataaatct ctagccagac tgatcaggaa aaaaattaga cacacattat  44520
tagtatcaag aatgaggaag gtgaaatcac tacagattct acaggtatta aaattattag  44580
aaacattatg atcaactcca ttcctttaat ttgtgaagat agacaaaatg aacaaatttc  44640
```

-continued

```
ttgaaagatg caaatttatg caaggagaga cagataacct aaataggtac ctattaaaga  44700
aataaaattt gttgttaaaa actgtcccac aggctgggca ctggtggctc atccactaat  44760
cccagcactt tggagacgga tcacctgagg tcaggagttc gagaccagcc tggctaacat  44820
ggtgaaaccc catctctacc caaaacacaa aaattagcta ggcatgttgg tgcatgccag  44880
taatcccagc tactcagaag gcctgaggca ggagaattgc ttgaacctgg gaggtggagg  44940
ctgtagtgag cagagatcac gccactacac tccagactgg gcatggtggc tcacgcctgt  45000
aatcccaaca ctttaggagg ccaaggcagg tggatcacct gaggtcagga gttcgagacc  45060
agcctggcca acatggtgaa aaactgtctc tactaaaaag acaaaaaaag aaattagcca  45120
ggcatggtgg caggcacctg taatcccagc tacccagggg gctgaggcag gggaatcact  45180
tgagcctggg aggcagtggt tgcatgagct gagattgtgc cattgcactt gcagcctagg  45240
caacaagagc aaaactgcat ctcaaaagaa agaaaaaaaa aagaaaacac aacaaaaacc  45300
ccccacaaag aaaatttcag gccaagatgg tttcactaat aatttcatgt ataatataag  45360
aagatacatt tccactacta cacaactttt ccagaaaact gaagaggaga atatactttc  45420
tgattcattc tatgaagctg gagttatgct gataccaaaa ccagatgaag acattacaag  45480
aatgtaagac tacaggctgg ggaatggtga ctcatgcctg taatcccagc attttgggaa  45540
gccaaggccg ggaaaattgc ttgagctcag aagttcgaga ccagcctgga caacatagtg  45600
agatgctgtc tctattaaaa aatttaaaaa agtagttggg tgtggtgaca cacacctatg  45660
gtcccagcta cttgggagac agaggtggga ggtcgaagct ggagttagct atgatcgcac  45720
cactgcactc cagccaggaa ttataatgag aacctgtatc agaaaaaaaa gtgcacaggt  45780
ttacaaccgt ggtgcatcca gttttattaa tagcaagaac agggagtacg ctgttaaaca  45840
caacagcata gatgaatctc caaataattt tgctgaaata aatcagtcca aaaagcatac  45900
agttctgtat gattccactt atatacaact ctagaagatg caaactaatc ttggggacaa  45960
ggacggatgg caggaggaat gcagaaaatt acagagggac atgaagaaac attgggagat  46020
gaatatattc actatcatga ttgtagtatc gttttcaagg gtgtatatgt atatatcaaa  46080
gcttatggaa ttgtacatgt caaatatagc ttatatcaac tatacctcaa taagcctggt  46140
tttaaaattt ttctttttga aaaaaggacg agaatctaag cttccttatt cctggtttag  46200
tagtaaactt tgaacaattt cacctgtctc ctatacttaa aatgacattt cagaatttta  46260
aaaacaggat tttaataaaa tagcgaagtt attacataaa atatttgcta gtagttagca  46320
actgtatttg taatacacat ataaataaag cctcataaca tgatagtaag caaatatcaa  46380
tcttaaaatt ttttaaataa aggagcaact atattacata ctgacttttt agaaagggtt  46440
ggcatagaaa gataaggagt caaagaggaa ggtaagaaaa gaggaaggta agaaaagagg  46500
aaggatgaga aagtaaatat acaagaaaat gtaaccagtg gctcaaaaaa aaagcgaagt  46560
aggacagtaa aataaacatt ttgacctatt tatatgactc ttaagttcaa aataacttgc  46620
tatgagattt tcatcattaa ctgacattta gattagataa aatatacatg aagcaagcct  46680
caccccaggc aatacaacag ctccgattcc acttttcagc tttgacttgc ctcggccacc  46740
tcgccctgac agtcctgcac ctcgaggtct ctgctttcct ggaaatccag acccacggcc  46800
ctatgtaaca gattaggaaa agtcaacatt ctgtgtcagc ccaaaatgat ttttaaatcc  46860
aaatgccact gagataaaac attttattaa atgttataca aacacttctt tagataagta  46920
ttaagaaacc tggcttatta tttttatctt taaaagtata ctgcacaact taaaaatcta  46980
aatataaaat gcttacaaac ttagaatcat accttaggcc tgtcactgtg aacgctatca  47040
```

-continued

```
gcaagccttt gcatgatttt tctctttccc actcctacat tctcggtgac gacaacaact  47100
atagcctgat ccagatattt tgaagtgcaa caaattgtat tcaatataga gtaaggataa  47160
ggaagaactc tctcattaac tggtctcacg gtgattacag taatagctaa catctattga  47220
gtgcttacta tgtactaatc taagtatttt ttactctcaa caatctcata tagtaggttt  47280
tattatcctt atttgagatg agcgtgctga ggaataaaat ggttaagtaa cttgtccaag  47340
gtcgcttagc tagcaagtct ggctccagcg tccctgggtt gaaagcatat ttggactgct  47400
acatcagcag aaatttcgtt tttggctagt gtgtaacaga ttcttccctg tcattaaaaa  47460
ttaagtcagt ttccttcact attccaacag ttctcttatg aactcaacat ttctacctca  47520
ttcacccatt gtatttagag gaaaatttat tattattgtt attactttta tttttgagac  47580
aagaacttta tccatcactc aggttggact gccagtggtg tgatcacagc tcattgcagc  47640
ctagaactct tgggctcaag tgatcctcct gcttctgcct cccgaagtgc caggattacg  47700
ggagtaagcc aaagcatcca gccaggaaaa attatttgag gattacagga aagctgacaa  47760
aaggctttgt gaaagctttg ctttaaataa tctgaataat aaatacttga aatggaaata  47820
atttatctga cttcttacac aagaaataaa cctatgggaa aatgtgttaa attccctgat  47880
aatttcagac attaagtacc agagtatcgt gttccctgcc ccctcaccct tgtttgtact  47940
aattaattac tccttaaaga aacctggcac ctacctaagt agatgaatta tgtatattta  48000
aaattatcca gatgctcagg aaaatactta gacgtttccc tcacgacaag ttaaacaata  48060
tgtcatatat tcaactgatc gtcccttatc atagtttgaa atgaacttat tccctattta  48120
tcagaatgga cccaagtcaa aaattaatgg tgatactgta agcattaaat agaaacacat  48180
gaacaaaagg aacgggagga atggctttct ccctttggat gtaataaata cagccagctc  48240
ccagtttcaa actgccactc ctgtcttctc ttaccctgct ctccttgaga tccctttga  48300
gaagtgcatc agcttctttg cacaacagat ggatggggtc aggttagttt tttgggtttt  48360
ttgtttgtta gtttttgaga tggagtctcg cttctttgcc caggctggag tgcaatggtg  48420
tgatcttggc tcactgcaac ctccgtctcc tgggatcaag caattctcct gcctcagcct  48480
ccctagcagc tgggattaca ggcacatgcc accacgcaca gctaaatctc tttgtatttt  48540
taagtagaga cggggtttca ccacgttgtc aagtttggcc tctaactcct gacctcagtg  48600
atctgccccc tcagcctccc aaagtgctgg gattacaggc gtgagccact acccctggcc  48660
gagtttgttt tgttattaaa ttgggataaa agagttttga aaaattaaat cagtgattaa  48720
aaatcaagac tacaggtaat tctctaaatt tattttcttg aacatgaaaa tggcttgacc  48780
cagaaaaaaa gtaagttaaa aattggtggt ctatattatc aaactgtcaa atgaggtata  48840
tttatacctc aatatcttgg atgatatcag ggggaggtag ggaggttaaa aaaatagttc  48900
ttccagtcat gaaagaaaat aatctagaat tccttaaaat ccttcattag gctaaattaa  48960
acagccatat tccagaatat taaatataga atatgaagaa aaactgtcat ctccagtcaa  49020
tgaagtattt taacttttga gttaatactt tttcaaatta atttttttat cttcaaaatg  49080
catcacacta cttaactcac ttcaaggact ggcagagcca tcaaacaatg tcatgggga  49140
aaaagccttt taagtcattt taaggtatta atacagacaa tgaaatctcc cacaattttg  49200
gtatttcttc tccatgagaa cataataaat taatggagtt ttttcttttg ctttttttcta  49260
agcaacaaag ttttatgata tcatgaatga aaaggtcctt aattaccttt tggtctcatg  49320
tcaaggactt ctccctcata aaaccagtag taatcacaac aaaaggaatt aaccataaaa  49380
```

-continued

```
agaggtatta aaaatgtata cttgattttt aaatgcaagc atattatttc tttacattaa  49440
aatttttaga tttaaaaagt gtttctggaa gctcaatcta gaaaagaaag atttaattct  49500
taacatccag tagggcaaaa caaatcagac agaaatgata tatgaaatgt aaatgcaatt  49560
ttatgtacca ctttgatgct ccaaatggca ctgccaggaa gtgcctgggt ttaaaaattt  49620
cccgacctcc tgaaatgtct ggggaccagg aaggtgggct cactgtatta tgggtactcc  49680
aagcctccta ggatatggca gttgagaaaa tagatgtgta aaactcagca acataaaagg  49740
tcaaagccag caactaagga attttaggac agcaaaaaca aatgcaaacg tatggaaatt  49800
taggacaaat tgcttcaagg aaggcaaaat aagctaatca ctaacagtga tttaaacatt  49860
taagtataac aaatgtttgc tgctacagag acatcactac aatgaaacat taaaaattaa  49920
gggtttatat gacatcaaca ttgactcatg aactgcaatt actgcaccaa gaagtaaata  49980
aaagtcaatc acactttaag aattgacact agaagaaagt attggggggt tatttttctt  50040
ctaacaacta tcgctctact taaaaggaga aatggataac cataagggat tctatattct  50100
atagctatta acaaccaaaa ccagtaggcc aaagaatgca atgagaaaca taagcaatcg  50160
ataaatgcat aaactttaaa ctgtagagag ctggtaacat taaaatgcaa ataccattat  50220
aatcttagca tttaatcact ctttcttcag tgaccactag ttgtcggttt ggtttcggtt  50280
tttacttagg gaaatgaata ctttatggaa attacatcca atggacaaaa gtgaagaaac  50340
gttaaagcaa attgtcctaa atttgcaaat taaaatgcct taagtgcctg ataaattata  50400
tagaaagtag tatcttatta aaatctatat aactaaaact aaagcgtttt acttccaaac  50460
aaccacattc agcaataccc tgaactaatc tgaagatgct aaacagcata aagaaaaatg  50520
tttactccac aaaaataaaa ttttaaagaa aaacaagaca aatgtcaaac aataaaagaa  50580
tatattttga cttaggtaat tcaatggtgc atgcataatt ttaccaatca agtaaccaaa  50640
acttaagaca aggtacgtag tacttaccag gtttctagaa tatcatcaaa ttaacaagta  50700
ctatctcatt aatcacatga aaataccacc aggaattaaa ataaccagaa ataagaatgt  50760
gactgactac tcttggggta agagatagga aatggaataa cagtattttg agaaaagcca  50820
cacaagcaat agactggttt catttttaag tcacaaactc aacccgcaca cattgaagtc  50880
cagcaatcca actcattctc tccagcaaac actatttttt ttcccttcca ggattaccct  50940
caggtgttct ttcttaccca tcaaatctct aacctagctc aggtaatcac tatgctgatt  51000
tcactgagca gcaaccactg caggtcaatt acctcacttt cataatttca aatcaacttg  51060
aatctggcct atgtcttctt ccctactatt agtagggaac tgttgtcaaa aagccatttc  51120
tcttttatca ttttactcaa gctcctgaca tctggcatac tgttctgctg gatttggcag  51180
cagcccacct gtggatattt cactgacttc ctcgctaatc tttcttcatc tcctgtacgt  51240
gttcttcctc tatttgactt ccaaagccct ggagtttccc agggcttgag cctagatcct  51300
aaatggtatt atctacaatg agggcatctt ggaagttgat gcttcccaca ttcttatttc  51360
tggttttaat caaagatctc caaagtagca ggattttcaa cttccttctt agcatttcca  51420
ttttctcaca caaaacccct cttaagtttg ccaagtttaa aatttctccc ttaaccggtt  51480
tcatcccagt cttccccatc cttataaatg gcatccagtc ccttgtcact ctcctctgct  51540
ccttcagtcc tctcccccaa cactttgtca atgcaaatca tcagcaaatt caagactttt  51600
tatcttcaag ttttgtctcc aatccttcta cttcttgtca cttccaccac tagcagcaca  51660
ctcgtggcca ccaccatctc tcacctaacc tgctacagag cctactgctg gttatgcttc  51720
tcccaccctg catatactca aacctttccc cacagcagcc agaggaactt ttcaaaagta  51780
```

-continued

```
caaatgtgat caagcaagtc actattctat tttaaacctt tcaattgctt ctcagagcac  51840
ttaaaataca aacctttccc agtgcctttc tccaactcat tttgtggcac ttgtctcccc  51900
tagtgctatg ctccagctat tctggcttcc ttgctgtcct tcaaacatgc caagctctgt  51960
atcaatcaga gcccagctga ctcagaacac ttcactatac cattctggcc cttcaataaa  52020
tgtctggcat tttctttctt tctttttttt tttgagatgg agtctcactc tgtcacccag  52080
gctagagtgt ggtggtgtga tctcggctca ctgcaacctc tacctcccag gttcaagcag  52140
ttctcctgcc tcaagcctcc tgagtagctg ggattacagg catgcaccac caggcccggc  52200
taatttttgt attttaggag caataacatg ttggtcaggc tggtctcaaa cacctgacct  52260
tgtgatccaa ccaggcttgg catcccaaag tgctgggatt acagatgtga tccaccacgg  52320
ccagccatgt ctggcgtttt ctaacccttc aggtatggcc ttacatattt tctcatcagg  52380
agacctttcc ttagtgctcc cagtgaacca tcatctctct taccacacca ttagtgcctc  52440
tcattgcatc accacctagg acgttttatt gtttgtaatt ttatttagtg gtaggctgtg  52500
gggcaagaga tacctaaatt acttctctca atatttccat tggtttttct ctgagatttg  52560
gctaacatac atcttaaatt ctttttagtc aatagtttaa tattatgttg gcagtagaca  52620
gttctaaaaa atatgagaca gaaagtcata ctctaagata aaaataatgt tgaataattt  52680
tatttcagaa ataagaattt tctggtaatt atgtattatt catcataatt taaaagttag  52740
ctttgatgcc aaaattttat ctcactttga aaagacagac tttgtgtaat tttatagttc  52800
tgaagaaaaa ttatcattat acttagatat tctgacaaat tatctagtat attccttaga  52860
ccttaaaact aaaatatagc tataattatc aaagtttaaa ttatccttca gatcttagct  52920
ttgatcaaga atttacacaa accattcaga aaaggttacc tgcccctgta atgtatgggc  52980
tcttctccta caatccagtt gcagcacttt ttacactgaa ttaaagatca tgcccctttc  53040
tgtccactgc tacgttaagc acactgttca gcacttactg aacttttttt ctgctgagca  53100
tctattatct ttttttgcat gtgtgtatga attcatcaat aaacaatgag ctatgatatg  53160
aaacacacta atgcctccac cagtaataac ctagaatctt gaatttcttc acttaaaaaa  53220
aagttactaa aaattactaa aaaaatctat ataatgcctc cttaatctac aaactgaatt  53280
aaaagcaaaa tagttcctaa tgtaatcatt attaagttgt aaatagaatc aacttgctat  53340
caaatactac agaaactaaa aaaacactac ctggcaggga ctgaatttga acccaagaaa  53400
aataatttaa cccaaaaata gtttaatatt agcattaagt ttctttctgc tttgaggcca  53460
atttctcagg taaactgtcc aagctagtaa atcatacaag gactgtggga tggggaaatg  53520
agaacaataa tgacaagtgg aggataggct atttagaagc aactttctat taaaagtcaa  53580
attctattgc tgattgttaa atacgatcaa agtcattctt acagcccaag agtactatca  53640
gttttaaaag cagccataca aggtttggtg tctcaaaggc aaactttaca cctccaaatc  53700
ttaaatcaac cccggcccca cactcttcca acatactatg taaaaccaag gttgcttata  53760
aacagtaagt ctaatttagg aaaagtgaaa gcaatgaaga cagagggcag aaaggaagat  53820
aactggtaaa agaaacaaaa gagtttacag tttgtctttt tggtaaatac aatcacttgt  53880
atacactgga gctacagcag caaacacttc actctttagg gaattcttaa aagaagtctc  53940
atatataaaa ttgagttcaa tatcaagtag aacaagaaat tagacccaat cctgttttga  54000
taactacagg aacagctatt atcagcttta gccttcaata atttcacaat acaaattagg  54060
tagtgctagc aacagtaatg tctccaaaaa taccacaaca agcacaagtg aactaaaagc  54120
```

```
aaagtctggt acttctaatc tgctgtgttg ttagcttggt gttccaaagg ggtaggtatt  54180
ttttaggttt aacactatgg ttctctggct acttttaaaa ctgaaagtac tcttcttata  54240
atataaagta aacttctaat aatttgtcca agagatatca aaatacagta cctatgtttc  54300
catttatgaa attttcttga aatatttact gcaggctggg catggtggct cacccctgta  54360
atcccagcac ttagggagga caaggcgggt ggatcacctg aggtcaggat ttcgagacca  54420
gcctaaccaa tatggtgaaa caccatctct actaaaaata taaaaaaaat tagccaggtg  54480
tgttgacgtg cacctgtagt ccccgctact caggaagctg agacaggaga actgcttgag  54540
ccaggcaggc agaggctgca gtgagcgagg tcgtgccaca actccagcct gggtgacaga  54600
gcaagactca atctcaaaga aataaataaa aataaaataa atatctactg caaataatac  54660
gtttcataaa atgcttaata aaaactttca ataccaccat gaaagcaatt agaacatgag  54720
ggtgcctgaa gtagatcata gtagtgtgat tacattcaat atctttctat aagacgtgat  54780
gatacataca gggtaaatca tacaagaaga cctaagatta ttatctcaga atttcctaat  54840
tagaatggga atcaattgtg caatgagaga aatggactga agacagaaat aaaaacaaat  54900
tttatgattt aatatgacaa atttaaaatt tccactttat tttccaccat ttttaaaggg  54960
cattccttat agtattaatt ttaatgcatt tttaaaaatc agtaagacaa gtagcacatt  55020
tctctagttc aggactccac tttcagggtt acagttaaag atgatcctag aagtgcattt  55080
taattggtct aggggagggt cattagcttg atgttctaaa atctactgag ttgattacaa  55140
tatgtgtcag tgtcaataac cactttnctt aaacccaagt cgcaaagcac atatacctat  55200
agaaatgtcg aaaatgggcc aggtgctgtg gggctcacac ctgtaatccc agcactctgg  55260
gagacccgag atgggaggat cacttgaggc caggactttg taaggagcct ggtctacaca  55320
gcaagacccc catctctata aaaaaataaa aaatattttt aaatgctgaa aaatgaaata  55380
ctaaattatt tatgaatata taacttcaat aaaagatgag aaaatacaac taggtcatta  55440
ggacaatttg tatgaaacaa tatccaattt gctgtctgtt acttctacct tatcatgtct  55500
aatttttcct catctttgtg aaatcctgca tctacaatag gcaaaaaaac aaaaaacaaa  55560
aggaatctta ttctattcac agccatcaga aaaatgtgtt actattcctg tagtcagtta  55620
ggttctaaat catacatttg agatatatct caaacatgtc ataaagaaaa taagcatcat  55680
atttctaact aaatagcacc tgaaatattc catatgaaag gaaaaatacg aaaaactaaa  55740
cttttaatta ctaacctcct taaaggaaaa taattctata tgatttgata tttcataatg  55800
gatgtccaat acctgagata taaattccat tttctgtgtc ctaacatctc accttcagaa  55860
aatctccaat attgggttat ttggattata tatttaaaac tgaatatact tgaagatgtg  55920
aatgatttgt tgccacaaca aatggtttac aattatctgc attaaaatgt gttccatgaa  55980
caacagaaaa agaatatttc tacttcagtc cttaaaaatt gtgaaagcac agccacagtc  56040
ttagtttgtc gatcttcaat tcttttggta ttttaatttc accaataatt ctggaactgc  56100
tggttttgta tttctcaaaa tgtttgtctt gctcatgcat cttgcttaca tcacaatcac  56160
agctaggaaa agcagcttat tttaccggca gtccccgtgt gaagaatatg tagaagcacc  56220
agtaaataaa aaaggaagtt tatccagaat gcctaattca aagaaattca tgtaacatga  56280
atactgaact tcagtatttc taatatacgt atatacacat tcctgctaac tgtagaatat  56340
tctcctgcaa gtttatggtc cctgtgcctc accaatggaa gatctatctt gtactattca  56400
attcatactc tccctaataa cagcactata ttagcaggta tcatcatcaa gtgaaggctg  56460
cttgctagat aactaaaacc aagattggaa aactaaaaag ctggagggag ggaaaacaca  56520
```

```
gcctacaaaa tgcttacacg attagcagca aatgatgaag tagttacaag aggggccgaa  56580
gaatagaaag attatcatcg gatttgggaa ttcaaaggca gctcagcaaa atactaggac  56640
atggctcata taagatggaa atataagatg gaataagcct ggaaatacac cctcctcccc  56700
aatatttcag aacataaagt ctacagaaag agagtcctaa tgtattgaac ctggtttctc  56760
aattgaaaca aaagtcttca aggaaggaga gatacgtaaa atttaacagg aatacatatg  56820
aagcagtatc tttaaagaat gtaaatatat caaccaaaag taaacttgag attcaaattt  56880
ccattgctaa agtcttttca gagtcagaac gacataatta ttatataact attcaaaaca  56940
aaacaaaaaa acttactgga aaaaagaaca actggtttga gaagaaaatc ttttcatggt  57000
agagcagaaa taactgtcaa ggaaaatact tagaaaaagt catatataaa gagtggccta  57060
gttttactgc acacgtcttt gccatgcaga aacagctaaa tcccatctga caactacttt  57120
ccctttcgtg taccttgtct ttagagaata aaatatatct gggtttgata tagagagaga  57180
ctaattttca cattaaaaat gattttctta aaagcctggc cttacagttt aaaaattata  57240
cgattaacaa tcaagatatt attcctataa aaagccaaac tttaatccat ttaaatcatg  57300
aaacttaaaa cttcacttga agcaatttca atcatgaaac ttaaaactcc aaattactat  57360
tgtgaattaa cacttctcca ctatgtatct tgcaatttta aaaaaacact tcagaaagta  57420
gcatatttgt aaaacaataa ataattcata cctatattat cctcattttg ccatgcagtt  57480
ttacttaaat ctcacttaga aatggaactc attcttaaag ggtagaatgc acatgatgta  57540
aagcagacac aggaagattt atctttactt actgaaagtc aatagtacaa ttctaagatt  57600
ttttccatga aactactgaa ataagtccta cttgaaaaaa gaaatcccac aagagttagg  57660
aattaataaa aacaccaaaa tgagaaaccc cccagcatgg aaaattcctg tcataaatgt  57720
tgatgtttat ccagttaaaa atatatacaa tgaataatat caataaatat attagaagga  57780
aataatagat gtcagttact gtacccaaaa ctatactgta ttttaggctc tatatttact  57840
gcagcacaga actaaaagaa tttttaaagc tcttgctatt agaaactatt atccataggg  57900
tgcatcttta tgcaccagct gagttgaaat tccaaataag attcccttcc aaatttaata  57960
aatggcattc ttcattaaca gcatttaaaa aataatggct gaaacatata atcaacatta  58020
cactgaagtt ctatctgaag acagaaaaag ttgccatcca caccaaagct acacatatac  58080
cttctgattt tatagaattg ttccaatatc ttttctgtca atatcattaa aatcaaccta  58140
cctgtttgga ccgaggtcta ccaggagaaa attttctctt agtaatagct ggtttaccca  58200
tgccagtttc ttggagtgac tgagatgtaa gttgttggca tgatgtttcc agcagacgaa  58260
ctaagagctg aagggtaatt atgcagcatg tcatgcgaag gcaagtctga agaaggtgtt  58320
ggggaggaag acacatctgc cttgcttatg tctgctgata atgaaaatga tgactctgtc  58380
tcagatgata actttataga tttgcctcct tggtatgaaa catctttcac acaaccctca  58440
attgtaggag tcatttcaga gtccatcaat ccagtagaaa gttcagaatc ttatttctgt  58500
tccttttctc cttgtagcct ttctataacc aactgttcct caggacataa tgaagtgctt  58560
tcctcatgtg ggacactaa ggtttctagt gggaagagtg acagattcaa tgacaaattt  58620
tggaggcctt gattcttctt ttggatccac tgttttaggt tcctctaaca actgcagttg  58680
ctctgctgca cagtgatctg gtgtgtaacg acttcaatgt tttccggcac tcccatttta  58740
tcttcaattt gatctccccc acaaatatgt ttcacttcag aagacatttt catttcttca  58800
ctatcagcct cattagaatt ctgtttttcc aattcgggta ttcactgtat gttgggatga  58860
```

-continued

```
tattgccaaa attcaagaac attttgttat ggtaatgtac aaccaaattt ttaaattttc  58920
taactataga tatataaaac atttggctac actagaactt aaatcagaag gtattcatca  58980
aagcagacaa ttattaagtg aatgaaagcc aaagtacata aggatttatg gattagaatc  59040
anccncncac cagaaaacct aatgaaaaca tgttttacaa cacaagtact tccaaatgga  59100
ttgaaaatta cacaggaaaa gctctcatac tcattttta gttaagaaaa tgaggatcaa  59160
tcatgttatg tgaggtacct aagttaaaaa gtaaagactg atctagaatg tgtaggcatt  59220
ttctaatagt aaatacccag atgcgacaaa gttactatag actcaaaagc acagacagaa  59280
aagatttgct aaccaccaat atttattttg cttaaccata cctgccaacc tagccaaaat  59340
attctttgga tataatcgtt gttcttcatc attgtctgta aattaaaaga ctaatctcag  59400
gaaatctata aacttagata tcagaaacat agtcaccggt aaattttaaa tcaggatacc  59460
agtatgttaa acctttaact caatctcatc aaggtaattt ttaagttata gtaaaaagac  59520
actgctagcc tcatttacca atcagtgact aaaatttatc tatttatcta tgttcttttt  59580
tttttgaaa caggatctca ctctgtgacc caagctggag tgcagtagca gaaacatggc  59640
tcactgcagc ctcaacctcc tgggctcaag tggtcctccc acctcagcct cccaagctgc  59700
tgggactgca ggcatgtgtc accatgccca ggcctataca tgttctgata ccaaactgat  59760
accaaactga aatctcatct tctttcccac tttattgaaa gactccaggt aaggataaaa  59820
gaaaactccc gaataccaga tctgatagtt agtccaaaat atttttaatc atgacctccc  59880
ccctccaaaa aaaaaagcct ttcaagagga acctaaccta tctttagatc cattgtcaat  59940
tcttttccag aatctcttaa ctaaaagatt tagttactgt aatgtatata catccacgca  60000
attgcaaaaa tgtctttgag ataaagacat tatcttataa ctcagtccaa ttagacaata  60060
tgaacatact gcttaccagc aatgagaaga ctatctgtgt cctctatacc gtcagtgtag  60120
ggaaaggctt tctgaatatg actcaaaaat ccagaagcaa aagaagatta ataattctaa  60180
ctccacaaaa agaaactttt gcatggcaaa aaaaaataat aaaaacaaag tcaaaagaca  60240
cataatacag cctggataac atggtaagac cctgtctcta caaaagtaaa aaattagctg  60300
ggcttcgtgg tacacataac tcctagctaa ctcgggaggc tgaggcagga agattgcttg  60360
agcccaggtc aaggctacag tgaactatga ccataccaat gtattatggc tggggtgaca  60420
gggtgagaca ctgtctcaca caaataagca aaaaaaaaaa aaaaaaaaaa aaaaaaaaac  60480
aagctagcag aaagtatctg catcatgtaa cacatataaa ggcttacatc cctaacttat  60540
aaagaactct taagttaggg aaaaatgcca aaatctttaa taacaggcaa atcacatgaa  60600
cagacaattc atgagaagaa ataaaaactg tccctttaac acatgaaaaa acgatcaact  60660
tcactcttag gataaacaaa aattaaaact tctttgatac actacttttt acccagatga  60720
cagacaaact ttcaaaagct aaacaagtca tcctgtttgc aaagacgtag gaaaagttct  60780
ctcacacatc tctggtggca atgcaaagta ccataagccc caaaaaaggg aatttcacag  60840
tatctaacaa agctacatat gtgtacactc ctgaggcaat aatcctagga atttacccta  60900
cagatttgtc cctgagaatt caaaaacaca catgcacaaa gccagggagt gtaaaatcat  60960
ttataatgca aaaatgtcat aaccttactg aaatacccaa ttacaggcca cttgggttga  61020
gtaaccgatt agcacagata cacaatggag tgctattgca gctgtttaaa aggagaatga  61080
gatctcttga acttgcctaa cttgcctgga agtgacttcc agattttatt acatgaaaaa  61140
agcatcatgc taaagaacat atacaacatg ctaccttcac tgaaagagca atatatcctc  61200
ttattcttag atgaaaaata acaggaggtt taaaacagat aacaatgaag ttcgttactt  61260
```

```
ccaagaggct ggggaaatg cggtataagt attgacaaga gacagtgaca attctgagca  61320
aaatttcata tagtttttga gttttgaaag tatactaata ccttctatat ttaaaaaatt  61380
aaatcactaa gaaaaagggg aataaaatct attactgaga gcaaactgaa gcagacttgc  61440
tttttagatt gagcaactga ataaatgtgc tgctctacaa cccagaattt ttattgtaga  61500
agaacagaca tgcaagaatg aaaaggcaaa gaactcagtg gagaaggata agaactggag  61560
gtgctggtat aaattcatta tttctaagtg atgtatatgt atatgaacat ttatgtgtat  61620
atacataacg tgtaggggtg ttcaatcttt tggctttcct ggagcacatt gatagaagaa  61680
tcgtcttggg ccacacacaa gatacactaa cactantgac aactgatgag ctacacacac  61740
acacacacac acacacacac acacacacac acacacccaa aaaaaaaacc tcataatgtt  61800
ttaagaaatt ttatgaattt ctgttgggcc acattcaaag ccatcctgga ccacatgtag  61860
cctgcgggcc atgggttgga caaacttctg taagtgtata cacatgcatg catttcgtga  61920
caccacctgc tgaaagggtg aagaagtaaa caccctccag tagcaatgag cacacccggc  61980
acccattccc cactaaagga atctgggtta cttatttaac aatggactta tttcaggact  62040
cgggcatggg aggtataaga tgagcttgta acatcttgtc acaccaaaaa gtaatgaagt  62100
tgttcaaaaa agcggtgagg gcagaacacc agtgccagcg ttgaaggagc aactgacagc  62160
aagtatgtga ctatttgagc caaaaaataa ttaggtaatg agttgtaaat gattgaagat  62220
aataggagtt catgagtcaa tattaatagt aagcttaaca tgtgaaagaa gtgttcttgc  62280
ttacaaaaga aagcagaggg ctaactggta aatgtggtgg gagtgctaga gctggaaatg  62340
catcatttgc aaccaaaaga aagcatgtta aaatggcatc atcaggcagt aagtttgttg  62400
ttgtttctgt tgttgttgtt gttgttgctg ttttttgaga taagaagtct atctctgtca  62460
cccaggctgg agtgaagtag catgagtcca actcactgca acctcacctc ctgggttcaa  62520
gcgattctcc ggtctcagca tctgagtagc tgggattaca tggcacccgc taccatgcct  62580
gacctaattt ttgtattttt tagtacagac aggggttcac catgttggct aggctgatct  62640
tgaactcctg acctcaggtg atccacccac tttagccttc caaagtgctg ggattacagg  62700
tgtgagccac cacacccgcc tagggagtaa gtttttcaaa atctttaagg aaattctgag  62760
gaaagcaaga tatttgcatg gtcttaaagt atcctcacat actgctttat tagatacaaa  62820
ggagggggga atagaaattg ggcaacagcc tgaccaggtg attctcatga gggaaagtgg  62880
aataatatgt gcttccagtt gtgataccct gaggatggat cagcatttta cagtattctg  62940
gccaataatg catgcctctc atctaattat aaggggttat caaaaacaaa atggggaaat  63000
ttctgtttga acaaagaaaa aaaacaaata tatcgagaac tctattcttc ataaatacca  63060
atgacaaaaa ctaaatccta gaacctactt ggaggaaggg gtagattatg agggacataa  63120
gatcaaatga cataactgta atatggctgg tacattagat aaacatacgg cattgatgta  63180
agtttaggaa tttgatagca ggattgtgat ttttaaagaa tattcctact attaagaaat  63240
acatactgaa atggtggtaa aaaggcacaa tgtatgtaat taaccctcaa atagtagggg  63300
ggttggggga atagagacac acagacacac acacatacac acacacacac acagagaaag  63360
tgagagaggg catgcccaat gataatgaaa tgctaacaac agatatatct aagtaaatgg  63420
gatatgggta ttatttttat tttttccaac ttttagagtt tgaacttatt ttcaagtaaa  63480
agctttctaa aaacgcataa cataccaaag aacagacatt cttgagataa aagtaggaaa  63540
aagaaaccta tctgacaatg actggtttac aataaagatc cttaaaagat taaccccact  63600
```

-continued

```
ccagctcacc agggagcagc cccaaactag actgacagcc ccgtgggggc acactgattt  63660
gccccaacat ctccagcctt cactacagtg gtgttcgcac acagtaaaca ctcaaatgtt  63720
aaatgcaaac aaatgagcaa attatgactc aagactacag agagaactac agaagaatta  63780
aacagcagag aaagatgatc attcttcaaa tggttcaaag gacaaacctt tcaatctatg  63840
aaaaactcta tggtacctgt ttctgtactt actttgtgtt aggcattgtg ctgggcacct  63900
ttatagatac cacttcatta aatcccaaca tccctgtgag gtaagtaccg ttaaccttct  63960
atacactgac tttagggaag ttaaacaggt agccaaagat catcaattta gtaactgaaa  64020
aaactgcagt ttgactccac agcataagct tttaaccacc acactatagt gccttcatag  64080
aacagaataa aaaaattaag tatccaatag tattcccaga aattatgtaa tcctgtcact  64140
ctcaaaagag aatagcagat tacaaagagc aaatcaaaaa gaagcacacc aaagaggaga  64200
cagaacaagc tgagaaagac acccagaatt ctctaccagt tctcaagaca atgaaaacca  64260
taataaagaa gattaagagc aagagacaaa aattatccag tagttactag atattattag  64320
agagtgtaaa gaaggtaatt ttttaagtaa atatattttt taaaaaaggt gctggggtgg  64380
ggggtgaagg cggggatggg gattcacaca tctcccaaag ctttcaggaa gaaaaaaagg  64440
attatgatta aattttttca agttaagatt tttctcggtg acagcataaa ctgaaaaaac  64500
tgaagaaaat gttttcagag tataaaaaag aaaaatttgt aatatgaaac attatactgt  64560
gccaagttct tatagcctaa aaggaacagt ctctttccga catgtagggt ttcaaaaact  64620
ttataattat ttttaaagga tcacaaccaa gactccgaaa gattgagggt aaagttggaa  64680
ttaacagagg aaatatattt ttgcaagaaa attgtgacaa ggtttacaat ctaggttaat  64740
caaatcaaac agagaaaagg ggaataaaaa ctttattttc agtggggaat gggagaaaat  64800
ttatatcttt aatatttata atcatttaca ttcacaaaat gaagattctg aattataaat  64860
cattgcagga agtaaaagaa gagaaaaata gaaagaaaag aaagttttgc ctcaaaacag  64920
ccaagcattt caattacaaa ccgtcaatcc aaacagttac ctctattaag cttttcaaaa  64980
gatacatttt tataacacaa aagaatccaa aataaatgtg aaaagataac cattcaactg  65040
ttaaactaac accctacgtg gccatagtgt caggcaaagc aaaatacctg cccttcctga  65100
tccctcaaca aaaaacacat tacatagaat aaagaacaat tttatactgg taaaaaacac  65160
aatatattaa cactggcctg acctacttgc taaataacag ccacaaatta tttgtttaaa  65220
aatatgataa attgatagga acaattaata gtggtcaatt gtaacttgtt gaatcaacaa  65280
gtcaaaaaat aaggtaaaag gacttcatct aactaaatga aattaataaa cacaaatgct  65340
acacctttaa aaagtcaata cttcaagtat caaaatattt attttaaaaa acctacctta  65400
gttaaattct ctgattaaat gaaatgtaag cataaattaa catacttcag cacaacttaa  65460
aaaaaagtta ttcgctnagg gatatacata cattaaaggt tacaaataca ataaacttgg  65520
cttcagtcaa agctatagcc taaggtaaac ttataggctt aaatgtcctt tttccttagg  65580
aaagaaaatg aattacaaat tcaacttcat attaaaagta aaaaggcaag tagaggaact  65640
gagtgaagat aagagtgtta atatccaatc agtcaaacag cagagttttc ctttccaatg  65700
atgtcattca gcaagagaag gaatctgaac aacctgagga agcaggccag agttcatcac  65760
aatccttcag ccctcaggtc ccacttccca ggtagccaca gctgagcaca gttacccagc  65820
agctcttttt ccccccagga gagaaagccc ctcccctcaa cccccaccac tcaggcagat  65880
gcctagtaga acttgctgaa gaccacaaca gaacctggta atactgcttg cagttctagg  65940
tgccaaacct cactggcgag gacagggtgc aggtacagaa tctctctgcg tctgctccca  66000
```

-continued

```
catcctcccc acgccaggga cctggggttc tggcgacatc accctccttt tccaggccct  66060
ccaccttcac cctagaaaaa gcagttccga gaagggcaat gacaatgctg tgccttccac  66120
tcccgcacac gggccatcac gcccttttca gctccaggga aaacccgctt caggccccat  66180
gcagcacctg agggtcatct tcatccctca acctcgcgac accagcagcc caggaagact  66240
aagcttaaaa gctaaaccgc accttggatt ccaagggcta tgtccactac cccactgccc  66300
ccaacccggc tctgaacgcc tcaccctgaa ggggcagaag ccaagtgagg taggaagtta  66360
gttaatgagt tcatcggcat tttttataat agctcaaaat tttgaaggac ccaaatgttc  66420
accaacaggt gattcaatac acaaattgtg gtatctccag cactcggtaa tacaaaagaa  66480
tcactactga tctgtgcagc aatagggatg catttcaaaa taattacact gagttaaaga  66540
agccagacca aaaacgagta tatactatat gaagctttta ttaaaaattc taggaagtga  66600
atactaatct atagtgaaaa agcagactag gaagacagag ggtttgggtt tgaacagcca  66660
caaagcaagc caagaggcac caggaaactt tgacggtgat gactatgttc attatcttga  66720
agagtgtaca gtttactgta tgtcagttat atgtcaataa agctgttttt aaaaagctga  66780
tggtaatgta tagatttgaa tagatatccg atttgtctgt tctccatata aaacatacag  66840
aggatttaaa aaagtaaaca acttactttg catttccagc cattggttgg tacagatttc  66900
gtaattcgtt gaagacaaaa agtatgatac cctttgtcac acgtatcaca cactagcatc  66960
ttgctatctt ctcccgattg tctaaaaagt aagatagcat taatgatggc ttatctttaa  67020
acttatgttt tgcaacataa gtaatcatga aaatcatcag tcctgggaac cgcacagttc  67080
ataaatacct cagtatctgt tttgtctctg cagatagtac cagaggtacc ctccataagg  67140
attacctcct aaatggtgat ctttacccca atgctcacct atggttaact tgctctagcc  67200
attttaggtt tcctgcaaat gaggaagggt taaggcaaga tgaatagcct ctgatcttta  67260
cttttaaaat ataatttttg agaggaaggc gctgtaactg ctatgtgcta ctgtgtggaa  67320
agatcaaatc ttggcacagc aaattgaaaa gacttgtcat ataacgtaaa gaggatcaaa  67380
tttgacatca gatctctatt tgtatccagg ctgctgtttt ctagctgtgt cactaacaac  67440
ttagactaaa gctctctgag tttcaggtat aaaacgggaa taataaacat tactgtgaga  67500
attaaatgta atgcaggttc aagtgcttag aatgtctatt aagcaattaa atgctgaata  67560
attatttcaa aagatgaacc ttgtcataat tattaagaat tataattgaa aacctaaaac  67620
ctttctttaa acactcttct gcccccaaag attgggcccc tgtcctacag cattatctct  67680
gttgagattt ttgactataa ttactttcag atactatgat tttaaattca agaggagggg  67740
aagagaaaat acagggaaag caagaagagc tgagagagga atctctgaat gaaatctggg  67800
ggataaacag aagtcaacag gaagatgggt cagttggcct ccaattatta ttcagttcaa  67860
cctctccata aaaagtcaca tgttttatct cttcagctac atgcaaagat cttggagaac  67920
aagtactctt ccttcaagtt cttttaatcc ttcccaagaa actgagtgca gatacaaggt  67980
atcgaataaa tgtttactga atattttatc taatttttac caaaatatga aggtacatag  68040
tcctatttat gtcacgtaac tctaagatat tgacgcttat ttcttataaa actaaataat  68100
aaaaacagac tgatcatggc agttgggcat aattcttgct ggtaacaaca aaaattctca  68160
gcctgtaagt gaagatgctg gtaacatccc caaattatca tgctcattag aatcatgggg  68220
gtgcaagcgg aaatcacaga aaagactgga gaaatgacca agagatgaaa tacaatagga  68280
aaagataacc cccttacaaa tttgtaaatg ccacatattt cattttggaa ttatgctgac  68340
```

-continued

```
caggatctac tcaaggtggc ttttagagag atgcagatgt acattaaaat aatagtagaa  68400
agtgtccttc ctggaatgga aattcaaaca catgactgac gttttgactc aactctaatt  68460
cttctacgtc tgtagtgaga ggtttaaatc ctatcacatc cctccccag tgcccctgaa  68520
gacaagttac tttattcttc tcatgcttgt tttaaattgt taatatcgct tattttttaa  68580
actgttggta aatttaaatt agctctttag acgaccagaa caatttaaat gattaaaatc  68640
agttttgttt agacttcttt caaaataata taaacgttaa tatccagtaa ttttttaag  68700
tatgatgaag tcactctgaa tgaatacagc caaaatatga acaacctcta ttatattaca  68760
caaactttta gcgcctagca atagggtgcc tcttaaaccc aatacacagc tttgaattga  68820
aatgaaaact tacttgcagt tctggcacac tttgcactca ggacattgcc aacctgcacg  68880
ttttaaagga gtaaccgcta tatccaggca cattccatga tagtgctgac cacaagtagt  68940
acaaaagaac tgatctaaga ggtctcccgg gctgtcgcac actgcacagt ttgcatcttc  69000
cttcgctata attaacagta aaacaatgaa attgttgtat aagaatttaa atttttctg  69060
actacacagt aaaatcattt gaaaggattt gcatcatgaa cctttcagac atttgaagtt  69120
attcacattg aattgtcatc taatcaaaaa gaggtatcaa taaaaacact gtagggtatt  69180
taatctaaat gtaaccacat taaatttaat cgtatagttt tgcaattatt tggtggctat  69240
atctacttaa gccataagca ggtctttctt taattttcta ttcctaatgc caatgataat  69300
gctggatacc taattaatgc tcaatatatg ctcactgcaa agaaccaaac aaggaaaata  69360
ccaactaaga aatgctttgc agtgtaacat aaacattttc tttgaatgct aaatatattt  69420
tgaaattaca aaatcagaca agagacaaaa ttaagaaacg ttaatatcaa ttagactaag  69480
atgcttctta agcataaaca gactattcaa atcacataag ggcttttttt tgattactgg  69540
aaaatgtctt atgtggaaga acattaaaga cagaagctac atattcatac acaaacacat  69600
tacttaatat actaattcta tattcatcta tattaatttc tagttgtaaa agcattaaaa  69660
tccacataat tatggacatc atccatccct aaatgtggat taaaagaaaa tgtactaaca  69720
gttcttttac catataaaac agaaaatata aggataaact gccctgccaa atatacagtt  69780
aaacttatgc atattgcaaa ataaggaaaa taatgtattc taaaatcata ccaatcttag  69840
ataatgtata aaaaatatgc ctgtatataa caagtatcac aaagtatatg aatcttttca  69900
ttttttgaag gtttgatcat tcctatctac tattctgact catatgttct ttcttttcca  69960
gtcaagctta tcataccaac atttgataat aatatataaa tatgcctgta tttaacaagt  70020
ataacaaagt atatgaacca ttatttttcc cttttttttt agacagtttc actctgtcac  70080
caaggctaga gagcaatggc gcgatctagg cttactgtaa cctccgcctc ccaggttcaa  70140
gggattctca cgcctcagcc tcctcagtag ctgggattac tggagtgtgc caccatgccc  70200
acctaatttt tatattttta gtagagacga tgtttcacca catagcccag gctggtctca  70260
aactcgtgag ctcaagcaat cctcctgcct caccctccaa aagtgctggg attacaggtg  70320
tcacctaccg cactcagcct ttttcccatt ttttgaaggt ttggtcagtc ctatcaattt  70380
ctctctgact catacgttct ttcttttcca gtcaagcatc ttgaaacaga gtaaaaatat  70440
atttctttta tttgtaccgg agtctgcaaa cttttcctga aaagggccag atagtaaata  70500
ttttaggctt tgtgagccat agcagtctct gacaaaaagt cagacctttt gttttaattt  70560
acactctttt aaaaatgtaa aaataattcc tcgcttgagg gcagtacaaa aacaggcttc  70620
aaaatgtgga cgctggctgg acctctgaca tacttcacga aggctggctt agcacctaat  70680
actcatctga agctgcatta gtgaggctgc caatgcccat aggaaacccg atttagtctt  70740
```

-continued

```
tggctttttt gcactttgta gcatttgcat tgctagccac tcccacatta aaacgcccct  70800
ttccttagtt tctatcacgg caactctctc ctaatttctc cttagttttc ccccactttc  70860
atctcatcct cctttgttgg cttttgtacc tatacaatct ttctaaatgc tggagtttct  70920
taggatttca tccttttcct tctttcctaa tcccccatag tttccctttg tgatcacatc  70980
aactctcacg ccataaaatg ccaccatgat tcccaaatct gtattattgg ccctagaatt  71040
ctttcataaa ccccaaacct ttattcttca agtcttactg gatctcaata gccaagtgtt  71100
ctaaacactc aatctcaact gctctaaagt gaaacttttt taaaaacccg aaacagcatc  71160
catttttctc aagaatagat aaaggcagaa accttagtat cattgttgac tctgaactca  71220
gctttgaccc aacacatcca gccagatccc aattcttatg tattaaactt cctacacatc  71280
attctttctt tatatgttta tagtttagtc tatcatacta ggttggtgca aaagtaactg  71340
cagtttttga cattactttt aatggcaaag actgcaatta cctttgcacc tacctaatac  71400
tctgtctcgc taactgcagt atcttctgca tcaaatcatc tctacttacg gttctgacat  71460
cctctctaaa tcattttcta cacatccaga acaatctttc aaaaatgtaa atctaattgt  71520
taacctctgt ataaattaaa actccaccaa tacctcattt ttcacctaaa agaaaatcag  71580
aattttcaag tatgatgcaa aaaggtcctt atctcccttt ccaactgaat ctcagaacca  71640
ctcactattt cgtggtcatg gtgggttgtc ttccatgcac ctcacataac atgctattca  71700
tgtctgtgtg cttttacaca ttctgttccc tctgcttgaa attttgtttt tctgctgtgc  71760
tcccagcctt caaaactctg ctcatggctg ggcacagagg ctcatgcctg taatcccagc  71820
actctgggag gccaaagcag atggatcacc tgaggtcagg agttcgagac cagccgggcc  71880
aacatggtga aaccccatct ctactaaaaa tacaaattag cagggtgtgg tggcacatgc  71940
ctgtagtccc agctactcag gaggctgagg caggagaatc gcttgaacca aggaggtgga  72000
ggctgcagtg actagagttt atgccacggc actccagcct gggggacaga gtgagcacct  72060
gtctcaaaaa aaaaatctgc acattatttc ctgaatacct attaccacac ccaaataccc  72120
atttagttgt cgaatattac ttttacccat atgcttacaa gaaacttctg ttacataatc  72180
atttatttac agcacaactc tgtgaatcct tgaaggacag gagccttaac ttttttaact  72240
ttgtatcccc aactgcctaa catgaatcaa gtcttattga acatatttta agtgaaggac  72300
ttactgctaa aataactttt aaatggctct ttaagtgata ggcatttaaa ataaatcatt  72360
aatctaacaa tggaagcatc ataaattggt tcatttttga tagaaaggac ataactggga  72420
tgttatgttt cttaatatta agagagtact agtatttatc tttcaaaata tgtacattga  72480
aaaattgatc tctttttgct cactgtaaaa cttttaaaaa ttgggggaat actcaactaa  72540
ttatcagaaa ctaattatca gataatcaat tcatttttct attatactct cctaggaaca  72600
ctaaaatgct tctgtgaaac tttctagagt ttgctcccct gaccacttca agttgccatg  72660
gtagctacta gcgacatgtg gtttctgaac aagtgaaatg taattagttc aaatcgaggt  72720
atgcagtaag cataaaatgc acactggatt ccaaaatctt aatggggaaa aagatctcaa  72780
aatttgaaat attactattt tggattactg aattaaataa aatttactac aattgttccc  72840
aaatgtttcc ttttcctcaa atttttaaca tacccactag aaaaattact tatgttgctc  72900
acattatatt tatactgcac agcactgtta tatgcaacaa agttcactct gcaacaagac  72960
aactgtcatt gtcacaaaaa tcacttttta gactatgatg atctccacca atgccttact  73020
gacaaccttg ctgtgttatc tgattactat ggatcattgg taataaatta gtcaaagaaa  73080
```

-continued

```
aacatccatg taatacatct ggtgcaaaaa cacttaatat gccttatgtg aaaaacaata  73140
ttatttttaa aagcactacc acaaagaaat gaggttggtt ccaaccctcc cagtcaggga  73200
gaagatgtgt gggaatactg aaacaacctt atggaggtca tgtataagaa gattatcgat  73260
actactggat aggtttggtg tcatcacaga aattaaatat gaatatttag acacacatgt  73320
ctgtaagcca gagacattaa gtttaaagca ataatcaact aagaaatttt tctttaaaca  73380
gttgaaaaag caaaaagaca ggctataact aaagataatt taagagggga gaggagtaaa  73440
atccaggtct atttggcttc taagatcagg ctcttgacta ctaatcaaat tgactcctca  73500
gcaaactata ctactgatca atgaaagtga tgaatatttg agtatacaca aaagtagaca  73560
tgaaattcca acagtggcat acagtgaagc taaatgaagt aaagggagca aggttcttag  73620
gcaggagaaa agtgagagga aacaaaatga tcatctttaa agaaggtcat ttcctaagag  73680
acagctgtaa aaaaagaaga gataaataaa aaagacaaaa acattgagct taaattagaa  73740
cagagcttat cacagatcct taaacttgat gaaactgttg cttaagaaag tccagacaac  73800
acataagaat aaaagcattg gtgaacagca agaaaagtca aaatagctgt catacagtgt  73860
aaattgaaga aggaccaaat cagcattgct ttctaatttc catcaaaccc tatcatctgc  73920
caattttcat tactggcagg acactgggct gagtgatttg tctataaaag agaatctctg  73980
gaaagaaaaa ataaatcatg gatgtcatcc aaagaggcta gaccgtatca ttggcaggta  74040
gataagaaag gtcagaggac tgacagaatt tagggcaaaa gaaaagcagc aggacttaat  74100
gtcaagaaat acaaagataa ccagagaaaa gaggctggag ttaaagctta agtgaagtaa  74160
aaggaattaa agctaaatga tgagtaaata cattgaggaa caggggtga attaagatat  74220
gtagcatttc catgtttaaa ccttgcaaaa acttctcatt gcagaccgaa caggacccaa  74280
actccttccc ttgcttataa gcctacatga tctagccttt gttcgccttg atgatgtctc  74340
tactaccctc acctagtagg ctactatgct ccaagtaaat gatgtctcta ctaccctcac  74400
atagtaggct actatgctcc aagtaaacga catgctgtct gttcatgaat catgccaagt  74460
ccactcctca aggtctgcgt agcggtctgt tccctctccc tggaatgttc tttcctctta  74520
tctcgcatga ttggcttctt accattcagt tttcctattc aggaagtata tctggttgta  74580
tctcctagat ggatttttag tgtaaaattt ccagacaagg ttaatgtatc cttgtatcat  74640
catgaaaata atgttgcaac aangaccagc catttaacta tgacagagca ccctaaaagt  74700
gtttcctgat gaaaatcttg gccttcttca cagatactct ctttagtgga tttctttata  74760
atgagataca tgcttttgtt aaatttctca acttttataa aaagaggtca accttactcc  74820
taactcagtc aactatcaca gctactgctc tgccctttag gaagcatcag aaaatacata  74880
tactcaatat gtattatcat tctcataact taagccttag atatgaggta aaataactac  74940
ccttttttaaa gcaattaata tatacaaggc acaatgttat gtgaattcca ttcattgtgt  75000
tcatttaacc ctcataataa cactatgagt ttaagacagt atcattttaa aagcataaaa  75060
agtaacttct gccatgacac acaattagga taggaagaaa tatttataaa agatgttaaa  75120
aaggtgacaa aacatcctat ctgcaatatt ctttaaatta tatccttgga acttaatcca  75180
agattatgat cttcttaaca gatgggtcag aacgctgtgt ggttagaatg cactgtttaa  75240
gatccccaag gaggccaggc acgatggctc acacctctgt atcccagcag tttgggaggc  75300
tgagacgggc agaccacgag gtcaggagtc cgagacaaat ctagccaaca tagtgaaacc  75360
ccgtctctac taaaaataca aaaaattagc cgggtgttat gatgtgcacc tgtaatccca  75420
cctacttggg aggctgaggc aggagaaatc acctgaaccc agaaagcgga gttttcagtg  75480
```

-continued

```
agccaaggcc atgccactgc attccagcca gggtgacaga gcgagactcc atctcaaaaa  75540
aaaaaaaaaa aaaaaaaaac caaagcaaat ataatttagt catttaggcc ttaattttat  75600
accactgact tattttgaag gctgctataa gaaacagccc tatgaaactg gtattttcct  75660
actgcaaggt ggctacttta agacaatttt tcattgcatt ctatcaaggg atgtcttatt  75720
tccttctttg tattgactgt tgaaaaggta tggggccaaa tttgtagttt gtctggaatt  75840
acatattttt gggggtctct attatcttca tacttatcct atctaaattt tccattgcca  75900
aatttcctta cttattttta gttttatcct attgctcatg tatttttatg tctccataag  75960
tctattttgg aaaaaggcag agtactcata attttagtat atcttttagc tttatgttgc  76020
cataaacctt tcattatata catgatcaac aacagcaaat tatctcactt cagtatttag  76080
tttattattt tacaaactga tttatgattg ctaacatgta actgaaggta tacactatta  76140
gaacacagtt ttcagtagaa agtagcactg ccattgagta aaaaaatgtt ctaacattag  76200
agcaacattc ttatacaagt ttgcatgttg tttactgagg tctaaagcat gactacacaa  76260
aaggctgaat aaaattcaga ttcttacata cacataaaat tgttttattg agatgacaaa  76320
gtatatttat tatgccaccc agaatataat ccactctgat aactgccagt gtatgcactt  76380
gctgaagtaa ctcagtacat aaatggtagc cacaacagtt gctgtgcatg aaagttcttc  76440
tcttccagat tgaagagtgt acaatctaaa gcattttaaa actttaaatc ccttattagc  76500
ttaaatataa tttaaaattt tagtttgccg tacctataat ttgtctgtac actaggttac  76560
taagggtgat atgattacat atgtggatac aaaataattt taatggaaaa tgaaattagg  76620
gtactcaaca aagataaagg gtaatgatca tgtacactaa ccgtatttga gattagttta  76680
agcctggggt agctatactt atgtttcaca gaccttgaga agatagggaa aaaaagcttt  76740
tatcaacatt gctaaggaac aggtaaaagc taacattagg taactaagag gtgacataaa  76800
aaagactgaa taaaatatca tggaggtttc ataataagat tggaaattcc atagactagg  76860
agagaaaaga tcccaaaata tacatgctca ttgggaaaac agctagtaag aacaaggaga  76920
gatctctatt taatgataca atagtagagt tataatttcc tgtatattgt aaatttcaag  76980
catttaaaca ttttcattga attataaaat attatttgta aaagaaagaa aaacagcaca  77040
actgcagatt acagatgact aagatagatg aatcatgaaa aggtgctagc agagatttct  77100
atcacaccta tcagggatac acaatttcca agaatttcag aagtgtttgg tgttcctatt  77160
aacataaatc cggaaataac acctgagtga actgtcttct aattcttcaa ctggatggct  77220
ttttagtgta aaagatgttg aatactgatt gactttttaa taattttata gtatatgtca  77280
gaaatattgc acagtcccta tttacatcat tctacagtgg tttttaaaat gttttaagaa  77340
taaaaaacat gaaaacttta tttgattttt ctgaggaaat aacttttttgg atttaatttc  77400
aatgaaaccg ttgataacat ttccctcccc aacaatctct ggcaacgatc cctcagattt  77460
taatgattat gtattattac cttttaatac aagtagaata acactcaggg aatttacaac  77520
atttgttatt ttcagtaaat acattggttg aagtttaaaa gtctatccgt agtaaactta  77580
catctttcag gagcttggtc aatgtgttct ggacaaagca ggaagatgtg actgaaatcc  77640
tgaaaggagc cggctcctgc agcacaagga taatgataca tctgggtaca tttctcttca  77700
cagcatttga tagtggctcc aaagtgctta caaaatgcac attgctgaaa ggggtaaagg  77760
agagaaatct ctttataaaa ccttgaaaag gaatatttaa atataagctg ggaaggtata  77820
aaaaactctc tgtaacatca caagtaaaca aattgaacct gcaaaatatt aaacaaagga  77880
```

-continued

```
ttcattaaaa ataataaaat ctacattact caatttagtg ctttgtgtgc taccaactca  77940
tccttccatt caaattagaa agttagaatt tcattcctta tattttcaaa aataaattgt  78000
gaagcatttt agaaacaaaa cctaaaattt ttttttaaaa gcaaatagta atatggttaa  78060
aggggcaggt ttctatattg aggattatta taaagttttt aaatcctacc aaaactagta  78120
ataggaacat atattattta tgagacatat tactattttt taccctgcct aaaaataaat  78180
acaaataaat tcatcaatta taagttaaca gggacacaaa tggttaaaga ctcacacaca  78240
aaaaaaacaa aactacatac ttcaatgtag caatcaactt caaatttctt aacaaaagat  78300
ggaaatgttg gggaaaaaat tagtcatctg gtatctttcc catttcaacc tgcctccatt  78360
atcttgcaag tggtaaaatg cacagaaata agcctcaaac aagaggggca gtctagggca  78420
agtgaacaca taagtcggaa gaaattatgt aaaatgttgc atttacttat tcagttttcc  78480
cttagaatga ttcacaaact cttcctcatt ctcccaagtc cattttgagt atcattttct  78540
ttgaagagag tctgatgggc cctgtactat acagtatgaa atctctctgt gggaaatgac  78600
tatctaacat aaatttttgt ttacaccgtt acatggtacc tacttgctta tgccattaca  78660
tgatcagttt accttttttct caacctaatc caagatcctt caattgaggc actatactat  78720
ctttgtatcc aaagcaccaa aaatgctgct tcaaacaggc cctaatagat aggtgttcct  78780
atacatatac caaaaagact taacttttgg tgatcttgtt tgtgagtgtg gctcataaac  78840
agcttagttg agataactgg agcctcatgt agcagagaca gttggaccct gctaacatta  78900
ctgtggatat cttcacatgt tactacattg actttatatt ctgctaatta accagggact  78960
acagtagtta aaattataat tgttttcaat gttttatgtg taaatctgta tctcacatac  79020
tatcaaactc ttcctcactg tcatcagtct actgcattga atccaacata acaaagctaa  79080
atgactcctg agggctgaat cagaaagaag aaaagaaaga gatacaaaac tttagtcggc  79140
ccggtggctc acacctgtaa tcccagcact ttggaaggcc aaggcgggcg gatcacgagg  79200
tcaggagatc gagaccatcc tggctgatac agtgaaactc catctctact gaaaatacaa  79260
aaaattagct ggacgtggtg gtgggcacct gtagtcccag ctactcagga ggctgaagca  79320
ggagaagctt ctaaataact cataaacact aattactgtt gtgacacttt aattttatac  79380
aatatttata agtatacaga ataacatttc agtgctattt tggcactcaa gggtattaat  79440
gcattagaaa cacagaaaaa aataaatatt tgtcttcatt gataaagtgt aataaccagc  79500
ttttacaaaa caggtaattt tttatattgt aactcccaag gtatctaaat ttgtttagtg  79560
cattaacaga acccagaatt aactacaaat acaacacctt gatagtctaa atgtccaaac  79620
agaaaggtca cgtaaatgtc gaaagaaaaa gtacaatcaa tctgttgaaa aatgtttata  79680
acagctcatt aacataacta atttctgcta aattgttaaa atctaaaatc gcttattttg  79740
ataccatatg gcaagttttg cagaagcttt ttgcactaaa aataatcttg gcagataaaa  79800
tataatgaga ggtaagtatg taataacaga aaataattta aattgaccag cttctcaatg  79860
tctttctcat tttagaaaca ccaatatgtt ctcttaatca tatctgcaat gaaaaatatt  79920
atattagcta aactattatg aaaagtactg gaatatatct aacatactaa tttacaatat  79980
catataaaga tatcagtgta taaaagaagg aaaataaaac actacattta ggagaacgct  80040
ttaaacccat atgttacaat taaatagcta atgaagagca ctcggcatta aaagaaaatg  80100
tttcctatat atacacagtc tggaatgtat cttcctaaac caaataaaaa gtgcttgtaa  80160
aatcatagac aatatcaaag aatagatttc tacagggaac ttctcaaatg tcaacactct  80220
tatacactac acataaaaga atcaaacaag ttaaaatatt aataatataa taagtaatat  80280
```

-continued

```
ataatacata agtaacaatt acaaagctaa ttaacatttg gggaggaggg atgaagtaaa  80340
cagctcttgg ccgggcatgg tggctcacgc ttttaacccc agcactttcg gaggctgagg  80400
caggtggatc atttgagctc aggagttcga aaccagcctg ggcaacatgg tgaaactcca  80460
actctacaaa aagtacaata attaggtagg catggtggca tgcacctata gtcccagcta  80520
ctcatgagcc tggggtggga aaattgtttg agcccaggag gttgaggctg cagtgagctg  80580
tgatcatgct actgcactct agcctgggca atgaaagtga gaacctgtct ataaaaatta  80640
aaaaaaaaaa gcccttaaat ggtttatcaa ctaaatggtt tatttgaatc aataatgaaa  80700
attcctagac agcatttttt cttttcactt ttattcatca ttaaaaagac acggagtaag  80760
aaaaggaaaa aaagtaacat gttataataa tattttccca tattaatcca agaacacaat  80820
aacaacaaca aaaactcagt gagaactcat attaccaatt ttaagaatga gtctgaggaa  80880
ttttcaaaac ttttatttaa tagattgaaa taatctgtca aaatgtatct ataaaacaca  80940
acagaatgaa caaaatttct gagattaaag ttgtatcatt aaaaaatacc aagaagttaa  81000
atattccaca gttcatttaa ttaattatcc agtatttatt ctgtaccaac tatagcaatg  81060
gttttaggct acgtgctcta ataaataagt attgtaaggc tccccatgct ccaaatttgt  81120
ttttaatctt cactaatctg tttttcgtgt taggcaacta ggattctccc aggatgcagt  81180
aataaagaac aaagatggaa agcaagagaa agaggtagaa tgacatgaaa atctgatcca  81240
gaaggtacaa cgtctgtttt atatgagtac cagaaaggga gaaaatagga gggattataa  81300
tcaccaaaat tctaaaggaa aagttatgta tatatctaat aataaaagct aacatttaat  81360
taaacataat cctcattcaa cagatgagga atctaaaacc caaagagtca ttatcactgt  81420
tccacttatc tctatatccc tacaaaaata ctcactcttg atctgtaaca atgcctcctt  81480
aaactccctg aatggcagct tcaggtaaaa acttcccaga aagtttgaaa caacaagggt  81540
aaaaggaaaa ttcttggaac cacataaaaa agaaaacaga tcattacaaa aaaagaagaa  81600
tcaggcatca gttctcatta ccaatactga attaaaaaga aacccccaaa aaatcattat  81660
tttcctaggt ctataaaaaa ttatttaaaa ccaaaatttt aatgtctgtt aagctaacat  81720
tcaagtccat ggataacaaa tgtaaatggg ttaaattctc tagtaaaaga cagcaacttt  81780
caaaatatgc aaaatatact acttaacaca tacacatatt ttacatgtaa ctatactaca  81840
gacttcattt atgtatgtgt gtgtgtgtac acatatataa tataaaatga atgaaatact  81900
ttggatattt gtccccacca aaatttcatg ttgaaatgta atccccgatg ttggaggtgg  81960
ggccttatgg gaggtgtttg tttgggtcat gggggcaaat ccctcatggc ttggtgctgt  82020
acttgcaata acaagtgagt tctcacaaga tctggttgtt caaaagtgta tggcatctcc  82080
acccgtctcc tttgctcctg ttcttgccat gtgagatgcc tgctccccct tctctttcca  82140
ccattatttc aaactttttt tttaaattta ttatttatta ttattttttt tttgagacag  82200
agtttcactc tgttgcccag gctggagggc aatggcccga tctcagctca ctgcaacctc  82260
caccccccag gttcaagcga ttctcctgcc tcagtctcct gagtagctgg gattacaggc  82320
acctgccacc acacctggct aaatgatttc aaacttcttg aagccctcac cagaagcaga  82380
tgccagcacc acacttcctg tactgtctgc agaatcgtga gccaattaaa cctctttttg  82440
ttatcaatta cccagcgaca ggtatttctt tacaacaaca caggagcggc tgtatatata  82500
tatatattca tacatatgca caatgtacag tgacatacac aattcaaaaa cagccttgag  82560
gggaaaaaac acaaacgcta tccaaaaaat gcaggtatag caataattgc aaagaaacag  82620
```

-continued

```
aatttaaact aaaaagcagt gaataagtca aagataataa ttcacaataa cataagtttt  82680
atgttacagt gtaaattcca aaagaagcca tagtcattaa agtttataca cctaataaat  82740
atatgtcaca tatagaaagt aaagctgagt agaaataaca tgcatagatt agactttaac  82800
atagctctca aatcaggata ttaaatagat atgaaataaa taataacaat gatcgggttt  82860
gattcaaaca gacacataaa atacacacag atctctgaat tccaaaaata gagaaaacat  82920
tctattcaaa tgtacacaga attttcaaaa aaaaattcac atgtatggtc ataaagaaat  82980
gtccacatat tttaaaaagc aggtatttcc taggttatat ccagtaaaag cagatgcgtc  83040
cctagaccta atacaataaa aattagaaat tcacaatata aggataaact cccaaatcta  83100
tccactggca aaatttaaaa gtcctttcta tataacggca gagtttcaat caagaagaaa  83160
aatcatgtat tatttttaaa tgattaagga aacatcaaaa aaatctctga gacgtggcaa  83220
atgtggtatt cagaggaaaa aaatacagct tcaaacatgc aaaactgtaa gactaaagaa  83280
ttacaataaa taatgcccta ttcaaaaatt aagccaataa gaatcaacat ataacccatg  83340
agattcgcta tctagggaag taaacccacc ctaatactgg gtttattaaa atgctgtaat  83400
gagatcggag ggttaaacaa cttttcggtt taggaagtga aataaagctg actgaaataa  83460
aacctaatct atgaaattat tctgtatatg aattgacctg aagtaatgaa cagttcaatg  83520
actgactcat gactcttgtt ctggtccagg ctaatcattc tagttggcat actattaaac  83580
acacatttct gattgaaaca tctgctaaaa aaataacatc aaacgacatt acaaaatcaa  83640
aatggaaact gctaagagtg ggatttttct cctgccagta tctttccttt ctgccacatc  83700
ctcctccctg ctgccacagc aatctttcta aaggaataca aatatattct gaatcacaca  83760
caaacccctc aatacagaat gtgtggtagg cagtattcta aaatgcccgc ataccaccaa  83820
ccccaccaaa tttcctaccc taatacagag gctgtaaata tgatgaaata tcacggcaag  83880
gtaatgccat taatatacta tatggcaaag gaattctgca gatgtgatta aagccatcaa  83940
tcaactgcct ttgaattaat caaaagggag atttgcctaa tctaatcaaa taacctcttt  84000
gaaagcggag ttttatccag ctactagcaa aagggaaatt catagcaagg gaacatttca  84060
gtacactgtt gctatgtttg aagattaaaa gagccaggag caataaccaa agagtggcct  84120
ctaggaactg agggtgaccc aagccaatag gcagtaagaa aatggtgagc tcagcagggt  84180
gtggtggctc atgcctgtaa tcccagcact ttgggaggcc aaggcaggag gatcacgatg  84240
tcatgagatc gagaccatcc tggctaacac ggtaaaaccc cgtttctact aaaaatacaa  84300
aaaaaaaaaa ttagccggca tggtggtgca cgcctgtaat cccggccact tgggaggctg  84360
aggcatgaga atcacttgaa cccaggaggc agaggttgca gtgagccgag actgcaccac  84420
tgcactccag cctgtgcgac agagcaagac tctgtctcaa aaaaaaaaaa aaaagaaaag  84480
aaaaagaaaa tggcaagctc agccctacaa cttcatagaa ctgaattcct cccacacctg  84540
aatgccccag aagaggattc acccccggag cctcacccag gtaacacctt gatttgaatc  84600
ctgtgagacc ttaaacagag agcacagttg agcctgccct gagttctgac ctaagtaaat  84660
gggtgctgtt ttaagatatt aagtttatgg taattgcttt ataataatag ataacaaata  84720
gagcagcatt tcaaggccct ccctgctttg gtctctgcca aatcactatt agatttttaa  84780
gatttttttt tacacattat acttacatta cacaatgtct taacactatg aagtaaaaat  84840
gtaaatattt taaactctgg cttggaaatg aggaggcaga atctcagaaa ttttcctaaa  84900
ataaaatagg agaggcaagc tttctgagtc cacaaaaatg ccctctacct attgggtcaa  84960
agaaaaagta atttctctat ttgtaacaac atacataaat tataaaccct gaagaaatag  85020
```

-continued

```
gtccctaata gctataatct ttaacataac cataaataaa aacatgaata aatctgacta  85080
cataaaaatg taaaaacttc tatgtggtga gaacacacat tacagaaaaa aaatcaaatg  85140
acaaaaaata acctccaatt tggattacaa atatctagta tcctggatat atacaaataa  85200
agcatgtaag ttataaaaat gagtataatt ttaaaataga caaggatact ttatagaatt  85260
tcataattta aggaagacat aaagttagcc aataaactat gggtaatatg caagaatcag  85320
taagcattat tatttgccag cagctaagcc aagtacttta taagaattac tttattccca  85380
tctatgccag gcacagtggc tcacgcatgt aatcccaaca cttcggaagg cagaggtggg  85440
tggatcacct gaggtcagga gttttagacc accctggcca acatggtgag accacgtttc  85500
tattaaaaat acaaaaatta gctgggcctg atggccaggt gcctgtaatc ccagctactt  85560
ggaaggctga ggcaggagaa tcagttgaac ccaggaggta gaggttgcag tgagccgaga  85620
tcatgccact gcactccagc ctgggcaaca gagtgagact ccatctcaaa aacaaaaaca  85680
aaaacaaaaa caaaaacaaa gaaattactt tattcccatc taaccacaac cactttaggt  85740
agatatcact atttttcatt ttacaaatga agcagagagg ttaaatttcc ttgttcaagt  85800
ccatagagtc aggaaatgaa aaaggaactg aactcaagga gttcataatt atttatatac  85860
aagtaataaa gacaaattca ttgactatgg aaatgtactg agtattttgt cttgtttaca  85920
taatggtttt tatttaggtt gtaagaaaat aacatataac caggcacggt ggctcgtgca  85980
tgtaatccca gcactttggg agaccaaggc aggcggatca cttgagacca ggagttcgag  86040
accaacctgg ccaacatggc gaaaccccat ttctaccaaa aaaatacaaa aattagccag  86100
gcgtggtggt gcacacctgt aatcctagct acttgagagg ctgagacagg agaatcgttt  86160
gaacccggga ggtggaggtt gcagtgagcc aagattgcac cactgcactc cagcctgggt  86220
gacagagctg gactttgtct caaaaaaata aaaaataaaa aagaaagtaa gaaaagaaag  86280
tagccacttt ggggttagaa tccataatac tctcagtgtc aaccaaaaga aaggtactgc  86340
aatgttcaca gaacacaatt cataatgacc tcaaattgaa agtcctcaaa atgcccaacg  86400
gtaaaataaa taatttatag tactcttaac aacagaatac tatatatcaa tgagaaaaat  86460
aaacgactgg aaggaacaat ttggatttat ctcataaata tatacgtgaa agatgacaga  86520
aaacagtact tagtagctca attatacgaa gtacaaagcc aattatgcaa agtacaaaca  86580
taggcaagac tcacctatgt tgttactaga tgatagtgca tgtctctggg gagttaggaa  86640
tagcagccaa caggaggctt gaatggaata tctggggcgc tattatttgt ttcctgatgt  86700
gatttagtat ataggttcta atattttggg tattcctaga aatgtgtacc tattattcac  86760
ttgctctata tatagagaga gctatatagc tctctctcta tatatatata tagctatata  86820
tatagcaaag tgaattttat atataattct tcaacatatt tttagaaaaa ttaagttttt  86880
ttagaaaatt aagagaattt tagataaaaa ctcaactttt aatggaaaat attgcctttt  86940
tctttctcac atgaaatcct ctatcaaggt tagtatccta cctggcatct ctccaatact  87000
gggttaagag tttttcttct caagtaacct gtattatatt aagatgatat taactgaaat  87060
aatcagatag atgactgcgc cataaagcta attctaaggt atctgtcctt agccaaaagc  87120
agaaaaggga tacacataac ttccacataa aacatccacc cccatttctt tggttattct  87180
taaaagctca taatgtatac aatgataaaa tttattgttt caaattaggg tttttgaaat  87240
tgaaatatta atttaaacac gtttgcttaa cacaacttta aagttaataa gaaaacactg  87300
catattacag aagagttaaa tacttcaaaa agtgggaaag aatttaaaag ctttcacttg  87360
```

-continued

```
agtaggagta aacacaaaca cactaagaat ctagttggat acacttaaat catgtctttt  87420
aagaacataa gaacagatta tttgctttct ctttagtcca aaaccttggt gtaattttag  87480
tccaaatttg aaactaacag aagaatactc agcttcttaa aagttttatt tcaagaacag  87540
taaaagaact tctggtctta caaacattac acagataaaa cgagtttctc caaacagatg  87600
tatgtaaaaa tctagtacat atacccccaa gttgagtcaa taaggtgaac cagattctgg  87660
ttgaatggaa tccttgaaat ataactttgg tgaacaaact gtttgtgttt tccacttttc  87720
ttaaaaaaga agtgataaag cagatttcca gtaactgcca gctgacaaaa tgctacttac  87780
caggtaaaaa ccactaccaa aaatcagaat cacagaagag ctatcagtaa aattattaat  87840
gccacaaatt aacatgatgt taacagctga tttatgcatc aaaagagtat ttatataatc  87900
acagcaaata actcaaatct tttacatcac tagtaaactc aaaaaatata gcaaaaagca  87960
ataacattaa atttcattat tgatctacta gctttaacta tttaatacta gtacacttag  88020
ttttgattac tttgaaattg aagcaaaaac aataatcttt tcttctttta atgacttttt  88080
cagttatagg aaagatgaca ttaaaagaaa atatacaact atagcttagc tacaggtata  88140
aaattgtttt aaagatatgt aattgtgcta ttgaattaaa ctgaaaacat aactatcaac  88200
tcatgatttt gaaaaaaaat cttttttatg tttggttttg gtaaaaggag agacaaataa  88260
gtcagaagaa cagaaaatac agaaataggc aaactttccc atattcaatt aatttttgag  88320
caaggggcca aggtaattca agagagcaat aaataatctt ttagaatgat gctgaactgc  88380
caaataattc atatggaaaa caaagaaaca tgaatcttat cttgtattct cttatcatat  88440
gtgtaattta accataaatg gatttttaaa cctacaagta acactgcggc aagcaaagat  88500
ttttaataaa gcataaagag cataattttt tcaacttcaa aaaattaaca aatgacaaat  88560
gtcatcaaaa tgaaaccctc tgctgttcaa taaacattgc taaataaatg aaaacaagtc  88620
acacattagg caaaaatatt tataaaatgc atctccaata actgacttct gtgaataata  88680
tataaaaaaa acttagaact caagaagatg acaagcaaat caattggaaa aaaatggtgg  88740
tagagacaaa atctttaaca gacatgtcac caaagataca caaatggcaa aaaaagacat  88800
aaaaagaggc tcaatctaat taatcatcag agaatgcaaa atcaaaccca caataaattg  88860
cactaaatgc caccagatgg ctaaaattta gaaatagtgg caatagccaa tgctggcaac  88920
aatgtacagc aaatggaact ctcagatctc tagaaatgga aaagtataca gacacttttt  88980
aagaaactgc ntgaaactgt tttccaaagt taagaatatt atttccaaca agtcagaaat  89040
tccagtccta ggtatttacc caagaaacat gaaaagatac atctacaacg aagcatgtta  89100
cataaatgct cacagcagct ttatatactg gccaaaaatt gaacgaaact taactgtaag  89160
ctagtgaatg gaccaatctc aaaatgatta tgctaagcaa aaataaggca gatggaaaag  89220
attctatact gtatggttcc attcatatat tagtctagaa aaggcaaaac tataggaaag  89280
caacagatcg gtgattgcca ggagctggag tgggaggtag gcagtaactt caaaaggtca  89340
tgagcgaatt tatgggtaaa gggtctattc tgtatcttga ctatgatggt aattacatga  89400
ctgttcatat ttaccaaatc acattcaata cacaccttag aaagggtgaa ttatagtgta  89460
tgcaaaatat accttaacaa aacaatgact ctacacataa ctttatttat ttattgggta  89520
acagcatagg gactaatatc agaataactt tcctaaaatg tctcaaatct gaagaaaatg  89580
taaaagctaa ctaattgaag ttacctgtaa ataaccaaaa actggctgga atgggaggac  89640
attttaccct tggaaaaaaa gcggaatgtc attggctaaa atctatattt aaatagagtt  89700
tcagtctggg cacgatggct cctgcctgta atcccagcac tctggaaggc cgaggaaggt  89760
```

-continued

```
ggaccaccta aggccaggat tttgagagca gcctagccaa catggtgaaa ccccacctct  89820
actaaaaata taaaaattag ctgggtgtgg tggtgggcac cttatagtcc cggctacttg  89880
agaggcggag gcatgagaat cgcttgaacc tgggaggtgg aggtggctgt gagccgagat  89940
cgcgtcattg cactccagcc tgggcgacag agaccctgtc tcaaaagaaa agaaaagaaa  90000
attctacaac taataagtat agtaatttca atgaaaattt tagtggatgg gcttaacaag  90060
agattggtag aaaattggtc catctccttg aaaatacatg aatagtgtat ctattctgag  90120
gaactaaaag taaaaacact gggaagaaga tgaacagacc ctcagtaatc tacaaaatat  90180
caaatatact aacattcatg taattagagt tacagaggaa gaggagagag aaatgagaca  90240
gaaaaagaat aagaaataaa agtcaagctt ttcacaaatt tggtgaaaaa tatcaactta  90300
cactttcaag aagctcagca acccccaagc aggatgaaca caaagaaaac cacacctagg  90360
cacatcatag tcagactgct gaaaaccaaa gataaagaga aaatcctgaa agcagccaga  90420
gaatatcaaa acattattat atacatggga ataatgatac tactgacacc acacctgact  90480
tcttattaga aaccatggaa gacaggaaac aatgcaacat cttttaaatg cttgaagaag  90540
aaaaacataa tcatcccaga actctatatt cagggaaaaa aaggcaaaaa tgcatgcaga  90600
cttccacttc cagacaaaat gcgagaaaat gtactttccc tgttctttcc actaaataca  90660
gctttaaaaa cccttggcgg tgatacataa gacaaacaaa ggaagacaac aaaatgtaga  90720
gagacggcag accaattagg gcttcaggtg ccaagaaaca caagaggatg aattccctag  90780
gtttcctttc tgactcatat atacaaaaaa gttgctagag aagcagacaa ctcagaaaca  90840
ccaacaggca cacacatacg taaaactcca agaaaattct gctgtctctt gtcaaaaaag  90900
cagggaagcg gcaggctact aagaaaaaaa aaactcacag acaacaacca accagtttaa  90960
gccaaagggg acaaataaaa ccccaagcca tataccttt gcaaagactt aaaaggagga  91020
catagtcagc cattccccac tcctacccac agacaacatg ataccacagc aggccaaggg  91080
gggacacagg acactcatac ccactgagca gcaacgcggc ttcctccctc tagagtggga  91140
gtggaaaaaa agtggggagc ctgagttcaa cacccaccca atgagaaggg catattccta  91200
tccctccctc tacagagata tgacagcaga ggcctactgg agaatccaaa ctcaaagcac  91260
tgctcagtga taacttaacc acccctccat cccagtgtca gtggaggcca agtgaaaagc  91320
aggaaccttt tgagccaggg tggtattcac aaaggtataa tgcaagtcca gagttttcat  91380
tcctactcag catttactag gtgtacgtct ccatcaatga gtcaacaaag gcctactatg  91440
aaactggaat cttcacatac acctggggt agtaacaagg ctatgcccca cctccacccc  91500
aaaagcaaat tttcagataa atcctactaa aagggggat ttaaataaaa tgcagagctt  91560
cataacacaa cacttaaaat gcaaaggatt caaccaaata taacatgtca taccatacta  91620
agaagcagga aaatctgaac aggaatttga aaatatagtc aaaaggtgca aacaatgagt  91680
attcatagat gtcataatta tctatcaaag attttaaact atatattata aaactgcttc  91740
aacaagcaat tacagccaga cacagtggct cacgcctgta attccagaac tttgggaggc  91800
agaggtggtt ggatcacttg aggtcaggag ttcgagacca gcctggccaa catcgtgaaa  91860
ccccatctgt actaaaaata caaaaattac ccaggcatgg tggttcacac ctgtgattcc  91920
agctactcgg gaggctgagg catgagaatc acttgagccc aggaagcaga ggttgcagtg  91980
agctgagatc attctactgc attccagcct gggcaacaga gcaagagtcc gcctcaaaaa  92040
aaaaaaaaaa aaaaaaaaag caataacaaa cataattttg aaacaaagga aacaatacaa  92100
```

-continued

```
tgtttcgcat agaaatcaag aaagaaacaa ataccaagtt gaaaattaaa aaatatgcta  92160
gcaataataa aatacaaact aaagctgaac acaaaatggg ggagattacc caacctagag  92220
aagaaaatga actgattaaa aaaaaaaaaa agtggccagg tgcggttgct caggcctgta  92280
atcctagcac tttgggaggc cgagatgggt ggatcacctc aggtgaggag ttcaagacca  92340
gcctggacaa catggcaaaa ccctgtctct aataaaaata caaaaattaa ctgggcatgg  92400
tggcacacac ctataattcc agctactcag gaggctgagg caggagaatc acttagaccc  92460
aggggcggag gctgcagtga gctgagattg taccacttca cttcagcctg ggcaaaagag  92520
caaaactctg acaataaata aacaaataaa tatatatata ttttttaaaa aaaggcatta  92580
aagacacttg tggtactata ataaatgatg caacattcct gtcactggaa tctcagaaaa  92640
ggaacatgat gcagctgaac aattattcga agacccacag attcaagaaa ttgaataaat  92700
cctaagagga tacacacaaa taaatcaatg ctaatatata tcataaactt ntgaaaacta  92760
atgactaaac ttaaaaacct tgngataaat aagagaaatg acaccttatc cacagatgaa  92820
aaacaactca natgacagca gatttctcac ccgaaaccat ggaggccaga acaaagcagc  92880
ataacatttt tgtaagtcct aaaagaactg acaacaaaga attctatatc cagcaaaaac  92940
atccattagt aatgaaaggg aaatcaagaa tttgtgagat gaatgagaac taaaaattag  93000
tcatgagaca aaactacacc aaaagaatag tgagaaaagt tattgaacca gaaaggagaa  93060
tgataaaaag aaggattctt agaacatcct gaaggaagaa agaacaaaca aatagtaaaa  93120
ctatgggcaa taaaacagac tttactcttc cttgagtttc caaaataatg tttaacaatt  93180
gaagcaaaaa ttgttacatg atgcaaaagc tatggtgggt aaaactgttg atgcatttcc  93240
aaaactgaag gcagctggca ccaagctgta ttagaagttg tcacattctc aactggtact  93300
acaactacag taaaaataat gtagagtatc attgagaata tcactgatga agcagcaaaa  93360
atctttaatg ctttaagtct tgatccatga atacaccatc ttttaattat ctatgtgaca  93420
aaatgagaaa tgaagcgtaa aataattgtt acaccacagt tttcttgag gaaagaattt  93480
gtgatcatgt gatttataaa ctgaaataac ctgctttttt aatggaacac tgtttttaca  93540
tgtaagaaca actaagaaac cacaattatt aaaacttgat tatctgacat atttcttcaa  93600
aaatgaataa agtgagcctg ccacttcaag gaaaacaact aacatgagtg gacaataaga  93660
agatttgaaa accttacaac caacaatgta agcttaacta attccaatac ttaaagactt  93720
ttctgatgag agcagttgat tataacaaat gtgaattttt gttattaact aaaaatgtgt  93780
agggactagg taagctggct acacttgtaa tcccagcact tcgggatcac tggaggtcag  93840
gagttcaaga caagcctagc caacatagtg aaaccccatc tctactaaaa atatgaaaat  93900
tagctgggcc tggtggtgca tgcctatagt cccagctact caggaggctg aggcatgagc  93960
atcacctgaa cccaggagac ggaagtgagc tgagatcgca ccactgcatt tccagcctgg  94020
gcaacagagt gagattctgt ctcaaacaaa caaaacaaaa caaaacaaac aaacaaaaac  94080
aaccgtatca atagttggaa tatctggatc actcagtgaa ccaatatttt ccaaagacca  94140
cttagtaatc ttataaaatc atatatgggt aaaagatccc ctgaaattgc aaggtagtct  94200
aataaattat atatatatat atatatatat atattttgtc tcagagataa agtctcactc  94260
tgttacccac gctggagtgc agtggcacaa tctcggctca ctgcaacctc cacctcctgg  94320
gttcaagaga ttctctgcct cggcctcccc cgtagttggg attgtaggtg cctgttacaa  94380
tgcctggcta atttttgtat ttttagtaga gacggggttt cacaatcttg gccaggctgg  94440
tcttcagctc ctgacctcgt gatccaccca cttcagcctc ccaaagtgct gggattacag  94500
```

-continued

```
gcgtgaacca ctgcgcccag cccataaatt ataattttaa aggataaaga tataaagttc  94560
attgatggga ttgcagtctt cagactgcac caaaccactt gaaaaacttg agaaactacc  94620
acttctcaag ctttggtttt agtatcaaac aggaatattc attagggctt gtgctttcat  94680
tcttacagta tattttaata aacagaagtt atttctcaaa tgtagttgaa tgctccaata  94740
ttttccttta cgttcagtgc tgtatctcaa gaactctttt acaaaaatat tatcctatat  94800
tatcttttta agtataaata aaaataatta tctttttaaa agcttatgag tttaggtgga  94860
aatatgaagg gccaaaagga attggaagac attttcctac tatttgttct ttctcttgat  94920
tttcatgatt cattattctt gtagaagtga ccttaccaca gtataaggtt cacttataat  94980
cactgttctg ccttgtaatt ttaggtgaat ttgttacaaa atattatgaa atctatagga  95040
aaagccaact ttcaaagcta ttaagcattt gacttaacag ttgagggcaa tattattcag  95100
aaaaatttca atctcattcc tcagcgcaaa aaactgaaat aaaactttac cactgccaag  95160
tcagtaaatt gctatgtaga atggcaattc agtatattct gcctctatat ctaacaaaaa  95220
ttcataggat ttgatgatga agtccacaaa tgccagtcaa aatcactgct gacactatta  95280
tataatagtt cactaaaaca tgacagattt aaatattttc tgcaaagtac ctgctaataa  95340
ataatacaat aaataatcag gctttaaaca cctgacattt aacaagcttt gtaaatttgt  95400
ccaactcaag tctttctgct ccacagttat ttttgccact atcaactgta acacatctta  95460
gcggattcca cttcaggttg tactaagtta gtgtttgctc aacttttctg aaaatatttt  95520
ctcttgtagt tgtttcacat agactatgca taaacactaa ttcttcggca tcttcaaact  95580
cagcactgac ttctggaata tgtaacaact gaacagtact ggtactggta acacctattc  95640
atccatcaaa agcctaagaa actccatgaa aaatcattca cccttctttc caaaatggct  95700
tgatattact cccaatgtcc ttaactttta gagcaattac tctcgctgaa aggttaatag  95760
tctttttaaa agtttatttt ctatggacac atctttggtt accgtaatga aacataattt  95820
aattacctcc tgttggtcat ggttttcctt ccttggctca cacatcagcc attgaaaaaa  95880
cttactttaa ttatagccta atttccattt tttgtttttg agaagaaatt ctgctgtgat  95940
aaaattttgt tttaatttac tatttttttt cctacctttt agttaagtta atccctgtgg  96000
ttgggaaaat tgtaaaagtg cccattctgg caatgttgcc atatataata ttcttttagc  96060
cagccatagt cttctagcat aaccaatata atgcttttgc tatctaattt gttaataata  96120
atatacattc cactatgcca ataaagtgtt acatataaag tccacttttc tccttttctt  96180
gttttaacat gataggtaag tatgcactgg taatgagaga aataaataag atgccagggc  96240
aatatgtgtg gtgcacacac acacacacat actgacaaac agtaactatg tcattgtgat  96300
tcgtagcatg cagagcagca atttgaaata tatgtgctct ctgcagcaac caactctgac  96360
actgtagtgc aacggaagtc atatataatg cccaaacaat tcagggaaag gaaaagtcac  96420
gtgcctctca ttttaactga aaagctacaa atgattaatc ttagtgggga aggaatatca  96480
aaaagtgaga aaggcctaaa gctaggcctc ttgtaccact cagacaatta tgaatgtaaa  96540
cgaaaattct tgaataaaat taaaagcact atgtcagtga acatgaaaca atcttattgc  96600
taatatgaag aaagttttag tggtccatat gaaagatcaa accagccaca acattccctt  96660
aagcaaaaaa cctaatccac agcaaggctc taagcttctt cagttctatg aaggctgaga  96720
gaggtgagaa aactgcagca gaaaaactgg aagcaagtag aagttggctc atgaggaaaa  96780
atgctcttgt cataacataa aagtggaaag tgaagcagca agtgctgaca tggaagctgt  96840
```

-continued

```
agcaagttat ccagaatatc tatctaagat cattgctgga ggtggctata ctaaacaagg  96900
tgttttaagt agacaaaaga gccttccatt agaagaagat gccatctagg actttcacag  96960
ctagagaggg aaaatcaatg ccttgcttca aagttcaggc tggggccaca cctgttattc  97020
cagcactttg agaggccaag gtaagagaat cacttgagcc ctaggagttc aaggccagcc  97080
tggacaaaaa ggcgagactc ttgtctcttt taaaaataaa taaataaata aataaataaa  97140
taaataaata aaaactgact ctcttgttag gggctaatgc agctggtaac ttgacgttga  97200
agctaatgct catttgccac tcaaaaagcc ctagagctct taagaattat gctatatcta  97260
atctgcttgc tatctacata tggaacaaca gtctcctgga tgacagcaca tctgtttaga  97320
ggttggctta ctgaatattt tcagtccact gtcaagacct actgctaagg aaaaaacatt  97380
aatttcaaaa tattagcact cactaacaat ggaccaggtc attagagggc tttgatggat  97440
atgttcagaa agaagaatgt tactttcatg cctgccagta caatacaaca tctatcctgc  97500
agcccatgca tcaatgagta atttcaattt ttaagtctta ctgtttaaga aatacatttc  97560
agccaggcac ggcagctcat gcctgtaatc ccagcactct gggacacaaa ggcaggagga  97620
tcacttgaag ccgggagttc gagaacaccc tggccaacat ggcaaaaccc catctctact  97680
aaaaatacaa aaattagcca ggcgtggtgg cacccacctg tagtcccaga tactcggggg  97740
gctgagtcag gagaatcgct tgaaccggga ggcagaggtt gcagtaaacc aagatcacac  97800
cactgcactc cagccaggct gagaaagcga gactccatct caaaaaaaaa agtgattcct  97860
gtagtagatt tgggcaaaat aaactgaaaa ccttctggaa aggcttcacc accgtagatg  97920
tcattaagaa cattcataat tcatgagagg aagtcaaaat atcaacatga acaggtgttt  97980
ggaagaagtt gattccaact ctcatggatg actttgagag gttcaagact caagtggagg  98040
aagtcactgc agatgtagtg gaaacagnat gagaattaga agtggagcct gaagatgtga  98100
ctgaattgct gcaatctcat gataaaactt gcacagatta ggagttgttc cttacagatg  98160
ttgaatgaca acaaaggatt tagaatacta tataacgtta gttgttaaag cagtggcagg  98280
gtttgagctg actccaattt tgaaaaaaag ttctactttt gggtaaaaaa tgctatcaaa  98340
cagcatcaag tgctacagag aaatctttca tgaaagaaag aggcaatcaa tgtagcaaac  98400
ttcattgttg tcttattgta agaaactgcc agaggcaccc caaccttcag caatcactgc  98460
tggcatcagt cagcagccac caacatcctc tatcagcaaa aaatcttaca atttactgaa  98520
agctcagatg atcagtagca ttttttagca ataaagtatt tttaaattaa agtatgcaca  98580
ttggtttttt aaatataacg ctattgaaca tttaatagac tgaagtagaa tataaacata  98640
atatttacat acactggtaa accaaaatat ttgtggcctt gctttatggt gatattcact  98700
ttattgtggt agtctataat ggaacctaca gtatctccaa aggtatgctt tgtatttacc  98760
tttggtacca aattctagat atacatctgc atatacctgg gtatttaact tcctggtctc  98820
atgttcctta aatagttaat aagaaagagt aattatgaac catgcagacc aattaacaag  98880
cctaacttcc aatattttct tcactctgaa ataagtattt ccaacattgt attatgtcag  98940
aagttctcgg ttttgggggt gctgtatctt aatttttctg tactctattt tcaacttcac  99000
tgacataata caagctctat cttccttaca aatttataag gaatcaaatg aaatgaaata  99060
tataaaagtt gtcctctttc tcccatcttc aaaaaacttc cccctgcatt tcatttcctg  99120
ttagccctct ctccttcaac agcctggtct gtagaaagag tccatacatg gcctccctcc  99180
actccctcat cttccattca ctccttgttc caaggccttc ccaacaccac tgaaactttt  99240
ttcaatgccc tttttttaat ttttttttaa aagcaaattc tgcccccaac ttttcattct  99300
```

-continued

```
ttcagttgaa ccactttttc caagacactg cagatgtaaa aaatacgtag ttaaggccag  99360
tgtccagtgg ctcatgcctg tattcccagc actgtgggag tccaaggcag gaagatcaca  99420
ggtctggagt tcaagaccag cctggtcaac atggtgaaac ctcatctcta ctaaatatac  99480
aaaaataagt caggcatggt ggcaggcacc tgtaatccca gctactcagg aggctgaggc  99540
aggagaattg cttgaaccca ggaggcggag gttgcagtga gccaagatcg caccattgac  99600
tccagcctgg ggcaaaaagc aagactgtgt gtgtgtttgg aggggggggac ctgttaataa  99660
aaagaaaaga aaacaactca atttcaaaat gggcaaagga ggcctgccat ggtggctcct  99720
atctataatc ccagcacttt cagaggccaa ggcgggtgga tcacctgagg tcaggagttc  99780
aagaccagcc tggccaacat ggcaaaatcc cgtctctact aaaaacacaa aaattagcca  99840
ggcatggtgg tgcacgcctg tagtctcagc tactcaggag gctgaggcag gacaatcacc  99900
tgaacccaga aagtggaggt tgcagtgagc cgagatcatg ccactgcact ccagcctagg  99960
tgacaagagt aagtctctgt ctccaaaaaa aacaaacaaa aatgggcaaa ggagccaagc 100020
atggtggtgc acacatagag tcccagctac tgagaggctg aagtaggagt atcacttgag 100080
ctagaggatc acttgacccc aggagttcaa ggctgcagtg agctagaact gtgccactgc 100140
aatccagcct gtgtgacaga gtaagactcc aaaaaagaca agggcaaaga catgacgaga 100200
gagaaaaaat aagtataaaa gtaaagacag agagagagag acttcaaaga ggaggacagg 100260
gcaagacaca gtggcccatg cctgtaatcc cagcactttg ggaggctata atgggaggat 100320
cacttgagcc catgggttcg agaccagcct aggcaacaca gcgagacccc agtatctaca 100380
aaaactagcc gggaatggct gggcatggtg gctcacacct gtaatcctag cactttggga 100440
ggccgaggca ggcggatagc ctgagctcag gaattagaga cccgctgggt aacaaggaga 100500
aaccccatct ctactaaaat ataaaaactt agccaggggt ggcagcatgc acctgtagtc 100560
ccagctactt gggaggctga ggcaggagaa tcacttgaac ccaggaggca gaagttgcac 100620
gtgagctgag atcacaccac tacactactg cactccaggc tgggcaacac agctacgact 100680
ccctctcaaa aaaaaaatgt aaaactaagc tgggcacagt ggctcacacc tataatccca 100740
tcactttggg aagccgaggc aggcaagatc acctgaggtc aggagttcaa ggccaacctg 100800
accactatga tgaaacccca cctctactaa aaactcagaa attagctgag catgggggca 100860
tgcgactata atcccagcta ctcgagaggc agagacagga gaatcgcttg aacctgggag 100920
gaagaggttg cagtgagccg agatcacacc attgcactcc agcctgggca acaagagtga 100980
aactctgtct caaaaaaaaa aaaaaaaaaa aaaaaactag ccgggcacag tattgtgcac 101040
ctgtattccc agctacttgg gaagctaaga tgggagggtc atttgggccc agaaattcga 101100
agctgcagtc aactatgatt gtgccaccgc gctcctgtct aagtaacaga atgagatatt 101160
gtaatttaaa aaataaaagg ataggtagga tttaccgact gaaagatgag agtggaaaaa 101220
ggaaggaggg atagcaagaa tggcgggcag gtagacagaa aggtaaaatt cagccatgtt 101280
caaaagggaa caaataaaag cattgaaagg taagacagac ctagtatatt tatgacttga 101340
atcccaagct aagaaactgg aacataattt agcagagaga ctccaaaagt tttacagcaa 101400
aaagtattag aatcatttat atactgggaa aaaatagcct cctcatttta ataatccaga 101460
ttgggaaatc agatctaaaa cagatgttca atggacatcc catttctttt gtaaaagcaa 101520
cttgaaaggt cagacagcaa gttgtgttct gtttttaatt cacaatgaaa atctgactac 101580
tcatttattc aacaaatatt tgagtaccag ctatgtgcta ggcactgttc taaacacgcc 101640
```

-continued

```
aataacattt atttagtggt actgattctg tactctagaa caatggttct taactgggga 101700
gagggagcaa tttttgctgc ccaagggaca tctggcaatg tctaaagata tttttggttg 101760
tcacaggggc aggggggagg ggaggggcgc gggtgtgcta ctatatctag tggatggagg 101820
ccagaaatgc tgcttaacat cctacacaca ggatatactg cccgtgacaa ggaattagct 101880
agcccaaaat gtcaatagtg ccaaagttga ataaacctgt tcaagagcaa cacatttcta 101940
acaatagagg ctttaaaata tcttaagaaa tgtaacacca ttttaataat ttggcaagta 102060
gaagtaaaga taccatgaat cctgagattt cactttcaaa aatgtattaa gctacattta 102120
ttttacaata aaacttttag gaacaaagtt gtcttctcct tcanacactg ttctcaaaaa 102180
ctgtgctaaa agccttgagt aatgtttgat aactcctttt attttggggt ccttatagct 102240
gttaataacc acattctgcc agttctttcc atgtgaatgc ctcacatttc aatggatctt 102300
tttatatacc aatgtattat cttgaaacat tttactaact ggtttttctg aagctcaatg 102360
tccttgtctc cttccctccc aagctatccc tacccattaa tactgtactt ttcacctgct 102420
caaaagtcca tatggttgcc tgtaacatac caaataagaa cctaattcct aaagcttgac 102480
attcaaatcc tttttcaac tagctacaat ccacttttcc aactcttttt tccactgctc 102540
tcccttagga gtagcctttt ttagcaaaat gacttattct gagatacaca aataaccttt 102600
ccagatcaga gacatcaaaa gccattcagg cttcactgag acaaaagata tgcacacaac 102660
tcagaataac agtaaggaat caacttatag ggaaaccaga tgtagccatg ctctttaaat 102720
attgagagat aaccccgttg gctcatgcca ctgtccttat atataacagc ccgtatttgc 102780
ctttctactt ttctgatctc cttatacttc aaatgtacaa tcttttcaaa aacccaaaca 102840
cagagtcacc tcagtcacca ctnnttgccc ttctcctacc gcacccaatg cctgnggctt 102900
tcaggtcatt tattttgcan taaacttgtt atctcaattt tactggttct cttttagatt 102960
cagacagctg agattatgat agattcatta gtaagctgaa tggggaagga aaggatattt 103020
acattcccag gccaattttc aatgcttttt ggaagattct gttaaattca taatttccag 103080
aactggcaag gaataggtaa atatatacac tcatatataa ctggtaagac tataaattgg 103140
tataattatc ctacagtgat atctgccaac attgaaagtc tttaaaatct gtataccctt 103200
tggcctagga attcaacttg aaaatttatc atgagtaaat tataaaatgt acaaaggttt 103260
aactataaag acactcatct ctgcattgtt tctaactctc aaagattgag ggggagggga 103320
aaatcccttg tccaataaaa aaagactatt ccatgaatca tttatttaag taatgtaata 103380
ctttgcaact actaaaatcc tatagtatca tggttattga catgtaactc ttttaatggc 103440
tttctttcct aagctaaaaa aatacaaaca tgattccaca taatgtattt caaaaattgg 103500
tatacatttt tctacttttc tatattttct acacatctat atataatttg tgtgtgtgtg 103560
tgtgtgtgtg tgtgtgtgtg tgtgtatgca tgcatgtaaa taaaatatac ctctaagtct 103620
ttgtaacctt aagatggtgg agcaaaatat ttttattttc tgttgttgat tatttaaaat 103680
ttagctatat taaatctttt ctgatttagt aaacatacat aaggcctatt tatagttgaa 103740
tggcagtctt acaaaaccta agcaaccttg gtttactcta tctgtgggaa aagcattttt 103800
agtagaatgc ttgcgcatct tcctacattc ctgaatcaac cagtatttat catcaactat 103860
aaagctaagg ggaaggatag gaaaccggga aaccccggga aaggagggat tatattacac 103980
atgttatggg aactagtttg tatgtgcggg gcacagagca tacacttaga taagaagggg 104040
gtcataaaac cagaaaggca ataaatagaa tgttatgagc atgaactcta gacgcaaact 104100
gttcaggttc aatctcacct ctgcttctta ctacatttat taccttaagc aagtcactta 104160
```

```
acttctccct gccgtttctg ccacatctgt ataatgggga taacagaccc taccttagag 104220
ggctgtcaca ctaatgaatt ctgagaatag tccctggtac tacagttaag tgctcattag 104280
ttgtccacac tcatcatctt cattactccc attactatga tgtgaagagt tgtgctgtta 104340
ggacgggaga agcaactttt caacaccaat cactttttta gacggcctcc tttctagcct 104400
tgttagttgc ccaaattctg aaaaaaacaa gaactaagac tctagaagga gatccgagag 104460
gcagacgtgt gtctctgtgt gtgtttgtgt gtgtgtgtag gtgcgtgtgc atgtagacga 104520
aggaggaatc aggagtaatg ccaagaatga gaatcaaatc tgtataagca gttcagaaaa 104580
ggggcatcat gagtcgctct tctcagtgct gccccaaggg ttccacagtt tgctccttcc 104640
atcattcact tggataaaac ctttcaatgt ctctccatgg ccttcagagt taaatcaaaa 104700
ctattccttg gaatgactta aaacccatac tatctctaaa gcctcatctc ttggctctct 104760
cgcaccaagc tcactgagct tccagcccta ccaaatttct tcagtaacaa cctctcacat 104820
ctcagagcct ttgcatatgc tgctccctct gcctgaaaag taacctctac ctcctccaat 104880
agcaaactgc tactcaacct tcaaaacaca gctcaaggat aactccagag ctctttcgtg 104940
atttcaagct aaatgactct gctatattat cccccatgtg cataacacca ccactaccac 105000
caccaccatc accactaaaa ccacgaccac cactactcac gcactaccac caccaccacc 105060
accaacacca acaccaccac catgaccact accactacca ccaccaccac catcaccact 105120
actcaccacc accactacca ccaccaacac caacaccaac accaccacca tcaccactac 105180
cactaccacc accaccaaca ccatcaccac tacgaccacg accaccacca ctaccaccac 105240
caccaccacc actaccacca ccaccaccat caccactaaa accacgacca ccaccaccac 105300
catcaccacc atcaccacca ccaccaccac catcacgcac caccaccacc accaccatca 105360
ccaccaccac caccatcacc accactatca ccaccaccac aatgaccagc accaccatta 105420
gcaccagcat caccacgagn nnnnnnnngg ttcaagcaat tctctgcctc agcctcccaa 105480
gtagctggga ttacaggtgc ctgccaccat gcctggctaa tttttgtagt tttagtagag 105540
atggggtttc accatcttag ccaggctggt cttgaactcc tgacctcgtg atccatctgc 105600
ctcagcctcc caaagtgctg ggattacagg cgtgagccgc tgttcctggc agagattcta 105660
agtttttgga gaatagtgac tgtgtttctt gggtcatggc tctatcttat acatttggca 105720
cagtgtgtgt gtgtagcagg tgtttaatat ttgttaaaca caagtggtcc ttaatatcaa 105780
aataccacaa actgagtgac ataagtgaca ctattttttt ttttttgaga tgcagtctca 107160
ctctgtcacc aggctgcacg atctcggctc actgcagcct cggcctccca ggttcaagtg 107220
attctcctac ctcggcctcc cgagtagctg ggacttccag cctccagaat tgagaaattt 107280
aatttctttt aattttaaaa aattaagagt gacacttggc cgggcgcagt ggctcatgcc 107340
tataatccca gcactttggg aggctgaggc gggcagatca cgaggccagg agatcgagac 107400
tatcctggct aacacagtga aaccccgtct ctactaaaaa tacaaaaagt tggtcgggcg 107460
tggtggctca tgcctgtaat cccagcactt tgggagtccg aggtaggcgg ataacctgag 107520
gttgggagtt tcagaccagt atgaccaaca cggagaaacc ctgtgtctac taaaaataca 107580
aaattagctg tgcatggtgg tgcatgcttg taa                             107613
```

<210> SEQ ID NO 2
<211> LENGTH: 11162
<212> TYPE: DNA
<213> ORGANISM: Artificial Sequence
<220> FEATURE:

-continued

<223> OTHER INFORMATION: Gene vector using TK as negative screening gene.

<400> SEQUENCE: 2

```
gggcgaattg ggcccgacgt cgcatgctcc tctagactcg aggaattcta ccgggtaggg     60
gaggcgcttt tcccaaggca gtctggagca tgcgcttaag cagccccgct gggcacttgg    120
cgctacacaa gtggcctctg gcctcgcaca cattccacat ccaccggtag gcgccaaccg    180
gctccgttct ttggtggccc cttcgcgcca ccttctactc ctcccctagt caggaagttc    240
ccccccgccc cgcagctcgc gtcgtgcagg acgtgacaaa tggaagtagc acgtctcact    300
agtctcgtgc agatggacag caccgctgag caatggaagc gggtaggcct ttggggcagc    360
ggccaatagc agctttgctc cttcgctttc tgggctcaga ggctgggaag ggtgggtcc     420
gggggcgggc tcaggggcgg gctcaggggc ggggcgggcg cccgaaggtc ctccggaggc    480
ccggcattct gacgcttcaa aagcgcacgt ctgccgcgct gttctcctct tcctcatctc    540
cggcctttcg acctgcagcg acccgcttaa cagcgtcaac agcgtgccgc agatcttggt    600
ggcgtgaaac tcccgcacct cttcggcaag cgccttgtag aagcgcgtat ggcttcgtac    660
ccctgccatc aacacgcgtc tgcgttcgac caggctgcgc gttctcgcgg ccatagcaac    720
cgacgtacgg cgttgcgccc tcgccggcag caagaagcca cggaagtccg cctggagcag    780
aaaatgccca cgctactgcg ggtttatata gacggtcctc acgggatggg gaaaaccacc    840
accacgcaac tgctggtggc cctgggttcg cgcgacgata tcgtctacgt acccgagccc    900
gatgacttac tggcaggtgc tgggggcttc cgagacaatc gcgaacatct acaccacaca    960
acaccgcctc gaccagggtg agatatcggc cggggacgcg gcggtggtaa tgacaagcgc   1020
ccagataaca atgggcatgc cttatgccgt gaccgacgcc gttctggctc ctcatatcgg   1080
gggggaggct gggagctcac atgccccgcc cccggccctc accctcatct tcgaccgcca   1140
tcccatcgcc gccctcctgt gctacccggc cgcgcgatac cttatgggca gcatgacccc   1200
ccaggccgtg ctggcgttcg tggccctcat cccgccgacc ttgcccggca caaacatcgt   1260
gttgggggcc cttccggagg acagacacat cgaccgcctg gccaaacgcc agcgccccgg   1320
cgagcggctt gacctggcta tgctggccgc gattcgccgc gtttacgggc tgcttgccaa   1380
tacggtgcgg tatctgcagg gcggcgggtc gtggcgggag gattggggac agctttcggg   1440
gacggccgtg cccgccccag ggtgccgagc cccagagcaa cgcgggccca cgaccccata   1500
tcggggacac gttatttacc ctgtttcggg cccccgagtt gctggccccc aacggcgacc   1560
tgtacaacgt gtttgcctgg gccttggacg tcttggccaa acgcctccgt cccatgcacg   1620
tctttatcct ggattacgac caatcgcccg ccggctgccg ggacgccctg ctgcaactta   1680
cctccgggat ggtccagacc cacgtcacca cccccggctc cataccgacg atctgcgacc   1740
tggcgcgcac gtttgcccgg gagatggggg aggctaactg aaacacggaa ggagacaata   1800
ccggaaggaa cccgcgctat gacggcaata aaaagacaga ataaaacgca cgggtgttgg   1860
gtcgtttgtt cataaacgcg gggttcggtc ccagggctgg cactctgtcg ataccccacc   1920
gagaccccat tggggccaat acgcccgcgt ttcttccttt tccccacccc accccccaag   1980
ttcgggtgaa ggcccagggc tcgcagccaa cgtcggggcg gcaagccctg ccatagccac   2040
gggccccgtg ggttagggac ggggtccccc atggggaatg gtttatggtt cgtgggggtt   2100
attattttgg gcgttgcgtg ggtcaggtc cacgactgga ctgagcagac agacccatgg    2160
tttttggatg gcctgggcat ggaccgcatg tactggcgcg acacgaacac cgggcgtctg   2220
```

-continued

```
tggctgccaa acacccccga cccccaaaaa ccaccgcgcg gatttctggc gccgccggac   2280
gaactaaacc tgactacggc atctctgccc cttcttcgct ggtacgagga gcgcttttgt   2340
tttgtattgg tcaccacggc cgagtttccg cgggaccccg gccaggacct gcagaaattg   2400
atgatctatt aaacaataaa gatgtccact aaaatggaag tttttcctgt catactttgt   2460
taagaagggt gagaacagag tacctacatt ttgaatggaa ggattggagc tacgggggtg   2520
ggggtggggt gggattagat aaatgcctgc tctttactga aggctcttta ctattgcttt   2580
atgataatgt ttcatagttg gatatcataa tttaaacaag caaaaccaaa ttaagggcca   2640
gctcattcct cccactcatg atctatagat ctatagatct ctcgtgggat cattgttttt   2700
ctcttgattc ccactttgtg gttctaagta ctgtggtttc caaatgtgtc agtttcatag   2760
cctgaagaac gagatcagca gcctctgttc cacatacact tcattctcag tattgttttg   2820
ccaagttcta attccatcag aagctcctta attttatacc actgacttat tttgaaggct   2880
gctataagaa acagccctat gaaactggta ttttcctact gcaaggtggc tactttaaga   2940
caatttttca ttgcattcta tcaagggatg tcttattatt atatcattat atcaagtgat   3000
gttataaata gtaagaatca gattaagggc tcatatgtcc ttctttgtat tgactgttga   3060
aaaggtatgg ggccaaattt gtagtttgtc tggaattaca tatttttggg ggtctctatt   3120
atcttcatac ttatcctatc taaattttcc attgccaaat ttccttactt atttttagtt   3180
ttatcctatt gctcatgtat ttttatgtct ccataagtct attttggaaa aaggcagagt   3240
actcataatt ttagtatatc ttttagcttt atgttgccat aaacctttca ttatatacat   3300
gatcaacaac agcaaattat ctcacttcag tatttagttt attattttac aaactgattt   3360
atgattgcta acatgtaact gaaggtatac actattagaa cacagttttc agtagaaagt   3420
agcactgcca ttgagtaaaa aaatgttcta acattagagc aacattctta tacaagtttg   3480
catgttgttt actgaggtct aaagcatgac tacacaaaag gctgaataaa attcagattc   3540
ttacatacac ataaaattgt tttattgaga tgacaaagta tatttattat gccacccaga   3600
atataatcca ctctgataac tgccagtgta tgcacttgct gaagtaactc agtacataaa   3660
tggtagccac aacagttgct gtgcatgaaa gttcttctct tccagattga agagtgtaca   3720
atctaaagca ttttaaaact ttaaatccct tattagctta aatataattt aaaattttag   3780
tttgccgtac ctataatttg tctgtacact aggttactaa gggtgatatg attacatatg   3840
tggatacaaa ataattttaa tggaaaatga aattagggta ctcaacaaag ataaagggta   3900
atgatcatgt acactaaccg tatttgagat tagtttaagc ctggggtagc tatacttatg   3960
tttcacagac cttgagaaga tagggaaaaa aagcttttat caacattgct aaggaacagg   4020
taaaagctaa cattaggtaa ctaagaggtg acataaaaaa gactgaataa aatatcatgg   4080
aggtttcata ataagattgg aaattccata gactaggaga gaaaagatcc caaaatatac   4140
atgctcattg ggaaaacagc tagtaagaac aaggagagat ctctatttaa tgatacaata   4200
gtagagttat aatttcctgt atattgtaaa tttcaagcat ttaaacattt tcattgaatt   4260
ataaaatatt atttgtaaaa gaaagaaaaa cagcacaact gcagattaca gatgactaag   4320
atagatgaat catgaaaagg tgctagattg tgagcggata acaatttcac acaggaaaca   4380
gctatgacca tgattacgcc aagctctcga cgggatcgcg gccgcgatcc agacatgata   4440
agatacattg atgagtttgg acaaaccaca actagaatgc agtgaaaaaa atgctttatt   4500
tgtgaaattt gtgatgctat tgctttattt gtaaccatta taagctgcaa taaacaagtt   4560
ggggtgggcg aagaactcca gcatgagatc cccgcgctgg aggatcatcc agccggcgtc   4620
```

-continued

```
ccggaaaacg attccgaagc ccaacctttc atagaaggcg gcggtggaat cgaaatctcg   4680
tgatggcagg ttgggcgtcg cttggtcggt catttcgaac cccagagtcc cgctcagaag   4740
aactcgtcaa gaaggcgata gaaggcgatg cgctgcgaat cgggagcggc gataccgtaa   4800
agcacgagga agcggtcagc ccattcgccg ccaagctctt cagcaatatc acgggtagcc   4860
aacactatgt cctgatagcg gtccgccaca cccagccggc cacagtcgat gaatccagaa   4920
aagcggccat tttccaccat gatattcggc aagcaggcat cgccatgggt cacgacgaga   4980
tcctcgccgt cgggcatgct cgccttgagc ctggcgaaca gttcggctgg cgcgagcccc   5040
tgatgctctt cgtccagatc atcctgatcg acaagaccgg cttccatccg agtacgtgct   5100
cgctcgatgc gatgtttcgc ttggtggtcg aatgggcagg tagccggatc aagcgtatgc   5160
agccgccgca ttgcatcagc catgatggat actttctcgg caggagcaag gtgagatgac   5220
aggagatcct gccccggcac ttcgcccaat agcagccagt cccttcccgc ttcagtgaca   5280
acgtcgagca cagctgcgca aggaacgccc gtcgtggcca gccacgatag ccgcgctgcc   5340
tcgtcttgca gttcattcag ggcaccggac aggtcggtct tgacaaaaag aaccgggcgc   5400
ccctgcgctg acagccggaa cacggcggca tcagagcagc cgattgtctg ttgtgcccag   5460
tcatagccga atagcctctc cacccaagcg gccggagaac ctgcgtgcaa tccatcttgt   5520
tcaaccatgg tggatcgatc caagctccca acacaactat gtcagaagca aatgtgagga   5580
gcaactgatc ctacctcacc ttatatgctc tgccctggct cctgccctct ctatcctgtg   5640
tgagcagatt ggcccttacc aaggtgtggc tctacggaat caggcttcgg tgatgacaag   5700
catatttctc cctagaatgc tgtgccactc actggcttag gagtctcagc tctgggtact   5760
ccctctgaat aatgtttgtc cttatctgtg cagagaacac tgtctctaaa gcatcctttt   5820
tggcaacgca tttgctcaat caactactga attggtgtta aaattaattt tccttttttt   5880
ctcattatgc aaataagaaa ttgagaagca aagctagcag agatttctat cacacctatc   5940
agggatacac aatttccaag aatttcagaa gtgtttggtg ttcctattaa cataaatccg   6000
gaaataacac ctgagtgaac tgtcttctaa ttcttcaact ggatggcttt ttagtgtaaa   6060
agatgttgaa tactgattga ctttttaata attttatagt atatgtcaga aatattgcac   6120
agtccctatt tacatcattc tacagtggtt tttaaaatgt tttaagaata aaaaacatga   6180
aaactttatt tgatttttct gaggaaataa ctttttggat ttaatttcaa tgaaaccgtt   6240
gataacattt ccctccccaa caatctctgg caacgatccc tcagatttta atgattatgt   6300
attattacct tttaatacaa gtagaataac actcagggaa tttacaacat ttgttatttt   6360
cagtaaatac attggttgaa gtttaaaagt ctatccgtag taaacttaca tctttcagga   6420
gcttggtcaa tgtgttctgg acaaagcagg aagatgtgac tgaaatcctg aaaggagccg   6480
gctcctgcag cacaaggata atgatacatc tgggtacatt tctcttcaca gcatttgata   6540
gtggctccaa agtgcttaca aaatgcacat tgctgaaagg ggtaaaggag agaaatctct   6600
ttataaaacc ttgaaaagga atatttaaat ataagctggg aaggtataaa aaactctctg   6660
taacatcaca agtaaacaaa ttgaacctgc aaaatattaa acaaaggatt cattaaaaat   6720
aataaaatct acattactca atttagtgct ttgtgtgcta ccaactcatc cttccattca   6780
aattagaaag ttagaatttc attccttata ttttcaaaaa taaattgtga agcattttag   6840
aaacaaaacc taaaattttt ttttaaaagc aaatagtaat atggttaaag gggcaggttt   6900
ctatattgag gattattata aagtttttaa atcctaccaa aactagtaat aggaacatat   6960
```

-continued

```
attatttatg agacatatta ctatttttta ccctgcctaa aaataaatac aaataaattc   7020
atcaattata agttaacagg gacacaaatg gttaaagact cacacacaaa aaaaacaaaa   7080
ctacatactt caatgtagca atcaacttca aatttcttaa caaaagatgg aaatgttggg   7140
gaaaaaatta gtcatctggt atctttccca tttcaacctg cctccattat cttgcaagtg   7200
gtaaaatgca cagaaataag cctcaaacaa gaggggcagt ctagggcaag tgaacacata   7260
agtcggaaga aattatgtaa aatgttgcat ttacttattc agttttccct tagaatgatt   7320
cacaaactct tcctcattct cccaagtcca ttttgagtat cattttcttt gaagagagtc   7380
tgatgggccc tgtactatac agtatgaaat ctctctgtgg gaaatgacta tctaacataa   7440
atttttgttt acaccgttac atggtaccta cttgcttatg ccattacatg atcagtttac   7500
ctttttctca acctaatcca agatccttca attgaggcac tatactatct ttgtatccaa   7560
agcaccaaaa atgctgcttc aaacaggccc taatagatag gtgttcctat acatatacca   7620
aaaagactta acttttggtg atcttgtttg tgagtgtggc tcataaacag cttagttgag   7680
ataactggag cctcatgtag cagagacagt tggaccctgc taacattact gtggatatct   7740
tcacatgtta ctacattgac tttatattct gctaattaac cagggactac agtagttaaa   7800
attataattg ttttcaatgt tttatgtgta aatctgtatc tcacatacta tcaaactctt   7860
cctcactgtc atcagtctac tgcattgaat ccaacataac aaagctaaat gactcctgag   7920
ggctgaatca gaaagaagaa aagaaagaga tacaaaactt tagtcggccc ggtggctcac   7980
acctgtaatc ccagcacttt ggaaggccaa ggcgggcgga tcacgaggtc aggagatcga   8040
gaccatcctg gctgatacag tgaaactcca tctctactga aaatacaaaa aattagctgg   8100
acgtggtggt gggcacctgt agtcccagct actcaggagg ctgaagcagg agaagcttct   8160
aaataactca taaacactaa ttactgttgt gacactttaa ttttatacaa tatttataag   8220
tatacagaat aacatttcag tgctattttg gcactcaagg gtattaatgc atagcttgag   8280
tattctatag tgtcacctaa atagcttggc gtaatcatgg tcatagctgt ttcctgtgtg   8340
aaattgttat ccgctcacaa ttccacacaa catacgagcc ggaagcataa agtgtaaagc   8400
ctggggtgcc taatgagtga gctaactcac attaattgcg ttgcgctcac tgcccgcttt   8460
ccagtcggga aacctgtcgt gccagctgca ttaatgaatc ggccaacgcg cggggagagg   8520
cggtttgcgt attgggcgct cttccgcttc ctcgctcact gactcgctgc gctcggtcgt   8580
tcggctgcgg cgagcggtat cagctcactc aaaggcggta atacggttat ccacagaatc   8640
aggggataac gcaggaaaga acatgtgagc aaaaggccag caaaaggcca ggaaccgtaa   8700
aaaggccgcg ttgctggcgt ttttcgatag gctccgcccc cctgacgagc atcacaaaaa   8760
tcgacgctca agtcagaggt ggcgaaaccc gacaggacta taaagatacc aggcgtttcc   8820
ccctggaagc tccctcgtgc gctctcctgt tccgaccctg ccgcttaccg gatacctgtc   8880
cgcctttctc ccttcgggaa gcgtggcgct ttctcatagc tcacgctgta ggtatctcag   8940
ttcggtgtag gtcgttcgct ccaagctggg ctgtgtgcac gaaccccccg ttcagcccga   9000
ccgctgcgcc ttatccggta actatcgtct tgagtccaac ccggtaagac acgacttatc   9060
gccactggca gcagccactg gtaacaggat tagcagagcg aggtatgtag gcggtgctac   9120
agagttcttg aagtggtggc ctaactacgg ctacactaga aggacagtat ttggtatctg   9180
cgctctgctg aagccagtta ccttcggaaa aagagttggt agctcttgat ccggcaaaca   9240
aaccaccgct ggtagcggtg gtttttttgt ttgcaagcag cagattacgc gcagaaaaaa   9300
aggatctcaa gaagatcctt tgatcttttc tacggggtct gacgctcagt ggaacgaaaa   9360
```

```
ctcacgttaa gggattttgg tcatgagatt atcaaaaagg atcttcacct agatcctttt   9420
aaattaaaaa tgaagtttta aatcaatcta aagtatatat gagtaaactt ggtctgacag   9480
ttaccaatgc ttaatcagtg aggcacctat ctcagcgatc tgtctatttc gttcatccat   9540
agttgcctga ctccccgtcg tgtagataac tacgatacgg gagggcttac catctggccc   9600
cagtgctgca atgataccgc gagacccacg ctcaccggct ccagatttat cagcaataaa   9660
ccagccagcc ggaagggccg agcgcagaag tggtcctgca actttatccg cctccatcca   9720
gtctattaat tgttgccggg aagctagagt aagtagttcg ccagttaata gtttgcgcaa   9780
cgttgttggc attgctacag gcatcgtggt gtcacgctcg tcgtttggta tggcttcatt   9840
cagctccggt tcccaacgat caaggcgagt tacatgatcc cccatgttgt gcaaaaaagc   9900
ggttagctcc ttcggtcctc cgatcgttgt cagaagtaag ttggccgcag tgttatcact   9960
catggttatg gcagcactgc ataattctct tactgtcatg ccatccgtaa gatgcttttc  10020
tgtgactggt gagtactcaa ccaagtcatt ctgagaatac cgcgcccggc gaccgagttg  10080
ctcttgcccg gcgtcaatac gggataatag tgtatgacat agcagaactt taaaagtgct  10140
catcattgga aaacgttctt cggggcgaaa actctcaagg atcttaccgc tgttgagatc  10200
cagttcgatg taacccactc gtgcacccaa ctgatcttca gcatctttta ctttcaccag  10260
cgtttctggg tgagcaaaaa caggaaggca aaatgccgca aaaaagggaa taagggcgac  10320
acggaaatgt tgaatactca tactcttcct ttttcaatat tattgaagca tttatcaggg  10380
ttattgtctc atgagcggat acatatttga atgtatttag aaaaataaac aaataggggt  10440
tccgcgcaca tttccccgaa aagtgccacc tgtatgcggt gtgaaatacc gcacagatgc  10500
gtaaggagaa aataccgcat caggcgacgc gccctgtagc ggcgcattaa gcgcggcggg  10560
tgtggtggtt acgcgcagcg tgaccgctac acttgccagc gccctagcgc ccgctccttt  10620
cgctttcttc ccttcctttc tcgccacgtt cgccggcttt ccccgtcaag ctctaaatcg  10680
ggggctccct ttagggttcc gatttagagc tttacggcac ctcgaccgca aaaaacttga  10740
tttgggtgat ggttcacgta gtgggccatc gccctgatag acggtttttc gccctttgac  10800
gttggagtcc acgttcttta atagtggact cttgttccaa actggaacaa cactcaaccc  10860
tatctcggtc tattcttttg atttataagg gattttgccg atttcggcct attggttaaa  10920
aaatgagctg atttaacaaa tatttaacgc gaattttaac aaaatattaa cgtttacaat  10980
ttccattcgc cattcaggct gcgcaactgt tgggaagggc gatcggtgcg ggcctcttcg  11040
ctattacgcc agctggcgaa agggggatgt gctgcaaggc gattaagttg ggtaacgcca  11100
gggttttccc agtcacgacg ttgtaaaacg acggccagtg aattgtaata cgactcacta  11160
ta                                                                 11162
```

<210> SEQ ID NO 3
<211> LENGTH: 30
<212> TYPE: DNA
<213> ORGANISM: Artificial Sequence
<220> FEATURE:
<223> OTHER INFORMATION: TPCF primer to amplify TPA and FIX gene and expression elements.

<400> SEQUENCE: 3

```
atgcatccta ggggaggtcg ctgagtagtg                                      30
```

<210> SEQ ID NO 4
<211> LENGTH: 29

-continued

```
<212> TYPE: DNA
<213> ORGANISM: Artificial Sequence
<220> FEATURE:
<223> OTHER INFORMATION: TCPR primer to amplify TPA and FIX gene and
      expression elements.

<400> SEQUENCE: 4

tgcatgccta ggtaccccct agagcccag                                   29
```

HUMAN SOURCE LEADING SEQUENCE, GENE VECTOR AND GENE EXPRESSION STRATEGY

RELATED APPLICATIONS

This application is the national phase under 35 U.S.C. § 371 of PCT International Application No. PCT/CN01/00126 which has an International filing date of Feb. 16, 2001, which designated the United States of America.

SUMMARY OF THE INVENTION

The invention deals with gene targetinger sequence, by which a gene vector was constructed. The invention also relates to a strategy for expression of a target gene introduced by the gene vector.

BACKGROUND OF THE INVENTION

Statistical data of Mendelian inheritance in man demonstrates, up to now, that 1660 single gene disorders have been identified and 989 disease-related genes have been identified before Jun. 30, 2000. Most recessive genetic disorders may be treated by introducing the normal gene into cells of the patient. With the advancement of research, gene therapy regarding dominant genetic disorders and somatic cell-related tumors has begun. In 1995, E. Marshall put forward in *Science* that the key point of gene therapy research was novel vector development and discovery, but the problem of an effective gene therapy vector remain unsolved so far. The main reason is that the researchers do not step out of the circle of constructing a vector using viral components. General speaking, commonly-used viral vectors have many defects as follows: 1) Instability: gene insertion efficiency is low, and the vector exists in the cell nucleus partially as a form of an attached body that is not inherited stably during cell division. As a result, the therapeutic gene cannot be expressed for a long time and in a stable manner. 2) Poor safety: for example, mutation caused by random insertion may affect function of normal genes at integration sites, and even activate an oncogene, which may result in other diseases and tumors respectively. Furthermore, viral vectors may generate wild-type recombinant virus with replication ability and so harm the patient. In recent years, it was reported that an adenovirus vector caused a patient death during the conduct of a gene therapy. 3) Immunogenicity: the proteins produced by viral genes and protein contaminating the vector during purification could induce an immunogenic reaction and influence the expression of the therapeutic gene.

In the middle of the 1980's, a gene targeting vector was developed based on the principle of homologous recombination to achieve site-directed integration, which could avoid immunogenicity and random integration, but the gene targeting vector used for site-directed repair in gene therapy and replacement of a defective gene have to utilize specific fragments of the two sides of the gene as targeting sequences, therefore its application is limited and the transfection efficiency is still low. In fact, it is useful for gene knock-out in embryonic stem cells and fertilized egg cells, but is not suitable for site-directed integration in mature somatic cells (Galli-Taliadoros L A, Sedgwick J W, Wood S A, et al. J Immunol Meth 1995, 181:1-15; Hasty P, Rivera-Perez J, Chang C, et al. Mol Cell Biol 1991, 11(9):4509-4517).

Rosenbery concluded that no case had shown certain clinical efficacy among hundreds of gene therapy experiments (Rosenbery L E & Schechter A. N. Science, 2000; 287:1751). Thus, development of a novel, stably inherited gene vector causing no harm to a human body remains a key problem to be solved.

DETAILED DESCRIPTION OF THE INVENTION

In 1981, the applicant found two families carrying a rarely reported bi-satellite microchromosome (BM), but the phenotype is normal. The microchromosomes have been stably inherited in two families over 2 and 3 generations and show no harm to a human body. Through document investigation, we found that there were seven similar families in both Europe and USA. Up to now, total 17 families have been reported, but no one has thought to use this chromosome as a source of components for gene vector construction. The inventor put forward in 1991 a proposal for dissection of components this chromosome and construction of a gene vector having a human source. The project was initiated in 1994 and executed in 1995. The applicant first detected during investigation that the bi-satellite microchromosomes (BM) originated from the short arms of human D and G group chromosomes, including chromosomes 13, 14, 15, 21 and 22. The short arms of D, G group chromosomes contain a nucleolus organizing region and are rich in ribosomal DNA. Preliminary biological research has revealed that polymorphism of different lengths (namely containing different concentrations of rDNA) were commonly found in this region in the population, and the genes here could be transcribed very actively during cell division. Therefore, the applicant inferred that if a specific fragment from the BM could be isolated and used as a targeting sequence, a foreign gene can then be transferred in a site-directed manner into the nucleolus organizing region, and the expression of the gene should be effective, stable and unharmful. Subsequent experiments have strongly proved that inference.

It is of great significance to find the BM and isolate specific DNA fragments showing homology to the nucleolus organizing region in the short arms of human D, G group chromosomes.

The applicant first constructed a BM-specific pUC19 library by micro-dissection, PCR and microcloning techniques, and then isolated a single copy fragment by screening this library. The single copy fragment was proved to be from BM and the short arms of D, G group chromosomes by Fluorescent In Situ Hybridization (FISH). The single copy fragment was further used as probe to screen a PAC genome library and thus a DNA fragment of 120 kb (BMSF) (SEQ No.1) was obtained. This DNA fragment was also confirmed to originate from the short arms of human D, G group chromosomes (FIG. 1). Sequence analysis indicated no physiological function-related genes were found in the BMSF fragment, suggesting the target site is safe.

It is within the aim of the invention to isolate a DNA sequence that does not contain an important physiological function-related gene from the short arms of human D, G group chromosomes or a sequence sharing 50% or great than 50% similarity to short arms in human D, G group chromosomes as a gene targeting sequence. For example, in example 1, a sequence was selected from SEQ ID NO: 1 to construct a gene vector having a human source. This sequence comes from the short arms of human D, G group chromosomes.

The 120 kb DNA fragment above can be used as gene targeting sequence, and a smaller fragment with specificity can also be selected from the 120 kb DNA fragment. In the applied case, a 3.8 kb fragment from nucleotide 75590 to 79448 in the SEQ No. 1 is selected as a gene targeting sequence (GLS). According to the requirements of gene vector construction, positive and negative screening genes should be added to the vector, too.

More concretely, to construct a human gene therapy vector, the 3.8 kb fragment from nucleotide 75590 to 79448 of SEQ ID NO: 1 was inserted into the pGEM-TK vector, which contained a negative screening thymidine kinase gene (TK). A positive screening gene Neo was inserted into site 1500 of the GLS which divided the GLS into two arms of 1.5 kb and 2.3 Kb. Thus, the gene vector was constructed. The bacterial strain containing the gene vector was deposited in the China Typical Culture Collection Center on Sep. 29, 2000 (Wuhan University, Wuhan 430072, China). The accession number is CCTCCM200030. The administrator designated the reserve classification nomenclature which is *Escherichia coli* JM109/JH-4/pNS2. FIG. 2 shows the vector, and the sequence is given in SEQ ID NO: 2.

This present invention provides a specific target site coming from SEQ ID NO: 1 which denotes a DNA targeting sequence originated from the short arms of a D, G group chromosome. The gene vector comprising the fragment above can transfer a gene of interest into specific target sites which are include no important physiological function-related genes, therefore targeting is safe.

Based on the invention technology, the applicant further put forward the following procedures for gene expression.

(1) A gene vector is constructed using a DNA sequence with no vital physiological function-related genes obtained from the short arms of Group D,G chromosomes of a human being, or by using a targeting sequence which is 50% or greater than 50% homologous to such a DNA sequence;

(2) Clone a gene of interest into the above-described gene vector;

(3) Transfer the gene of interest into target sites of the nucleolus organizing region of group D,G chromosomes of host cells;

(4) Express the gene of interest in vivo and in vitro.

All procedures including gene vector construction, recombination of gene of interest into the vector, transfer of gene of interest into host cells and expression of the gene of interest can be conducted by conventional technologies.

The targeting sequence of the gene of interest can be a portion of the sequence selected from the DNA sequence of SEQ ID NO: 1. Preferably, the targeting sequence of the gene of interest is the portion at the positions from 75590 to 79448 SEQ ID NO: 1.

The gene targeting sequence above can be used to construct a gene vector containing positive and negative screening genes.

The examples 2 and 3 of the present invention explain the procedures above:

① A preferred specific DNA fragment of 3.8 kb selected from BMSF of 120 Kb is subcloned into a pGEM-TK plasmid vector, which uses TK as a negative screening gene. A positive screening gene Neo was inserted into the 3.8 kb DNA fragment to construct a gene vector. ② A gene of interest digested by a restriction enzyme is ligated into the exogenous gene cloning site on one side of the Neo gene. The existence of all parts and their orientation is confirmed by polymerase chain reaction. ③ A single restriction enzyme digestion site in the pGEM vector selected and the gene vector is linearized. The gene vector is transferred into target cells by means of electroporation or liposome transfection. ④ Transformed target cells are screened using G418 and GCV to obtain site-directed integrating positive cells clones. ⑤ The expression of the gene of interest is detected from positive cell clones so as to obtain site-directed integration into the short arms of D, G group chromosomes and stable expression of the gene of interest.

The positive cells expressing the gene of interest obtained by the screening are embedded hypodermically or injected intravenously into the body or the gene of interest encapsulated by liposomes is directly injected into the body so that gene is expressed for a long time and stably within the body to correct the clinical symptom caused by the defective gene.

The example of the present invention provides a DNA sequence of a gene vector as shown as SEQ ID NO: 2, of which the targeting sequence is from 75590 to 79448 of SEQ ID NO: 1. TK is a negative screening gene. The positive screening gene Neo is inserted into site 1500 of the GLS and the GLS is divided into two arms of 1.5 kb and 2.3 kb. The cloning site is at nucleotide 5910. The example of the present invention made public in vitro expression in HT1080 cells of genes of tissue-type plasminogen activator (TPA) used for treatment of lood occlusion disorders and coagulant factor IX (FIX) used for treatment of haemophilia B. These experiments showed the expression is both efficient and stable.

Therefore, gene expression strategies provided by the present invention are of great promise in practical applications. The gene expression strategies are not only used for manufacturing medicinal protein but also give an effective way for gene therapy.

The inventor made use of a chromosome segment not harmful to the human being body as an unique material and created a completely novel strategy. It is novel that the inventor first found that the short arm nucleolus tissue region of human D, G group chromosomes is the best target site for human gene therapy and expression (10 sites are present in the short arms of the nucleolus tissue regions of chromosomes 13, 14, 15, 21, 22). A gene vector capable of transferring a gene of interest site-directedly into these target sites is also novel.

Compared with background technologies, the present invention has some striking advantages:

1. Good stability: using the DNA sequence provided by the invention to construct a vector, the human source gene vector can transfer site-directedly a gene of interest into the short arms of D, G group chromosomes of human somatic cells and allow the gene of interest to be inherited stably with chromosomes;
2. Good safety: the target site contains no vital physiological function-related gene, demonstrating that the target site is safe. Meanwhile Fluorescent In Situ Hybridization (FISH) confirmed the vector could insert a gene of interest site-directedly into a safe target site in cells (FIGS. 3, 4), excluding insertion mutation at random integration sites and the harm of recombinant wild-type virus. The expression of a gene of interest in target sites is safe. Although the present examples do not provide clinical demonstration of gene expression strategies, the practical examples in example 4 confirm its safety from another angle.
3. Efficient expression: First, the gene vector provided by the present invention comes from targeting sequence at short arms of human D, G group chromosomes so correspondingly there are 10 target sites in human cells and the insertion efficiency is 5-10 times higher at least than any other vectors. Second, because the targeting sequence comes from short arms of D, G group chromosomes where genes are actively transcribed, the gene of interest is delivered into target sites where it can express highly efficiently.

4. No immunogenicity: the vector comes from a human being, therefore it has no immunogenicity to a human being.

Figure 1:
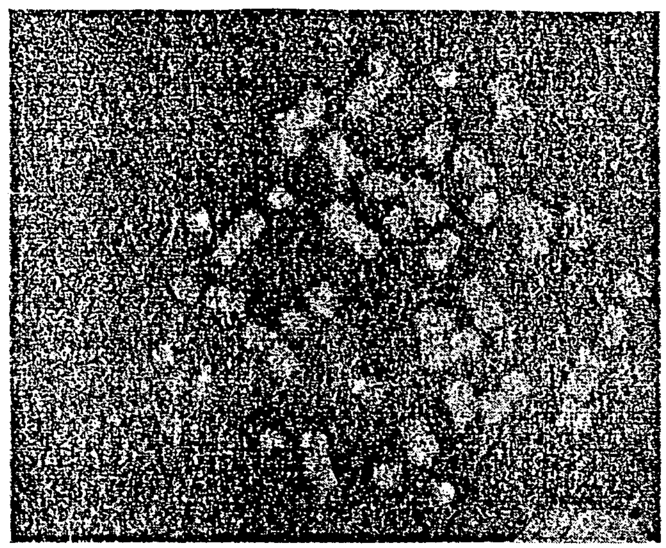
FIG. 1 is mapping by FISH of a 120 kb DNA fragment cloned in PAC.
Figure 2:
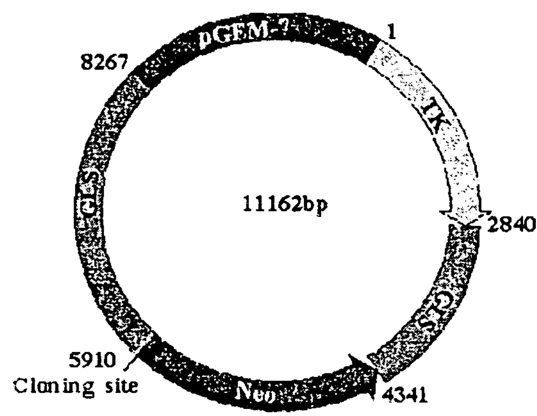
FIG. 2 is a structure map of a gene vector (the whole length of the gene vector is 11162 bp); the features of which shown are: pGEM-7 (8267-11162): vector replication elements and prokaryotic screening system; TK (1-2840): Eukaryotic cell negative screening gene which utilizes TK promoter and TK poly A signal; Neo (4342-5910): eukaryotic cell positive screening gene which utilizes sv40 promoter and sv40 poly A signal; GLS (2841-4341, 5911-8267): targeting sequence; Cloning site (5910): insert site of the gene of interest.

The examples of the invention are only illustrative and should not be considered to be limiting of the present invention.

EXAMPLE ONE

The preparation of the gene targeting sequence provided in the present invention:

1. Obtaining a PAC clone containing a gene targeting sequence 1.1 Construct a BM-specific pUC19 library by microdissection, PCR and microcloning technologies (Deng H—X, Yoshiura K, Dirks R W, et al. Hum Genet 1992, 89:13.)

1.2 Obtaining and identifying BM-specific single copy DNA (1) The preparation of colony matrix membrane: Draw squares 14×14 on two pieces of nylon membrane and mark them A and B. Place the two membranes on two plates containing solid LB medium, respectively. Pick at random white clones and transfer the clones into squares of two same coordinates, a total of 14×12 clones. Single copy DNA of 100 ng is added to the line 13 as a positive control. No addition of DNA is used as a negative control. The two plates are respectively placed in a incubator at 37° C. for 10-12 hr, then membrane B is kept at 4° C. Membrane A is taken out of the plate, and processed with filter papers immersed in the following solutions: 10% SDS, 5 min, 0.5N NaOH/1.5M NaCl, 3 min, 1.5M NaCl/0.5M Tris.HCl, 3 min, 2×SSC/0.2M Tris.HCl, 10 min. Membrane A is then dried under vacuum at 80° C., 2 hr and stored at 37° C. for use.

(2) The preparation of gDNA probes

Sample 50-70 ng of gDNA and make up with sterile-water to 11 ml, boil at 100° C., 10 min, denature, label using the following reaction system:

| | |
|---|---|
| 2 mM *dNTP(dATP)* | 3 ul |
| primer mixture | 2 ul |
| klenow enzyme | 1 ul |
| $\alpha$-$^{32}$*P-dATP* | 3 ul |

mix, incubate for 30 min at 37° C. in bath, add 8 ul stop mixture, filter through G-50 column to purify the probe, take one-tenth for liquid scintillation counting.

(3) Hybridization: colony dot matrix membrane is placed in 2×SSC and immersed for 10 min. The debris on the surface of membrane is carefully removed. The membrane is pre-hybridized at 65° C. in 5 ml hybridization liquid for 30 min at least. According to the value of liquid scintillation, based on $1.2\times10^6$ cpm/ml hybridization liquid, sample probe liquid, boil at 100° C., 10 min, denature, add 5 ml fresh hybridization liquid to colony dot matrix membrane and allow to hybridize for over 12 hrs at 65° C. Then wash the membrane under following conditions: 2×SSC/0.1% SDS, 10 min at room temperature, 2×SSC/0.1% SDS, 10 min at 65° C., 0.1×SSC/0.1% SDS, 10 min at 65° C. Autoradiography is performed at −70° C.; a strong or weak hybridization signal is considered to be single copy.

(4) Sequencing, Southern blotting detection: Clones without hybridization signal are picked from the corresponding position of membrane B, expanded, and plasmid DNA is extracted for DNA sequencing. The obtained DNA sequences are compared with the GenBank database; the clones without similarity to other sequence is considered to be single copy. Finally, inserted DNA is isolated by restriction enzyme digestion. The insert is labeled by $\alpha$-$^{32}$P-dATP by random primer method and then hybridized with EcoR1 digested gDNA on a nylon membrane; the clone showing one or two bands is considered to be single copy.

1.3 Obtaining and identifying BM and short arms of group D, G chromosomes specific PAC clone (1) Screen human PAC gDNA library to obtain positive clone to label The single copy probe P8-7 of 260 bp is labeled using $\alpha$-$^{32}$P-dATP by the random primer method and the probe is purified by G-50 column (middle size of particles) and stored at 4° C. Seven pieces of PAC membranes immersed in 2×SSC for 10 min are pre-hybridized for 3 hr at 55° C. Probe DNA is denatured for 10 min at 100° C. and added to 50 ml hybridization solution purchased commercially according to dosage of $4.6\times10^5$ cpm/ml and hybridized to PAC membrane for 1 hr at 65° C. The membrane is washed as follows: 2×SSC, 10 min one time at ambient temperature, 2×SSC/0.1% SDS, 10 min at 65° C., twice and then placed onto x-ray film.

Autoradiography is performed for 12 hours and the X-ray film is developed and positive clones counted as instruction goes.

(2) pick at random a number of positive clones from five different plates, purchase PAC clones.

1.4 FISH of PAC DNA to metaphase cells of the PAC confirms DNA was from group D,G chromosome, as shown in the FIG. 1.

Experimental methods referred to above are found in Molecular Cloning. Second Edition (Cold Spring Harbor Laboratory Press, 1989)

2. Isolation of gene targeting sequence DNA

Main materials: β-agarase (Bio-Labs) Not I Agarase

① Digest PAC 169 Plasmid by Not I enzyme;

② Isolate Insert DNA of 120 Kb by PFGE;

Pulse electrophoresis conditions: electrode buffer solution: 0.5×TBE, high strength Analytical Grade Agarase (Bio-Rad, Low Melting point Agarose LMP) 1%, Switch time: 2 seconds→15 seconds→electrophoresis time: 18 hr, voltage: 6V/cm, angle: 120°, temperature: 14° C.

③ after electrophoresis, stained with EB (0.2 ug/ml), 30 min, excise band of 120 kb.

④ the excised gel piece is treated with β-agarase, and the DNA is precipitated in alcohol.

EXAMPLE TWO

The preparation of gene vector provided by the present invention

1. Construction of gene vector and transfer of gene of interest 1.1 Construction of vector 1.1.1 PAC DNA is digested by Nsi I and Stu I (blunt enzyme), 3.8 kb DNA fragment is recovered by general agarose gel electrophoresis and purification by electro-elution;

1.1.2 Digest pGEM-TK vector DNA by Hind III, make it blunt by Klenow enzyme, to generate a blunt end;

1.1.3 The linearized pGEM-TK/Hind III is further digested by Nsi I;

1.1.4 The digested PAC DNA of 3.8 kb and pGEM-TK were ligated at 16° C. for 17 hr;

1.1.5 Ligated product was transformed into JM109 competent bacteria. The transformed bacteria were incubated on a plate containing ampicillin for 18 hr at 37° C.;

1.1.6 Pick individual clones at random, determine positive clones by Nsi I and Nhe I digestion after plasmid extraction. The recombinant plasmid was named pGEM-TK-3.8 Kb.

1.1.7 Obtain Neo gene by digesting pCDN-GPR plasmid with Xba I and Nhe I.

1.1.8 Ligate Xba I and Nhe I digested Neo gene with Nhe I digested pGEM-TK-3.8 Kb to construct pNS2 gene vector;

2.1 Transfer of TPA and FIX genes 2.1.1 Clone TPA and FIX (CDS) into pcDNA3.1 (−), respectively;

2.1.2 Design the primers TPCF and TPCR to amplify TPA and FIX gene and expression elements (CMV promoter and BGH poly A signal), introduce enzyme Avr II restrictive sites into the two ends of primers, the sequences of the primers are:

```
TpcF:     ATgCATCCTAggggAggTCgCTgAgTAgTg
                 AvrII

TpcR:     TgCATgCCTAggTACCCCCTAgAgCCCAg
                 AvrII
```

2.1.3 Digest the amplified TPA or FIX gene and expression components (CMV promoter and BGH poly A signal) by Avr II, and ligate into pNS2 vector digested by NheI enzyme.

The procedures above are found in J. Sambrook et al. "Molecular Cloning". Second Edition. Cold Spring Harbor Laboratory Press. 1989

3. Extraction of gene vector DNA 3.1 Materials 3.1.1 QIAGE Plasmid Maxi Kit 3.1.2 Culture Media: liquid LB

| | |
|---|---|
| Trypton | 5 g |
| Yeast extract | 2.5 g |
| NaCl | 2.5 g |
| Add ddH2O to | 500 ml |
| Autoclave | |

3.1.3 Ampicillin: 100 mg/ml (100×)

3.2 Procedures

1) Pick and inoculate positive clones into 3 ml LB ($Amp^+$), incubate 1 hr at 37° C.

2) put 100 ul of primary culture above in 100 ml LB ($Amp^+$), incubate 16 hr at 37° C., 250 rpm 3) harvest bacteria by centrifugation at 6000 g for 15 min at 4° C.

4) add 100 ml buffer P to resuspend bacterial pellet 5) add 10 ml buffer P2, gently invert flask six times to mix up completely, stand for 5 min at ambient temperature 6) add 10 ml pre-cooled buffer P3, gently invert flask six times, place on ice for 20 min 7) centrifuge at 20000 g for 30 min at 4° C.

8) transfer swiftly supernatant to 40 ml centrifugation tube, centrifuge at 20000 g for 15 min at 4° C.

9) 10 ml buffer QBT equilibrates QIGEN tip 500

10) transfer the supernatant to QIGEN tip 500, filter through the column 11) wash the column with 2×30 ml buffer QC 12) elute the column with 15 ml buffer QF, collect the elution liquid 13) add isopropanol (0.7 times volume) 10.7 ml to elution solution, thoroughly mix up 14) centrifuge at 15000 g for 30 min at 4° C.

15) remove the supernatant, add 5 ml, 70% alcohol to DNA precipitate, centrifuge at 15000 g, 4° C. for 10 min 16) remove 70% alcohol, dry the DNA in the air for 10 min, add a certain amount of TE resolve DNA precipitate

EXAMPLE THREE

Introduce gene vector carrying TPA or FIX gene into host cells and express them in vitro 1. Materials 1.1 cell: HT1080 culture medium: high-sugar DMEM+10% FBS (HT1080)EMEM+10% FBS 1.2 Electroporation apparatus: Bio-Rad company 2. Methods:

1) Cells are inoculated in 75 $cm^2$ canted-neck flask, cultured and grown to 70%-80% confluence.

2) The cells are harvested and washed twice with HeBs buffer solution, and the cell number is counted.

3) Centrifuge at 1500 rpm, 4° C. for 10 min.

4) Resuspend with proper volume of HeBS, dilute the cell density to $10^6$-$10^7$/ml 5) Take 0.4 ml electroporation cuvette, add 0.8 ml cell suspension, 10 ul vector DNA 6) Electroporate the cells at 260v, 550 uFf, lasting 11-13 ms 7) The electroporated cells above are transferred into a 75 $cm^2$ canted-neck flask, 14 ml culture medium containing ampicillin/streptomycin is added, and the cells are incubated in 5% $CO_2$, at 37° C., 24-48 hr.

8) Add G418 to culture medium to a final concentration of 300 ug/ml, screen, replace culture medium every 2-3 days and renew G418. HT1080 cells without gene transfer were used as control 9) The control cells died after 7-10 days. The surviving clone cell number within transformed cells is counted, and maintained on a concentration of G418 of 150 ug/ml.

10) Continue to screen transformed cells with GCV of 500 ng/ml

Figure 3:
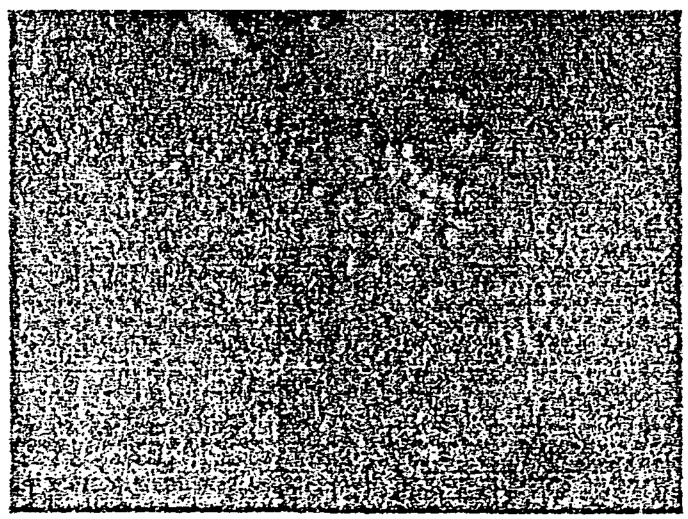
FIG. 3 is a FISH result showing mapping of an exogenous tPA gene in positive cloned cells, which demonstrates the vector can target a tPA gene site-directedly into short arms of D, G chromosomes.
Figure 4:
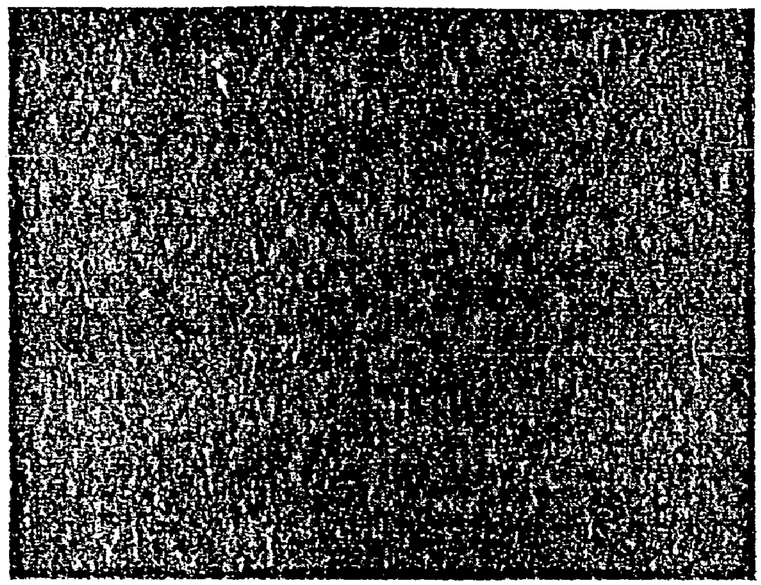
FIG. 4 is a FISH result showing mapping of an exogenous FIX gene in positive cloned cells, which demonstrate the vector can target a FIX gene site-directedly into short arms of D, G group chromosomes.

11) After most of the cell clones die after 7-10 days, add maintenance concentration of GCV of 250 ug/ml. When the remaining surviving cells grow up to 70%-80% confluence, detect the expression activity of transferred genes 3. Results TPA gene and FIX gene are introduced into HT1080 cells, respectively by electroporation using the human source gene vector. Positive clones were obtained after positive and negative screening. Site-directed integration of two genes were confirmed by FISH (FIGS. 3, 4). The results of activity determination are detailed in the following tables 1 and 2.

Figure 5:
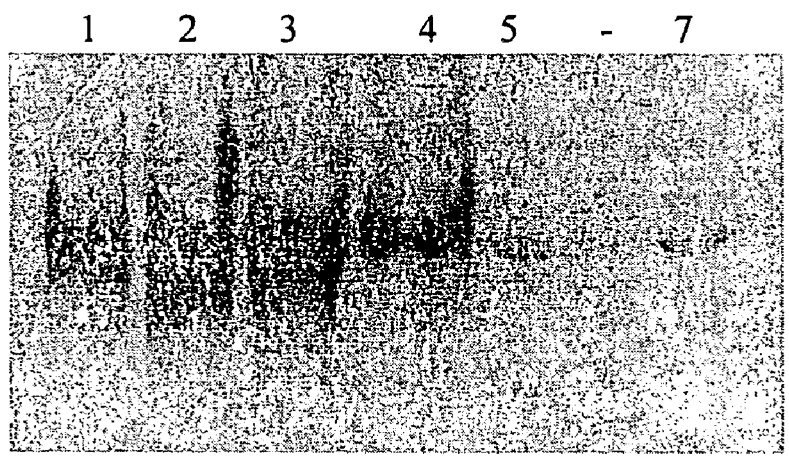
FIG. 5 shows a western blot of purified tPA, lanes 1-4 are purified product of tPA, "–" denotes a negative control.
Figure 6:
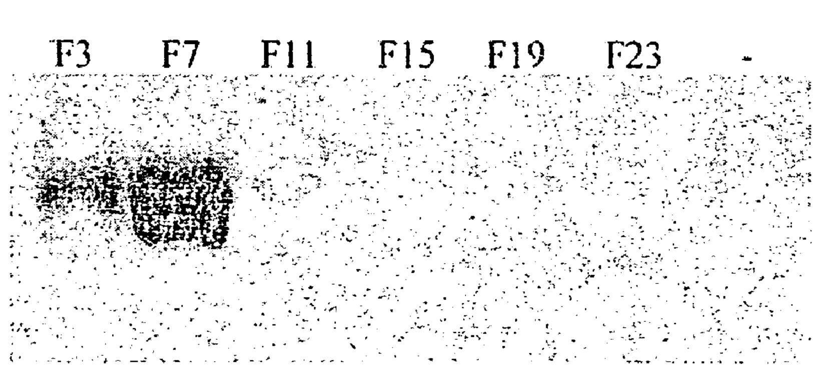
FIG. 6 shows a western blot of FIX positive cells, F3-F23 are six different cell strains, "–" denotes a negative control.

In negative control of HT1080 cells, TPA activity is 0 u/$10^6$ cells/24 hr, after the transfer, TPA activity is 408 u/$10^6$ cells/24 hr. Expression efficiency is 407 at day 95 after the transfer; the expression is very stable (Table 1). FIX activity is increased from less than 0.5 ug/ml up to 2.5 ul/ml, the expression content remains 2.6 ug/ml, see Table 2. The expressing products of two genes have been testified by Western Blotting (FIGS. 5,6). The expressed TPA protein has been purified.

TABLE 1 activity detection of positive cells transformed by TPA(ug/$10^6$ cells/24 hr)

| Days after transformed | T1 | days after transformed | T15 |
|---|---|---|---|
| 33 | 408 | 54 | 88 |
| 37 | 396 | 58 | 204 |
| 60 | 411 | 95 | 114 |
| 68 | 430 | | |
| 74 | 430 | | |
| 88 | 441 | | |
| 90 | 440.9 | | |
| 95 | 407 | | |

(T1, T15 are pTA positive cell strains)

TABLE 2 activity detection of FIX gene (ug/$10^6$ cells/24 hr)

| Days after transformed | clone F23 |
|---|---|
| 60 | 2.5 |
| 72 | 2.4 |
| 100 | 2.9 |
| 109 | 2.6 |

EXAMPLE FOUR

Safety case among human beings

Prof. Xia Jiahui has been engaging in human and medical cytogenetics since 1973. He found and identified 732 abnormal karyotypes first reported in the world, which were submitted by 470 clinical cytogeneticists working in 189 laboratories around China. Among these 732 karyotypes, 41 involve the short arms of D, G group chromosomes. No matter which chromosome among chromosomes 1-22 the fragment translocated into short arms of group D, G chromosomes originated, or how the lengths of fragments from the same chromosome are different, the number of gene contained is from one to thousands, but the phenotype of the carrier is normal, which shows that the genes translocated into short arms of D, G group chromosomes can express normally. So it is safe to use short arms of D, G group chromosomes as targeting sites for gene therapy.

1. Karyotype:46,XX,t(1;12;22;15;11;8) (1qter→1p11::8p23→8pter;12pter→12q11::1p11→pter; 22qter→22p11::12q11→12qter; 15pter→22p11→22pter;11pter→11q21::15q15→15qter;8qter→8p23::11q21→11qter)

phenotype: female, 28 years old, normal phenotype carrier material provider: Wu subing, Cytogenetics laboratory, Department of gynecology and obstetrics, first affiliated hospital of Zhongshan Medical University, Guangzhou 2. Karyotype: 46, XY, t(1;13) (1pter→1q32::13p11→13pter; 13qter→13p11::1q32→1qter).

Phenotype: female, 24 years old, normal phenotype carrier

Material provider: Xiao Chen, Department of biology, Harbin Medical University, Harbin 150086

3. Karyotype: 46, XX, t(2;15) (2pter→cen→15qter; 2qter→cen→15pter)

phenotype: female, 26 years old, normal phenotype carrier material provider: Guo Yuping, et al. Cytogenetics Department, Jiangxi provincial gynecology and obstetrics hospital, Nanchang 330006, Jiangxi province 4. Karyotype: 46,XY,t(2;21) (2pter→cen→21pter; 2qter→cen→21qter)

phenotype: male, 32 years old, normal phenotype carrier material provider: Kang Guoqing, et al. Department of genetics, the second affiliated hospital of Shangxi Medical College, Taiyuan 030001

5. Karyotype: 46,XY,t(3;21) (2qter→cen→22pter; 3qter→cen→22qter)

phenotype: male, 26 years old, normal phenotype carrier material provider: Gao Yun. Department of toxicology, Bingzhou municipal Medical College, Bingzhou 256603, Shangdong province 6. Karyotype: 46,XY,t(3;22) (3pter→cen→22pter; 3qter→cen→22qter)

phenotype: male, 29 years old, normal phenotype carrier material provider: Shi Huajin. Department of genetics, Jingzhou Women and Baby hospital, Jingzhou 121000, Liaoning province 7. Karyotype: 46,XX,t(4; 15)(4qter→4p13:: 15p13→15pter; 15qter→15p13::4p13→4pqter)

phenotype: female, 28 years old, normal phenotype carrier material provider: Zhou Ling, et al. Laboratory of genetics, the Wuhan Children hospital, Wuhan 430016, Hupei province 8. Karyotype: 46,XY,t(4;21)(4qter→4p15:: 21p11→21pter;21qter→21p11::4p15→4pqter)

phenotype: female, 25 years old, normal phenotype carrier material provider: Xu Jinfang, et al. Laboratory of genetics, the sixth people's hospital of Shanghai, Shanghai 200000

9. Karyotype: 46,XY,t(4;14)(4qter→4q31:: 14p11→14pter;14qter→14p11::4q31→4qter)

phenotype: male, normal phenotype carrier material provider: Zhou Mingjun, et al. Xuchang Municipal Central Hospital, Xuchang 161000, Henan province 10. Karyotype: 46,XY,t(4;14)(4qter→4q35:: 14p11→14pter;14qter→14p11::4q35→4qter)

phenotype: male, 27 years old, normal phenotype carrier material provider: Zhang Xiuquan, et al. Hushan Municipal Women and Nursling Hospital, Hushan 528000, Guangdong province 11. Karyotype: 46,XX, t(6; 22)(5qter→5q13:: 22p11→22pter; 22qter→22p11::5q13→5qter)

phenotype: female, 32 years old, normal phenotype carrier material provider: Zhao Jianping, Anyang Municipal Women and Nursling Hospital, Anyang 455000, Henan province 12. Karyotype: 46,XY, t(6;22) (6pter→cen6→22qter; 6qter→cen22→22pter)

phenotype: male, 25 years old, normal phenotype carrier material provider: Zhu Xinxia, et al. Laboratory of cytogenetics, Department of Gynecology and Obstetrics, Number 88 Hospital, Taian 271000, Shangdong province 13. Karyotype: 46,XY, t(6; 22)(6qter→6p21:: 22p11.2→22pter; 22qter→22p11.2::6q21→6pter)

phenotype: male, 33 years old, normal phenotype carrier material provider: Yang Qinglan, Department of Gynecology and Obstetrics, affiliated hospital of Bingzhou Medical College, Bingzhou 256603, Shangdong province 14. Karyotype: 45,XX,t(7;21) (7qter→7p22:: 21p12→21qter)

phenotype: female, 23 years old, normal phenotype carrier material provider: Sun Qingji, et al. Laboratory of genetics, the Wuhan Children hospital, Wuhan 430016, Hubei province 15. Karyotype: 46,XY/46XX,t(7;14)(7pter→7q11:: 14p11→14pter;14qter→14p11::7q11→7qter)

phenotype: male, 28 years old, normal phenotype carrier material provider: Li Luyun, Xia Jiahui, et al. State Key Laboratory of Medical genetics (Hunan Medical University), Changsha 410078, Hunan province 16. Karyotype: 46,XY,t(8;14)(8pter→8p21:: 14p12→14pter;14qter→14p12::8p13→8pter)

phenotype: male, 27 years old, normal phenotype carrier material provider: Shi Huajin, et al. Department of genetics, Jingzhou Women and Baby hospital, Jingzhou 121000, Liaoning province 17. Karyotype: 46,XY,t(9;14)(9pter→cen→14pter; 9qter→cen→14qter)

phenotype: male, 28 years old, normal phenotype carrier material provider: Cheng Qiuyun, et al. Department of reproduction medicine, first affiliated hospital of Hengyang medical college, Hengyang 421001, Hunan province 18. Karyotype: 46,XY,t(9;22) (9pter→9p13:: 22p12→22pter;22qter→22p12::9p13→9pter)mat phenotype: female, 31 years old, her mother, a young sister of her, a young brother of her and her son have the same phenotype as her, that is normal phenotype carrier material provider: Li Luyun, Xia Jiahui, et al. State Key Laboratory of Medical genetics (Hunan Medical University), Changsha 410078, Hunan province 19. Karyotype:46,XX,t(9;14) (9pter→9q12:: 14p12→14pter; 14qter→14p12::9q12→9qter). Phenotype: female, 32 years old, normal phenotype carrier Material provider: Sun Yanyang, et al, Department of biology, Harbin Medical University, Harbin 150086

20. Karyotype:46,XX,t(9;15) (9pter→9q21:: 15p12→15pter; 15qter→15p12::9q21→9qter)mat. Phenotype: female, 36 years old, normal phenotype carrier material provider: Zhu Guizhen, et al. Laboratory of cytogenetics, Department of Gynecology and Obstetrics, Number 88 Hospital, Taian 271000, Shangdong province 21. Karyotype:46,XX,t(10;13) (10pter→10q24:: 13p11→13pter; 13qter→13p11::10q24→10qter) Phenotype: female, 28 years old, normal phenotype carrier material provider: Yan Dunqing. Department of Gynecology and Obstetrics, affiliated hospital of Qingdao Medical College, Qingdao 266003, Shangdong province 22. Karyotype: 46,XX,t(10;13) (10pter→10q24:: 13p12→13pter; 13qter→13p12::10q24→10qter) Phenotype: female, 29 years old, normal phenotype carrier material provider: Zhang Yinru, et al. Department of neurology First affiliated hospital of Zhongshan Medical University, Guangzhou 510080, Guangdong province 23. Karyotype: 46,XX,t(11;14) (11pter→cen→14pter::11qter→cen→>14qter)

material provider: Wang Zhiyong, Department of genetics, Zhacheng County people's hospital, Zhacheng County 476200, Henan province 24. Karyotype: 46,XX,t(11;21) (11pter→11p11::21p11→21pter; 21qter→21p11::11p11→11pter)

Phenotype: female, 26 years old, normal phenotype carrier material provider: Zheng Jun, et al. Department of genetics, Shanxi provincial women and nursling hospital, Xian 710003 Shanxi province 25. Karyotype: 46,XX,t(11;15) (11pter→11q13::15p12→15pter; 15qter→15p12::11q13→11qter)

Phenotype: male, 23 years old, normal phenotype carrier material provider: Yang Ruifang, et al. Medical center of Obstetrics, affiliated hospital of Shandong Medical University, Jinan 250012, Shandong province 26. Karyotype:46,XX,t(12;14) (12pter→cen→14pter::12qter→cen→14qter)

Phenotype: female, 28 years old, normal phenotype carrier material provider: Han Weitian, et al. Department of eugenics, Liaoning provincial institute of family planing, Shenyang 110031, Liaoning province 27. Karyotype:46,XX,t(13;16) (13qter→13p11::16p11.2→16pter;16qter→16p11.2::13p11→13pter Phenotype: female, 27 years old, normal phenotype carrier material provider: An Songlan. Department of genetics, Dalian municipal gynecology and obstetrics, Dalian 110078, Liaoning province 28. Karyotype: 46,XY/46,XX,t(13;13) (13qter→13p12::13p12→13qter)

Phenotype: male, 39 years old, normal phenotype carrier material provider: Li Luyun, Xia Jiahui, et al. State Key Laboratory of Medical genetics (Hunan Medical University), Changsha 410078, Hunan province 29. Karyotype:46,XY,t(14;18) (14pter→cen→18pter; 14qter→cen→18qter)

Phenotype: male, 30 years old, normal phenotype carrier material provider: Wang Sugui, et al. Beijing Institute of family planing technology guidance, Beijing 100006

30. Karyotype:46,XX,t(14;15) (14pter→14q13::15p13→15pter;15qter→15p13::14q13→14qter)

Phenotype: female, 28 years old, normal phenotype carrier material provider: Li Luyun, Xia Jiahui, et al. State Key Laboratory of Medical genetics (Hunan Medical University), Changsha 410078, Hunan province 31. Karyotype:46,XX,t(15qter→cen→22qter)

Phenotype: female, 27 years old, normal phenotype carrier material provider: Li Luyun, Xia Jiahui, et al. State Key Laboratory of Medical genetics (Hunan Medical University), Changsha 410078, Hunan province 32. Karyotype:46,XY,t(15;18) (15pter→cen→18pter; 15qter→cen→18qter)

Phenotype: male, 30 years old, normal phenotype carrier material provider: Ren Guoqing, et al. Beijing Institute of family planing technology guidance, Beijing 100006

33. Karyotype:46,XX,t(15;20) (15pter→cen→2pter; 15qter→cen→2qter)

Phenotype: female, 26 years old, normal phenotype carrier material provider: Wang Xin, et al. Laboratory of genetics, department of obstetrics, the second affiliated hospital, Hunan Medical University, Changsha 410011, Hunan province 34. Karyotype:46,XX,t(15;22) (15pter→15q11::22p13→22pter;22qter→22p13::15q11→15qter)

Phenotype: female, 27 years old, normal phenotype carrier material provider: Hu Shengdi, Department of genetics, Hainan provincial people's hospital, Haikou 570011, Hainan province 35. Karyotype:46,XX,t(15;22) (15pter→15q22::22p11→22pter;22qter→22p11::15q22→qter)

Phenotype: female, 29 years old, normal phenotype carrier material provider: Li Murou, Department of genetics, Xinjiang Medical College, Urumchi 830054

36. Karyotype:46,XY,t(16;21) (16pter→16q11::21p11→21pter;21qter→22p11::16q12→16qter)

Phenotype: male, 29 years old, normal phenotype carrier material provider: Zhang Huifang, et al, Institute of family planing technology of Guangdong, Guangzhou 510080, Guangdong province 37. Karyotype:46,XX,t(18;21) (18pter→cen→21pter; 18qter→cen→21qter)

Phenotype: female, normal phenotype carrier material provider: Shi Huajin, et al. Laboratory of genetics, Jingzhou women and nursling hospital, Jingzhou 121000, Liaoning province 38. Karyotype:46,XX, t(18;21) (18pter→18q11::21p12→21pter;21qter→22p12::18q11→18qter)

Phenotype: female, 26 years old, normal phenotype carrier material provider: Li Xiulin, et al, laboratory of genetics, department of pediatrics, first affiliated hospital of Chinese medical university, Shenyang 110011, Liaoning province 39. Karyotype:45,X,dic(Y;13)(Ypter→Yp1200::13p11→cen→13qter)

Phenotype: male, 4 years old, normal phenotype carrier material provider: Xia Jiahui, et al. State Key Laboratory of Medical genetics (Hunan Medical University), Changsha 410078, Hunan province 40. Karyotype:46,XY,t(Y;15)(15qter→15p12::Yq12→Ypter) pat.

Phenotype: male, 4 years old, normal phenotype carrier material provider: Xia Jiahui, et al. State Key Laboratory of Medical genetics (Hunan Medical University), Changsha 410078, Hunan province Abnormal chromosome carriers described above showed no abnormal syndrome, which shows that not only can nucleolus tissue receive foreign genes but also it allows foreign genes to express normally.

The invention claimed is:

1. A vector consisting of:

i) targeting nucleotide sequences consisting of:

a sequence consisting of nucleotide positions 75590 through 79448 of SEQ ID NO:1; and a sequence consisting of nucleotide positions 77091 through 79448 of SEQ ID NO:1, wherein the targeting sequences provide for integration into the short arm of a human Group D or Group G chromosome;

ii) a marker gene providing for a positive selection for eukaryotic or human host cells that harbor the vector;

iii) a gene providing for negative selection for eukaryotic or human host cells that harbor the vector;

iv) a restriction enzyme site in the targeting nucleotide sequence, wherein the restriction enzyme site is unique in the vector; and v) a polynucleotide sequence that provides for replication of the vector in a prokaryotic host cell.

2. The vector of claim 1 that further comprises a desired polynucleotide inserted into the unique restriction site.

* * * * *